(12) United States Patent
Kath et al.

(10) Patent No.: US 7,109,337 B2
(45) Date of Patent: Sep. 19, 2006

(54) PYRIMIDINE DERIVATIVES FOR THE TREATMENT OF ABNORMAL CELL GROWTH

(75) Inventors: John Charles Kath, Waterford, CT (US); Michael Joseph Luzzio, Noank, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 11/127,809

(22) Filed: May 12, 2005

(65) Prior Publication Data

US 2005/0256145 A1    Nov. 17, 2005

Related U.S. Application Data

(60) Provisional application No. 60/571,312, filed on May 14, 2004, provisional application No. 60/500,742, filed on Sep. 5, 2003, provisional application No. 60/435,670, filed on Dec. 20, 2002.

(51) Int. Cl.
*C07D 401/14* (2006.01)
*C07D 403/12* (2006.01)
*C07D 403/14* (2006.01)
*A61K 31/506* (2006.01)
*A61P 35/00* (2006.01)

(52) U.S. Cl. ...................... 544/324; 514/275
(58) Field of Classification Search ................ 544/324, 544/323; 514/275
See application file for complete search history.

(56) References Cited

U.S. PATENT DOCUMENTS

| | | | | |
|---|---|---|---|---|
| 4,507,146 A | 3/1985 | Tobler et al. | ................... | 71/92 |
| 4,983,608 A | 1/1991 | Effland et al. | ............... | 514/256 |
| 5,521,184 A | 5/1996 | Zimmermann | ............... | 514/252 |
| 5,753,663 A | 5/1998 | Flippin et al. | ............... | 514/257 |
| 5,863,924 A | 1/1999 | Berger et al. | ................ | 514/275 |
| 6,297,258 B1 | 10/2001 | Wissner et al. | ............. | 514/313 |
| 6,600,037 B1 | 7/2003 | Davis et al. | ................... | 544/60 |
| 2003/0162802 A1 | 8/2003 | Guo et al. | ................... | 514/269 |
| 2003/0171359 A1 | 9/2003 | Dahmann et al. | ....... | 514/217.06 |
| 2003/0181474 A1 | 9/2003 | Pease et al. | ................ | 514/269 |
| 2004/0220177 A1* | 11/2004 | Kath et al. | ............. | 514/214.03 |
| 2005/0009853 A1* | 1/2005 | Kath et al. | ................... | 514/275 |

FOREIGN PATENT DOCUMENTS

| | | |
|---|---|---|
| DE | 4029650 | 3/1992 |
| EP | 542079 | 7/1997 |
| EP | 553016 | 7/1997 |
| WO | 9310086 | 5/1993 |
| WO | 9324467 | 12/1993 |
| WO | 9712880 | 4/1997 |
| WO | 9719065 | 5/1997 |
| WO | 9805661 | 2/1998 |
| WO | 9809961 | 3/1998 |
| WO | 9837079 | 8/1998 |
| WO | 9909016 | 2/1999 |
| WO | 9941253 | 8/1999 |
| WO | 00012485 | 3/2000 |
| WO | 00018740 | 4/2000 |
| WO | 00039101 | 7/2000 |
| WO | 01021597 | 3/2001 |
| WO | 01060816 | 8/2001 |
| WO | 01068186 | 9/2001 |
| WO | 01072744 | 10/2001 |
| WO | 02008193 | 1/2002 |
| WO | 02012227 | 2/2002 |
| WO | 02012228 | 2/2002 |
| WO | 02016348 | 2/2002 |
| WO | 02016352 | 2/2002 |
| WO | 02020501 | 3/2002 |
| WO | 02059110 | 8/2002 |
| WO | 02096887 | 12/2002 |
| WO | 02096888 | 12/2002 |
| WO | 03018021 | 3/2003 |
| WO | 03020276 | 3/2003 |
| WO | 03030909 | 4/2003 |
| WO | 03032997 | 4/2003 |
| WO | 03063794 | 8/2003 |
| WO | 03066575 | 8/2003 |
| WO | 03078404 | 9/2003 |
| WO | 03095448 | 11/2003 |
| WO | 04046118 | 6/2004 |

(Continued)

OTHER PUBLICATIONS

Cecil Textbook of Medicine, edited by Bennet, J.C., and Plum F., 20th edition, vol. 1, 1004-1010, 1996.*

(Continued)

*Primary Examiner*—Venkataraman Balasubramanian
(74) *Attorney, Agent, or Firm*—Steve Zelson; Pamela C. Ancona

(57) ABSTRACT

The present invention relates to a compound of the formula 1

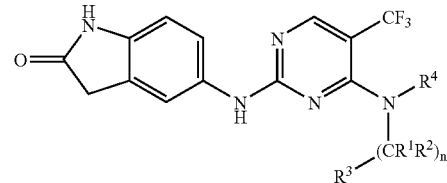

wherein $R^1$–$R^4$ are as defined herein. Such novel pyrimidine derivatives are useful in the treatment of abnormal cell growth, such as cancer, in mammals. This invention also relates to a method of using such compounds in the treatment of abnormal cell growth in mammals, especially humans, and to pharmaceutical compositions containing such compounds.

1 Claim, No Drawings

FOREIGN PATENT DOCUMENTS

| | | |
|---|---|---|
| WO | 04056786 | 7/2004 |
| WO | 04056807 | 7/2004 |

OTHER PUBLICATIONS

Wolft Manfred E. "Burger's Medicinal Chemistry, 5ed, Part 1", John Wiley & Sons, 1995, pp. 975-977.*

Banker, G.S. et al, "Modern Pharmaceutices, 3ed.", Marcel Dekker, New York. 1996, pp. 451 and 596.*

West, Anthony R., Solid State Chemistry and its Applications, Wiley, New York, 1988, pp. 358 & 365.*

Vippagunta et al., Advanced Drug Delivery Reviews 48: 3-26, 2001.*

Mass, R. D., Int. J. Radiation Oncology Bio. Phys.vol. 58(3): 932-940, 2004.*

Fabbro et al. Pharmacology & therapeutics 93, 79-98, 2002.*

Diringer et al., Journal of Medicinal Chemistry, vol. 13, No. 1, pp. 151-152 (1970).

Stover et al., Current Opinion in Drug Discovery and Development, Current Drugs, London, GB, vol. 2, No. 4, pp. 274-285 (1999).

Kath, J. C., Expert Opinion on Therapeutic Patents, vol. 10, No. 6, pp. 803-818 (2000).

Bramson et al., Journal of Medicinal Chemistry, vol. 44(25), pp. 4339-4358 (2001).

Knockaert et al., Biochemical Pharmacology, vol. 64(5-6), pp. 819-825 (2002).

Supuran et al., Expert Opin. Ther. Patents, vol. 14, No. 1, pp. 35-53 (2004).

* cited by examiner

PYRIMIDINE DERIVATIVES FOR THE TREATMENT OF ABNORMAL CELL GROWTH

CROSS-REFERENCE TO RELATED APPLICATIONS

Reference is made to U.S. Patent Application Ser. No. 60/435,670, filed Dec. 20, 2002 and U.S. Patent Application Ser. No. 60/500,742, filed Sep. 5, 2003. Reference is also made to U.S. Application Ser. No. 60/571,312, filed May 14, 2004, the disclosure of which is incorporated herein by reference in its entirety.

BACKGROUND OF THE INVENTION

This invention relates to novel pyrimidine derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma that expresses epidermal growth factor receptor tyrosine kinase (EGFR) but is without effect on the growth of another carcinoma that does not express the EGF receptor. Thus, selective inhibitors of certain receptor tyrosine kinases, are useful in the treatment of abnormal cell growth, in particular cancer, in mammals. In addition to receptor tyrosine kinses, selective inhibitors of certain non-receptor tyrosine kinases, such as FAK (focal adhesion kinase), lck, src, abl or serine/threonine kinases (e.g., cyclin dependent kinases), are useful in the treatment of abnormal cell growth, in particular cancer, in mammals. FAK is also known as the Protein-Tyrosine Kinase 2, PTK2.

Convincing evidence suggests that FAK, a cytoplasmic, non-receptor tyrosine kinase, plays an essential role in cell-matrix signal transduction pathways (Clark and Brugge 1995, *Science* 268: 233–239) and its aberrant activation is associated with an increase in the metastatic potential of tumors (Owens et al. 1995, *Cancer Research* 55: 2752–2755). FAK was originally identified as a 125 kDa protein highly tyrosine-phosphorylated in cells transformed by v-Src. FAK was subsequently found to be a tyrosine kinase that localizes to focal adhesions, which are contact points between cultured cells and their underlying substratum and sites of intense tyrosine phosphorylation. FAK is phosphorylated and, thus, activated in response to extracellular matrix (ECM)-binding to integrins. Recently, studies have demonstrated that an increase in FAK mRNA levels accompanied invasive transformation of tumors and attenuation of the expression of FAK (through the use of antisense oligonucleotides) induces apoptosis in tumor cells (Xu et al. 1996, *Cell Growth and Diff.* 7: 413–418). In addition to being expressed in most tissue types, FAK is found at elevated levels in most human cancers, particularly in highly invasive metastases.

Various compounds, such as styrene derivatives, have also been shown to possess tyrosine kinase inhibitory properties. Five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties.

Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. In addition, the following list of publications relate to bis-mono and bicyclic aryl and heteroaryl compounds that may optionally be used as tyrosine kinase inhibitors: WO 03/030909, WO 03/032997, U.S. Patent Application No. 2003/0181474, U.S. Patent Application No. 2003/0162802, U.S. Pat. No. 5,863, 924, WO 03/078404, U.S. Pat. No. 4,507146, WO 99/41253, WO 01/72744, WO 02/48133, U.S. Patent Application No. 2002/156087, WO 02/102783, and WO 03/063794.

U.S. patent application Ser. No. 10/734,039, filed Dec. 11, 2003 relates to a broad class of novel pyrimidine derivatives that are kinase inhibitors, and more specifically, inhibitors of FAK. Moreover, U.S. patent application Ser. No. 10/733, 215, filed Dec. 11, 2003 relate more specifically to a subset of pyrimidine derivatives, i.e., those bearing a 5-aminooxindole, which are tyrosine kinase inhibitors, and more particularly, FAK inhibitors. Compounds such as these are useful in the treatment of abnormal cell growth.

Accordingly, a need exists for additional selective inhibitors of certain receptor and non-receptor tyrosine kinases, useful in the treatment of abnormal cell growth, such as cancer, in mammals. The present invention provides novel pyrimidine derivatives that are kinase inhibitors and inhibitors of the non-receptor tyrosine kinase, FAK, and are useful in the treatment of abnormal cell growth.

SUMMARY OF THE INVENTION

Thus, the present invention provides a compound of the formula 1

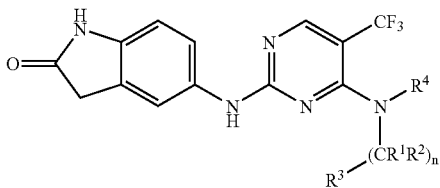

1 or a pharmaceutically acceptable salt, solvate, hydrate, or prodrug thereof, wherein n is an integer from 1 to 3;

each $R^1$ is a substituent independently selected from the group consisting of hydrogen, hydroxy, —($C_1$–$C_6$)alkyl, —($C_3$–$C_7$)cycloalkyl, —($C_2$–$C_9$)heterocyclyl, —O($C_1$–$C_6$)alkyl, —O($C_3$–$C_7$)cycloalkyl, —O($C_2$–$C_9$)heterocyclyl, —$NR^5R^6$, —$SR^7$, —$SOR^7$, —$SO_2R^7$, —$CO_2R^{12}$, —$CONR^5R^6$, —$SO_2NR^5R^6$, —$NHCOR^{12}$, —$NR^{12}CONR^5R^6$, and —$NR^{12}SO_2R^7$; wherein said $R^1$ substituents, —($C_1$–$C_6$)alkyl, —($C_3$–$C_7$)cycloalkyl, —($C_2$–$C_9$)heterocyclyl, —O($C_1$–$C_6$)alkyl, —O($C_3$–$C_7$)cycloalkyl, —O($C_2$–$C_9$)heterocyclyl, —$NR^5R^6$, —$SR^7$, —$SOR^7$, —$SO_2R^7$, —$CO_2R^{12}$, —$CONR^5R^6$, —$SO_2NR^5R^6$, —$NHCOR^{12}$, —$NR^{12}CONR^5R^6$, and —$NR^{12}SO_2R^7$, are optionally substituted by one to three moieties independently selected from the group consisting of hydrogen, halogen, hydroxy, —$CF_3$, —CN, —($C_1$–$C_6$)alkyl, —$NR^5R^6$, —$OR^{12}$, —($C_3$–$C_7$)cycloalkyl, —($C_2$–$C_9$)heterocyclyl, —$CO_2R^{12}$, —$CONR^5R^6$ and —$CONR^5R^8$;

each $R^2$ is a substituent independently selected from the group consisting of hydrogen, —($C_1$–$C_6$)alkyl, —($C_2$–$C_6$)alkenyl, —($C_2$–$C_6$)alkynyl, —($C_3$–$C_7$)cycloalkyl, —($C_2$–$C_9$)heterocyclyl, —$CO_2R^{12}$, and —$CONR^5R^6$; wherein said $R^2$ substituents, —($C_1$–$C_6$)alkyl, —($C_2$–$C_6$)alkenyl, —($C_2$–$C_6$)alkynyl, —($C_3$–$C_7$)cycloalkyl, —($C_2$–$C_9$)heterocyclyl, —$CO_2R^{12}$, and —$CONR^5R^6$, are optionally substituted by one to three moieties independently selected from the group consisting of hydrogen, halogen, hydroxy, —$CF_3$, —$NO_2$, —CN, —($C_1$–$C_6$)alkyl, —($C_2$–$C_6$)alkenyl, —($C_2$–$C_6$)alkynyl, —C=N—OH, —C=N—O(($C_1$–$C_6$)alkyl), —$NR^5R^6$, —$OR^{12}$, —($C_3$–$C_7$)cycloalkyl, —($C_2$–$C_9$)heterocyclyl, —$CO_2R^{12}$, —$CONR^5R^6$, —$CONR^5R^6$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —($C_2$–$C_6$)alkenyl and —($C_2$–$C_6$)alkynyl $R^2$ moieties may be optionally substituted by one to three $R^{12}$ groups;

$R^1$ and $R^2$ may be taken together with the atom(s) to which they are attached to form a cyclic group, —($C_3$–$C_{10}$)cycloalkyl or —($C_2$–$C_9$)heterocyclyl, wherein said cyclic group is optionally substituted by one to three moieties independently selected from the group consisting of hydrogen, halogen, hydroxy, —$CF_3$, —$NO_2$, —CN, —($C_1$–$C_6$)alkyl, —($C_2$–$C_6$)alkenyl, —($C_2$–$C_6$)alkynyl, —C=N—OH, —C=N—O(($C_1$–$C_6$)alkyl), —$NR^5R^6$, —$OR^{12}$, —($C_3$–$C_7$)cycloalkyl, —($C_2$–$C_9$)heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —($C_2$–$C_6$)alkenyl and —($C_2$–$C_6$)alkynyl moieties of said cyclic group may be optionally substituted by one to three $R^{12}$ groups, and said cyclic group is optionally interrupted by one to three elements selected from the group consisting of —(C=O), —$SO_2$, —S—, —O—, —N—, —NH— and —$NR^{12}$;

$R^3$ is a substituent selected from the group consisting of:

(a) hydrogen;

(b) —($C_6$–$C_{10}$)aryl or —($C_1$–$C_9$)heteroaryl, optionally substituted by one to three moieties independently selected from the group consisting of halogen, hydroxy, —($C_1$–$C_6$)alkyl, —($C_1$–$C_6$)alkyl-P(O)(O($C_1$–$C_6$)alkyl)$_2$, —($C_3$–$C_{10}$)cycloalkyl, ($C_6$–$C_{10}$)aryl, ($C_2$–$C_9$)heterocyclyl, —($C_1$–$C_9$)heteroaryl, —$NR^5R^5$, —$NHSO_2$($C_1$–$C_6$)alkyl, —$NHSO_2$($C_3$–$C_6$)cycloalkyl, —N(($C_1$–$C_6$)alkyl)($SO_2$—$C_1$–$C_6$)alkyl), —N(($C_1$–$C_6$)alkyl)($SO_2$ ($C_3$–$C_6$)cycloalkyl), —N(($C_3$–$C_6$)cycloalkyl)($SO_2$—$C_1$–$C_6$)alkyl), —N(($C_3$–$C_6$)cycloalkyl)($SO_2$($C_3$–$C_6$) cycloalkyl), —O($C_1$–$C_6$)alkyl, —O—$SO_2$($C_1$–$C_6$)alkyl, —O—$SO_2$($C_3$–$C_6$)cycloalkyl, —(CO)($C_1$–$C_6$)alkyl, —(CO)$CF_3$, —(CO)($C_3$–$C_{10}$)cycloalkyl, —(CO) ($C_6$–$C_{10}$)aryl, —(CO)($C_2$–$C_9$)heterocyclyl, —(CO) ($C_1$–$C_9$)heteroaryl, —(CO)O($C_1$–$C_6$)alkyl, —(CO)O ($C_3$–$C_{10}$)cycloalkyl, —(CO)O($C_6$–$C_{10}$)aryl, —(CO)O ($C_2$–$C_9$)heterocyclyl, —(CO)O($C_1$–$C_9$)heteroaryl, —(CO)($C_1$–$C_6$)alkyl-O($C_1$–$C_6$)alkyl, —$SO_2$($C_1$–$C_6$) alkyl, —$SO_2$($C_3$–$C_6$)cycloalkyl, —$SO_2CF_3$, —$SO_2NH_2$, —$SO_2NH$($C_1$–$C_6$)alkyl, —$SO_2NH$ ($C_3$–$C_6$)cycloalkyl, —$SO_2N$ (($C_1$–$C_6$)alkyl)$_2$, —$SO_2N$ (($C_1$–$C_6$)alkyl)(($C_3$–$C_6$)cycloalkyl), —$SO_2N$(($C_3$–$C_6$) cycloalkyl)$_2$ and —$SO_2NR^5R^6$, wherein said —($C_6$–$C_{10}$)aryl or —($C_1$–$C_9$)heteroaryl are optionally interrupted by one to three elements selected from the group consisting of —S—, —O—, —N—, —NH— and —$NR^{12}$;

(c) —($C_3$–$C_{10}$)cycloalkyl, —($C_2$–$C_9$)heterocyclyl, and —($C_1$–$C_6$)alkyl-($C_2$–$C_9$)heterocyclyl, optionally substituted by one to three moieties independently selected from the group consisting of halogen, hydroxy, —($C_1$–$C_6$)alkyl, —($C_1$–$C_6$)alkyl-P(O)(O($C_1$–$C_6$)alkyl)$_2$, —($C_3$–$C_{10}$)cycloalkyl, —($C_6$–$C_{10}$)aryl, —($C_2$–$C_9$)heterocyclyl, —($C_1$–$C_9$)heteroaryl, —$NR^5R^6$, —$NSO_2$($C_1$–$C_6$)alkyl, —$NHSO_2$($C_3$–$C_6$)cycloalkyl, —N(($C_1$–$C_6$)alkyl) ($SO_2$—$C_1$–$C_6$)alkyl), —N(($C_1$–$C_6$)alkyl)($SO_2$($C_3$–$C_6$) cycloalkyl), —N(($C_3$–$C_6$)cycloalkyl)($SO_2$—$C_1$–$C_6$) alkyl), —N(($C_3$–$C_6$)cycloalkyl)($SO_2$($C_3$–$C_6$) cycloalkyl), —O($C_1$–$C_6$)alkyl, —O—$SO_2$($C_1$–$C_6$) alkyl, —O—$SO_2$($C_1$–$C_6$)alkyl, —O—$SO_2$($C_3$–$C_6$) cycloalkyl, —(CO)($C_1$–$C_6$)alkyl, —(CO)$CF_3$, —(CO) ($C_3$–$C_{10}$)cycloalkyl, —(CO)($C_6$–$C_{10}$)aryl, —(CO) ($C_2$–$C_9$)heterocyclyl, —(CO)($C_1$–$C_9$)heteroaryl, —(CO)O($C_1$–$C_6$)alkyl, —(CO)O($C_3$–$C_{10}$)cycloalkyl, —(CO)O($C_6$–$C_{10}$)aryl, —(CO)O($C_2$–$C_9$)heterocyclyl, —(CO)O($C_1$–$C_9$)heteroaryl, —(CO)($C_1$–$C_6$)alkyl-O ($C_1$–$C_6$)alkyl, —$SO_2$($C_1$–$C_6$)alkyl, —$SO_2$($C_3$–$C_6$)cycloalkyl, —$SO_2CF_3$, —$SO_2NH_2$, —$SO_2NH$($C_1$–$C_6$) alkyl, —$SO_2NH$($C_3$–$C_6$)cycloalkyl, —$SO_2N$ (($C_1$–$C_6$) alkyl)$_2$, —$SO_2N$(($C_1$–$C_6$)alkyl)(($C_3$–$C_6$)cycloalkyl), —$SO_2N$(($C_3$–$C_6$)cycloalkyl)$_2$ and —$SO_2NR^5R^6$, wherein said —($C_3$–$C_{10}$)cycloalkyl, —($C_2$–$C_9$)heterocyclyl, and —($C_1$–$C_6$)alkyl-($C_2$–$C_9$)heterocyclyl are optionally interrupted by one to three elements selected from the group consisting of —(C=O), —$SO_2$, —S—, —O—, —N—, —NH— and —$NR^{12}$;

(d) —($C_1$–$C_6$)alkyl optionally substituted by one to three moieties selected from the group consisting of halogen, hydroxy, —($C_1$–$C_6$)alkyl, —($C_1$–$C_6$)alkyl-P(O)(O $(C_1-C_6)$alkyl)$_2$, —$(C_3-C_{10})$cycloalkyl, —$(C_6-C_{10})$aryl, —$(C_2-C_9)$heterocyclyl, —$(C_1-C_9)$heteroaryl, —$NR^5R^6$, —$NHSO_2(C_1-C_6)$alkyl, —$NHSO_2(C_3-C_6)$cycloalkyl, —$N((C_1-C_6)$alkyl)$(SO_2-C_1-C_6)$alkyl), —$N((C_1-C_6)$alkyl)$(SO_2(C_3-C_6)$cycloalkyl), —$N((C_3-C_6)$cycloalkyl)$(SO_2-C_1-C_6)$alkyl), —$N((C_3-C_6)$cycloalkyl)$(SO_2(C_3-C_6)$cycloalkyl), —$O(C_1-C_6)$alkyl, —O—$SO_2(C_1-C_6)$alkyl, —O—$SO_2$ $(C_3-C_6)$cycloalkyl, —(CO)$(C_1-C_6)$alkyl, —(CO)$CF_3$, —(CO)$(C_3-C_{10})$cycloalkyl, —(CO)$(C_6-C_{10})$aryl, —(CO)$(C_2-C_9)$heterocyclyl, —(CO)$(C_1-C_9)$heteroaryl, —(CO)$O(C_1-C_6)$alkyl, —(CO)$O(C_3-C_{10})$cycloalkyl, —(CO)$O(C_6-C_{10})$aryl, —(CO)$O(C_2-C_9)$heterocyclyl, —(CO)$O(C_1-C_9)$heteroaryl, —(CO)$(C_1-C_6)$alkyl-$O(C_1-C_6)$alkyl, —$SO_2(C_1-C_6)$alkyl, —$SO_2(C_3-C_6)$cycloalkyl, —$SO_2CF_3$, —$SO_2NH_2$, —$SO_2NH(C_1-C_6)$alkyl, —$SO_2NH(C_3-C_6)$cycloalkyl, —$SO_2N((C_1-C_6)$alkyl)$_2$, —$SO_2N((C_1-C_6)$alkyl)$((C_3-C_6)$cycloalkyl), —$SO_2N((C_3-C_6)$cycloalkyl)$_2$ and —$SO_2NR^5R^6$, wherein said —$(C_1-C_6)$alkyl is optionally interrupted by one to three elements selected from the group consisting of —(C=O), —$SO_2$, —S—, —O—, —N—, —NH— and —$NR^{12}$;

and wherein each $R^3$ (b)–(d) substituent, moiety, or element is optionally substituted by one to three radicals independently selected from the group consisting of hydrogen, halogen, hydroxy, —$CF_3$, —$NO_2$, —CN, —$(C_1-C_6)$alkyl, —$(C_2-C_6)$alkenyl, —$(C_2-C_6)$alkynyl, —$(C_3-C_7)$cycloalkyl, —$(C_2-C_9)$heterocyclyl, —$(C_6-C_{10})$aryl, —$(C_1-C_9)$heteroaryl, —$O(C_1-C_6)$alkyl, —$O(C_3-C_7)$cycloalkyl, —$O(C_2-C_9)$heterocyclyl, —C=N—OH, —C=N—$O(C_1-C_6$ alkyl), —$NR^5R^6$, —$SR^7$, —$SOR^7$, —$SO_2R^7$, —$CO_2R^{12}$, —$CONR^5R^6$, —$SO_2NR^5R^6$, —$NHCOR^5$, —$NR^{12}CONR^5R^6$, and —$NR^{12}SO_2R^7$;

$R^4$ is a substituent selected from the group consisting of hydrogen, —$(C_1-C_6)$alkyl, —$(C_3-C_7)$cycloalkyl, and —$(C_2-C_9)$heterocyclyl; wherein said —$(C_1-C_6)$alkyl, —$(C_3-C_7)$cycloalkyl, and —$(C_2-C_9)$heterocyclyl $R^4$ substituents are optionally substituted by one to three moieties independently selected from the group consisting of hydrogen, halogen, hydroxyl, —$(C_1-C_6)$alkyl, —CN, —$NR^5R^6$, —$OR^5$, —$(C_3-C_7)$cycloalkyl, —$(C_2-C_9)$heterocyclyl, —$CO_2R^{12}$, —$SO_2NR^5R^6$, —$NR^{12}SO_2R^7$, —$SO_2R^7$ and —$CONR^5R^8$; wherein $R^5$ and $R^8$ of said —$CONR^5R^8$ group m taken together with the atoms to which they are attached to form a —$(C_2-C_9)$heterocyclyl;

$R^5$ and $R^6$ are each substituents independently selected from the group consisting of hydrogen, —$(C_1-C_6)$alkyl, —$(C_3-C_7)$cycloalkyl, —$(C_2-C_9)$heterocyclyl, —$(C_6-C_{10})$aryl, —$(C_1-C_9)$heteroaryl, —$COR^{12}$ and —$SO_2R^{12}$; wherein said —$(C_1-C_6)$alkyl, —$(C_3-C_7)$cycloalkyl, —$(C_2-C_9)$heterocyclyl, —$(C_6-C_{10})$aryl, —$(C_1-C_9)$heteroaryl, —$COR^{12}$ and —$SO_2R^{12}R^5$ or $R^6$ substituents are optionally substituted by one to three moieties independently selected from the group consisting of hydrogen, halogen, —$CF_3$, —CN, —$(C_1-C_6)$alkyl, —$NH(C_1-C_6)$alkyl, —$NH(C_3-C_7)$cycloalkyl, —$NH(C_2-C_9)$heterocyclyl, —$NH(C_6-C_{10})$aryl, —$NH(C_1-C_9)$heteroaryl, —$N((C_1-C_6)$alkyl)$_2$, —$N((C_3-C_7)$cycloalkyl)$_2$, —$N((C_2-C_9)$heterocyclyl)$_2$, —$N((C_6-C_{10})$aryl)$_2$, —$N((C_1-C_9)$heteroaryl)$_2$, —$O(C_1-C_6)$alkyl, —$O(C_3-C_7)$cycloalkyl, —$O(C_2-C_9)$heterocyclyl, —$O(C_6-C_{10})$aryl, —$O(C_1-C_9)$heteroaryl, —$(C_3-C_7)$cycloalkyl, —$(C_2-C_9)$heterocyclyl, —$CO_2R^7$, $SO_2NR^5R^6$, $NR^{12}SO_2R^7$, —$SO_2R^7$, —$CONH_2$, —$CONHR^7$, and —$CONR^7R^8$; wherein $R^7$ and $R^8$ of said —$CONR^7R^8$ group may be taken together with the nitrogen atom to which they are attached to form a —$(C_2-C_9)$heterocyclyl;

$R^5$ and $R^6$ may be taken together with the atom(s) to which they are attached to form a —$(C_2-C_9)$heterocyclyl, wherein said —$(C_2-C_9)$heterocyclyl group is optionally substituted by one to three moieties selected from the group consisting of hydrogen, halogen, hydroxy, —$CF_3$, —$NO_2$, —CN, —$(C_1-C_6)$alkyl, —$(C_2-C_6)$alkenyl, —$(C_2-C_6)$alkynyl, —C=N—OH, —C=N—$O((C_1-C_6)$alkyl), —$NR^7R^8$, —$OR^{12}$, —$(C_3-C_7)$cycloalkyl, —$(C_2-C_9)$heterocyclyl, —$CO_2R^{12}$, $CONR^7R^8$, —$CONR^5R^8$, —$SR^7$, —$SOR^7$, —$SO_2R^7$, —$SO_2NR^7R^8$, —$NHCOR^{12}$, —$NR^{12}CONR^7R^8$, and —$NR^{12}SO_2R^7$, wherein said —$(C_2-C_6)$alkenyl and —$(C_2-C_6)$alkynyl moieties of said —$(C_2-C_9)$heterocyclyl group may be optionally substituted by one to three $R^7$ groups, and said $(C_2-C_9)$heterocyclyl group is optionally interrupted by one to three elements selected from the group consisting of —(C=O), —$SO_2$, —S—, —O—, —N—, —NH— and —$NR^{12}$;

$R^7$ is a substituent selected from the group consisting of —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl; wherein said —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl $R^7$ substituents are optionally substituted by one to three moieties independently selected from the group consisting of hydrogen, halogen, hydroxy, —CN, —$(C_1-C_6)$alkyl, —$NR^{12}$, and —$O(C_1-C_6)$alkyl;

$R^3$ is a substituent selected from the group consisting of hydrogen, —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl; wherein said —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl $R^8$ substituents are optionally substituted by one to three moieties independently selected from the group consisting of hydrogen, halogen, hydroxy, —CN, —$(C_1-C_6)$alkyl, —$NH_2$, —$NHR^9$, —$NR^9_2$, $OR^9$, —$(C_3-C_7)$cycloalkyl, —$(C_2-C_9)$heterocyclyl, —$CO_2R^{10}$, —$CONH_2$, —$CONHR^{10}$, and —$CONR^{10}R^{11}$; wherein $R^{10}$ and $R^{11}$ of —$CONR^{10}R^{11}$ may be taken together with the nitrogen atom to which they are attached to form a —$(C_2-C_9)$heterocyclyl;

$R^9$ and $R^{10}$ are each —$(C_1-C_6)$alkyl;

$R^{11}$ is hydrogen or —$(C_1-C_6)$alkyl; and $R^{12}$ is a substituent selected from the group consisting of hydrogen, —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl; wherein said —$(C_1-C_6)$alkyl, —$(C_3-C_7)$cycloalkyl, —$(C_2-C_9)$heterocyclyl, —$(C_6-C_{10})$aryl, and —$(C_1-C_9)$heteroaryl $R^{12}$ substituent is optionally substituted by one to three moieties independently selected from the group consisting of hydrogen, halogen, —$CF_3$, —CN, —$(C_1-C_6)$alkyl, —$NH(C_1-C_6)$alkyl, —$NH(C_3-C_7)$cycloalkyl, —$NH(C_2-C_9)$heterocyclyl, —$NH(C_6-C_{10})$aryl, —$NH(C_1-C_9)$heteroaryl, —$N((C_1-C_6)$alkyl)$_2$, —$N((C_3-C_7)$cycloalkyl)$_2$, —$N((C_2-C_9)$heterocyclyl)$_2$, —$N((C_6-C_{10})$aryl)$_2$, —$N((C_1-C_9)$heteroaryl)$_2$, —$O(C_1-C_6)$alkyl, —$O(C_3-C_7)$cycloalkyl, —$O(C_2-C_9)$heterocyclyl, —$O(C_6-C_{10})$aryl, —$O(C_1-C_9)$heteroaryl, —$(C_3-C_7)$cycloalkyl, —$(C_2-C_9)$heterocyclyl, —$CO_2R^7$, —$CONH_2$, —$CONHR^7$, and —$CONR^7R^8$; wherein $R^7$ and $R^8$ of said —$CONR^7R^8$ group may be taken together with the atoms to which they are attached to form a —$(C_2-C_9)$heterocyclyl.

The present invention also includes isotopically-labeled compounds, which are identical to those recited in Formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labelled compounds of Formula 1 of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

The present invention also relates to the pharmaceutically acceptable acid addition salts of compounds of the formula 1. The acids which are used to prepare the pharmaceutically acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula 1. The chemical bases that may be used as reagents to prepare pharmaceutically acceptable base salts of those compounds of formula 1 that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

This invention also encompasses pharmaceutical compositions containing prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula 1. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters that are covalently bonded to the above substituents of formula 1 through the carbonyl carbon prodrug sidechain.

This invention also encompasses compounds of formula 1 containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The compounds of this invention include all stereoisomers (e.g., cis and trans isomers) and all optical isomers of compounds of the formula 1 (e.g., R and S enantiomers), as well as racemic, diastereomeric and other mixtures of such isomers.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The present invention also includes atropisomers of the present invention. Atropisomers refer to compounds of formula 1 that can be separated into rotationally restricted isomers.

The compounds of this invention may contain olefin-like double bonds. When such bonds are present, the compounds of the invention exist as cis and trans configurations and as mixtures thereof.

A "suitable substituent" is intended to mean a chemically and pharmaceutically acceptable functional group i.e., a moiety that does not negate the biological activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents. Further examples of suitable substituents include those recited in the definition of compounds of Formula 1, including $R^1$ through $R^{12}$, as defined hereinabove.

The term "interrupted by" refers to compounds in which a ring carbon atom is replaced by an element selected from the group consisting of —(C=O), —$SO_2$, —S—, —O—, —N—, —NH—, and —$NR^{12}$. For example, if a substituent is —($C_6$–$C_{10}$)aryl, such as

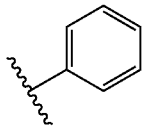

the ring may be interrupted or replaced by a nitrogen heteroatom to form the following ring:

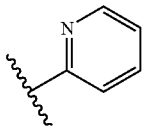

such that a ring carbon is replaced by the heteroatom nitrogen. Compounds of the invention can accommodate up to three such replacements or interruptions.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl. The phrase "each of said alkyl" as used herein refers to any of the preceding alkyl moieties within a group such alkoxy, alkenyl or alkylamino. Preferred alkyls include ($C_1$–$C_6$)alkyl, more preferred are ($C_1$–$C_4$) alkyl, and most preferred are methyl and ethyl.

As used herein, the term "cycloalkyl" refers to a mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds and optionally substituted by 1 to 3 suitable substituents as defined above such as fluoro, chloro, trifluoromethyl, ($C_1$–$C_6$) alkoxy, ($C_6$–$C_{10}$)aryloxy, trifluoromethoxy, difluoromethoxy or ($C_1$–$C_6$)alkyl.

As used herein, the term "halogen" includes fluoro, chloro, bromo or iodo or fluoride, chloride, bromide or iodide.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

As used herein, the term "alkynyl" is used herein to mean straight or branched hydrocarbon chain radicals having one triple bond including, but not limited to, ethynyl, propynyl, butynyl, and the like; optionally substituted by 1 to 3 suitable substituents as defined above such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "aryl" means aromatic radicals such as phenyl, naphthyl, tetrahydronaphthyl, indanyl and the like; optionally substituted by 1 to 3 suitable substituents as defined above.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

The term "heterocyclic" as used herein refers to a cyclic group containing 1–9 carbon atoms and 1 to 4 hetero atoms selected from N, O, S(O)$_n$ or NR. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally containing 1 or 2 double bonds and optionally substituted by 1 to 3 suitable substituents as defined above such as fluoro, chloro, trifluoromethyl, ($C_1$–$C_6$)alkoxy, ($C_6$–$C_{10}$)aryloxy, trifluoromethoxy, difluoromethoxy or ($C_1$–$C_6$)alkyl.

Nitrogen heteroatoms as used herein refers to N=, >N and —NH; wherein —N= refers to a nitrogen double bond; >N refers to a nitrogen containing two bond connections and —N refers to a nitrogen containing one bond.

"Embodiment" as used herein refers to specific groupings of compounds or uses into discrete subgenera. Such subgenera may be cognizable according to one particular substituent such as a specific $R^1$ or $R^3$ group. Other subgenera are cognizable according to combinations of various substituents, such as all compounds wherein $R^2$ is hydrogen and $R^1$ is $(C_1-C_6)$alkyl.

Therefore, the present invention provides a compound of formula 1, wherein $R^3$ is hydrogen.

The present invention also provides a compound of formula 1 wherein $R^3$ is selected from the group consisting of —$(C_6-C_{10})$aryl and —$(C_1-C_9)$heteroaryl, optionally substituted by one to three moieties independently selected from the group consisting of halogen, hydroxy, —$(C_1-C_6)$alkyl, —$(C_1-C_6)$alkyl-P(O)(O($C_1-C_6$)alkyl)$_2$, —$(C_3-C_{10})$cycloalkyl, —$(C_6-C_{10})$aryl, $(C_2-C_9)$heterocyclyl, —$(C_1-C_9)$heteroaryl, —$NR^5R^6$, —$NHSO_2(C_1-C_6)$alkyl, —$NHSO_2(C_3-C_6)$cycloalkyl, —N(($C_1-C_6$)alkyl)($SO_2-C_1-C_6$)alkyl), —N(($C_1-C_6$)alkyl)($SO_2(C_3-C_6)$cycloalkyl), —N(($C_3-C_6$)cycloalkyl)($SO_2-C_1-C_6$)alkyl), —N(($C_3-C_6$)cycloalkyl)($SO_2(C_3-C_6)$cycloalkyl), —O($C_1-C_6$)alkyl, —O—$SO_2(C_1-C_6)$alkyl, —O—$SO_2(C_3-C_6)$cycloalkyl, —(CO)($C_1-C_6$)alkyl, —(CO)$CF_3$, —(CO)($C_3-C_{10}$)cycloalkyl, —(CO)($C_6-C_{10}$)aryl, —(CO)($C_2-C_9$)heterocyclyl, —(CO)($C_1-C_9$)heteroaryl, —(CO)O($C_1-C_6$)alkyl, —(CO)O($C_3-C_{10}$)cycloalkyl, —(CO)O($C_6-C_{10}$)aryl, —(CO)O($C_2-C_9$)heterocyclyl, —(CO)O($C_1-C_9$)heteroaryl, —(CO)($C_1-C_6$)alkyl-O($C_1-C_6$)alkyl, —$SO_2(C_1-C_6)$alkyl, —$SO_2(C_3-C_6)$cycloalkyl, $SO_2CF_3$, $SO_2NH_2$, $SO_2NH(C_1-C_6)$alkyl, —$SO_2NH(C_3-C_6)$cycloalkyl, —$SO_2N((C_1-C_6)$alkyl)$_2$, $SO_2N((C_1-C_6)$alkyl)(($C_3-C_6)$cycloalkyl), —$SO_2N((C_3-C_6$cycloalkyl), —$SO_2NR^5R^6$, wherein said —$(C_6-C_{10})$aryl or —$(C_1-C_9)$heteroaryl are optionally interrupted by one to three elements selected from the group consisting of —S—, —O—, —N—, —NH— and —$NR^{12}$.

Another embodiment of the present invention is a compound of formula 1 wherein $R^3$ is selected from the group consisting of —$(C_3-C_{10})$cycloalkyl, —$(C_2-C_9)$heterocyclyl, and —$(C_1-C_6)$alkyl-$(C_2-C_9)$heterocyclyl, optionally substituted by one to three moieties independently selected from the group consisting of halogen, hydroxy, —$(C_1-C_6)$alkyl, —$(C_1-C_6)$alkyl-P(O)(O($C_1-C_6$)alkyl)$_2$, —$(C_3-C_{10})$cycloalkyl, —$(C_6-C_{10})$aryl, —$(C_2-C_9)$heterocyclyl, —$(C_1-C_9)$heteroaryl, —$NR^5R^6$, —$NSO_2(C_1-C_6)$alkyl, —$NHSO_2(C_3-C_6)$cycloalkyl, —N(($C_1-C_6$)alkyl)($SO_2-C_1-C_6$)alkyl), —N(($C_1-C_6$)alkyl)($SO_2(C_3-C_6)$cycloalkyl), —N(($C_3-C_6$)cycloalkyl)($SO_2-C_1-C_6$)alkyl), —N(($C_3-C_6$)cycloalkyl)($SO_2(C_3-C_6)$cycloalkyl), —O($C_1-C_6$)alkyl, —O—$SO_2(C_1-C_6)$alkyl, —O—$SO_2(C_1-C_6)$alkyl, —O—$SO_2(C_3-C_6)$cycloalkyl, —(CO)($C_1-C_6$)alkyl, —(CO)$CF_3$, —(CO)($C_3-C_{10}$)cycloalkyl, —(CO)($C_6-C_{10}$)aryl, —(CO)($C_2-C_9$)heterocyclyl, —(CO)($C_1-C_9$)heteroaryl, —(CO)O($C_1-C_6$)alkyl, —(CO)O($C_3-C_{10}$)cycloalkyl, —(CO)O($C_6-C_{10}$)aryl, —(CO)O($C_2-C_9$)heterocyclyl, —(CO)O($C_1-C_9$)heteroaryl, —(CO)($C_1-C_6$)alkyl-O($C_1-C_6$)alkyl, —$SO_2(C_1-C_6)$alkyl, —$SO_2(C_3-C_6)$cycloalkyl, $SO_2CF_3$, $SO_2NH_2$, $SO_2NH(C_1-C_6)$alkyl, —$SO_2NH(C_3-C_6)$cycloalkyl, —$SO_2N((C_1-C_6)$alkyl)$_2$, $SO_2N((C_1-C_6)$alkyl(($C_3-C_6)$cycloalkyl), —$SO_2N((C_3-C_6)$cycloalkyl)$_2$ and —$SO_2NR^5R^6$, wherein said —$(C_3-C_{10})$cycloalkyl, —$(C_2-C_9)$heterocyclyl, and —$(C_1-C_6)$alkyl-$(C_2-C_9)$heterocyclyl are optionally interrupted by one to three elements selected from the group consisting of —(C=O), —$SO_2$, —S—, —O—, —N—, —NH—0 and —$NR^{12}$.

A further embodiment of the invention is a compound of formula 1 wherein $R^3$ is —$(C_1-C_6)$alkyl optionally substituted by one to three moieties selected from the group consisting of halogen, hydroxy, —$(C_1-C_6)$alkyl, —$(C_1-C_6)$alkyl-P(O)(O($C_1-C_6$)alkyl)$_2$, —$(C_3-C_{10})$cycloalkyl, $(C_6-C_{10})$aryl, $(C_2-C_9)$heterocyclyl, —$(C_1-C_9)$heteroaryl, —$NR^5R^6$, —$NHSO_2(C_1-C_6)$alkyl, —$NHSO_2(C_3-C_6)$cycloalkyl, —N(($C_1-C_6$)alkyl)($SO_{21}-C_1-C_6$)alkyl), —N(($C_1-C_6$)alkyl)($SO_2(C_3-C_6)$cycloalkyl), —N(($C_3-C_6)$cycloalkyl)($SO_2-C_1-C_6$)alkyl), —N(($C_3-C_6)$cycloalkyl)($SO_2(C_3-C_6)$cycloalkyl), —O($C_1-C_6$)alkyl, —O—$SO_2(C_1-C_6)$alkyl, —O—$SO_2(C_3-C_6)$cycloalkyl, —(CO)($C_1-C_6$)alkyl, —(CO)$CF_3$, —(CO)($C_1-C_{10}$)cycloalkyl, —(CO)($C_6-C_{10}$)aryl, —(CO)($C_2-C_9$)heterocyclyl, —(CO)($C_1-C_9$)heteroaryl, —(CO)O($C_1-C_6$)alkyl, —(CO)O($C_3-C_{10}$)cycloalkyl, —(CO)O($C_6-C_{10}$)aryl, —(CO)O($C_2-C_9$)heterocyclyl, —(CO)O($C_1-C_9$)heteroaryl, —(CO)($C_1-C_6$)alkyl-O($C_1-C_6$)alkyl, —$SO_2(C_1-C_6)$alkyl, —$SO_2(C_3-C_6)$cycloalkyl, $SO_2CF_3$, $SO_2NH_2$, $SO_2NH(C_1-C_6)$alkyl, —$SO_2NH(C_3-C_6)$cycloalkyl, —$SO_2N((C_1-C_6)$alkyl)$_2$, $SO_2N((C_1-C_6)$alkyl)(($C_3-C_6)$cycloalkyl), —$SO_2N((C_3-C_6)$cycloalkyl)$_2$ and —$SO_2NR^5R^6$, wherein said —$(C_1-C_6)$alkyl is optionally interrupted by one to three elements selected from the group consisting of —(C=O), —$SO_2$, —S—, —O—, —N—, —N— and —$NR^{12}$.

Still further, the invention provides a compound of formula 2

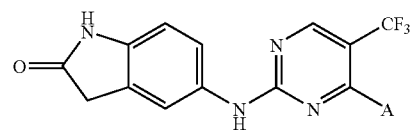

wherein A is selected from the group consisting of:

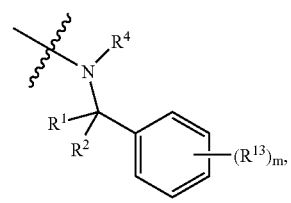

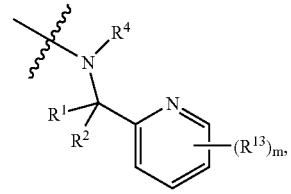

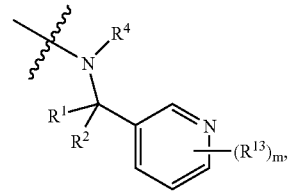

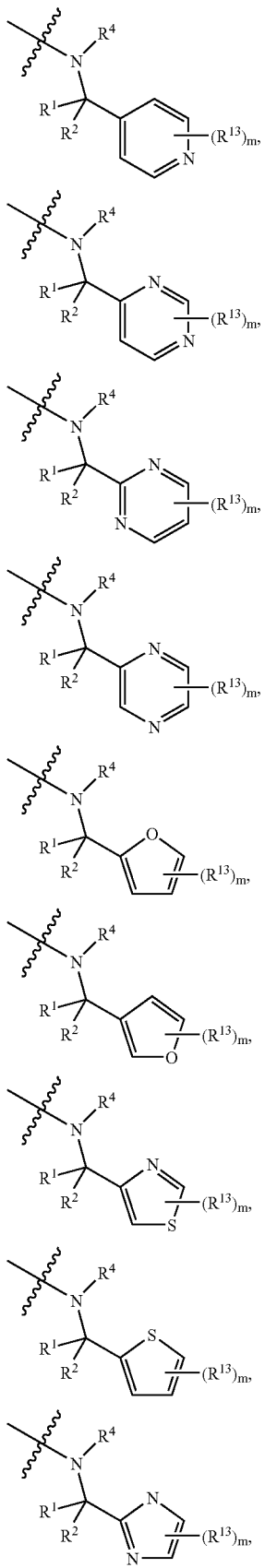

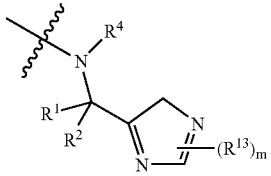

wherein m is an integer from 0 to 3 and $R^{13}$ is substituent selected from the group consisting of hydrogen, halogen, hydroxy, $(C_1-C_6)$-alkyl, $(C_3C_7)$-cycloalkyl, $(C_6-C_{10})$-aryl, $(C_1-C_9)$heteroaryl, $(C_2-C_9)$-heterocyclyl, O—$(C_1-C_6)$-alkyl, O—$(C_3-C_7)$-cycloalkyl, $SO_2$—$(C_1-C_6)$alkyl, $SO_2$($C_3-C_7$)-cycloalkyl, $NHSO_2(C_1-C_6)$alkyl, $N((C_1-C_6)$alkyl)$(SO_2(C_1-C_6$-alkyl)), $N((C_3-C_7)$cycloalkyl)$(SO_2(C_1-C_6$-alkyl)), $N(C_1-C_6$-alkyl)$(SO_2(C_3-C_7)$cycloalkyl), $N((C_3-C_7)$cycloalkyl)$(SO_2(C_3-C_7)$cycloalkyl), $OSO_2(C_1-C_6)$alkyl, $SO_2CF_3$, $SO_2NH_2$, $SO_2NH(C_1-C_6)$alkyl, $SO_2NH(C_3-C_7)$cycloalkyl, $SO_2NR^5R^6$, $SO_2N((C_1-C_6)$alkyl)$_2$, $CF_3$, CO—$(C_1-C_6)$alkyl, CO—$(C_3-C_7)$cycloalkyl, $COCF_3$, $CO_2(C_1-C_6)$alkyl,

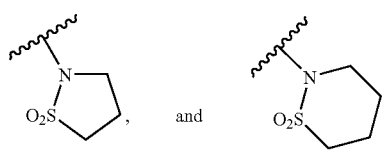

Another embodiment of the invention is a compound of the formula 3

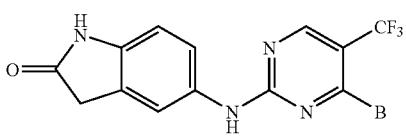

wherein B is selected from the group consisting of:

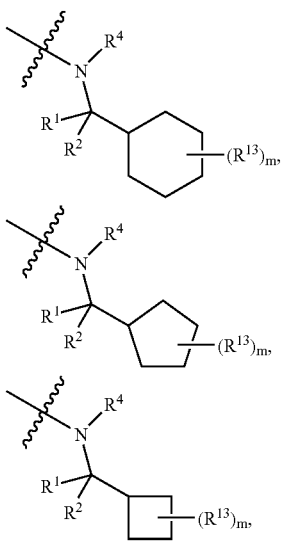

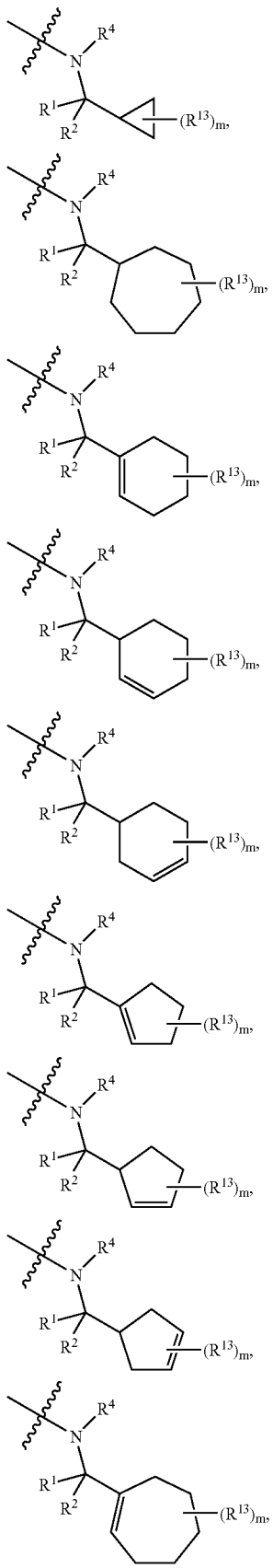
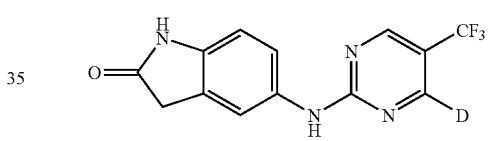
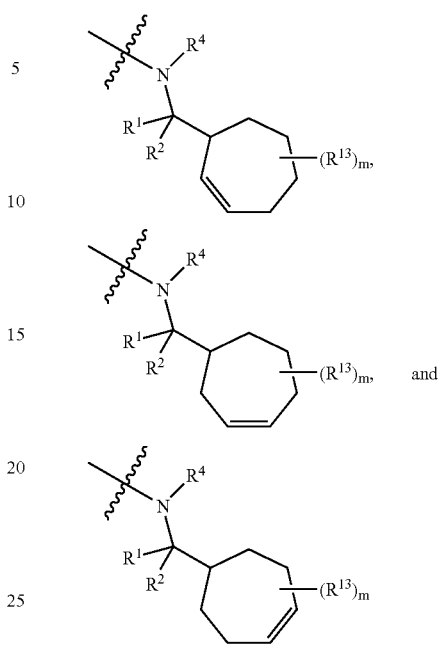
Also provided is a compound of formula 4
wherein D is selected from the group consisting of:
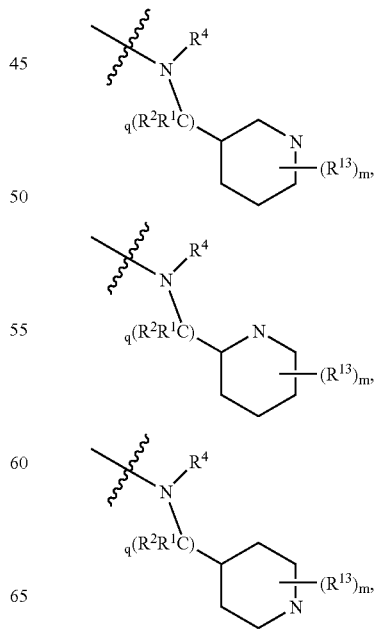

-continued
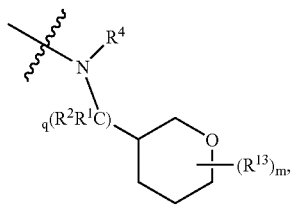
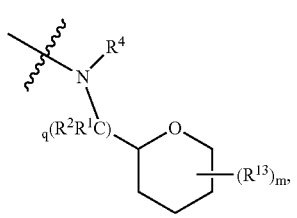
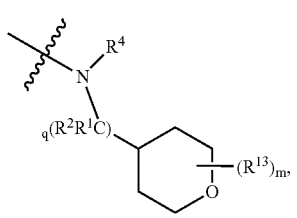
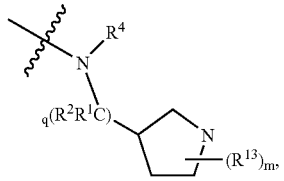
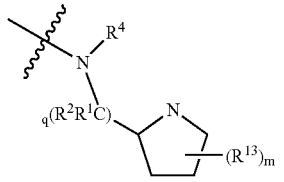
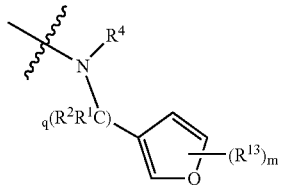
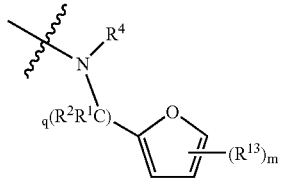
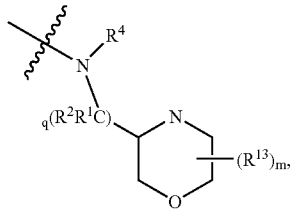
-continued
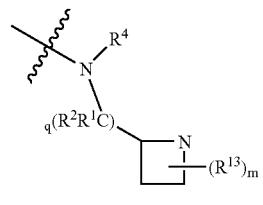
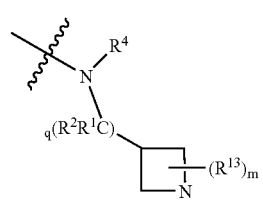
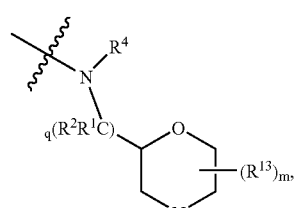
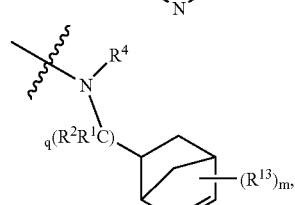
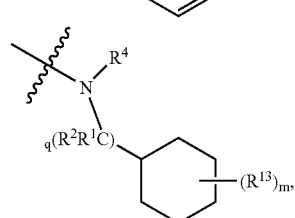
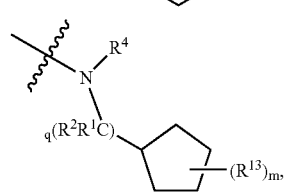
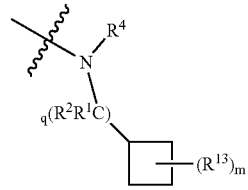
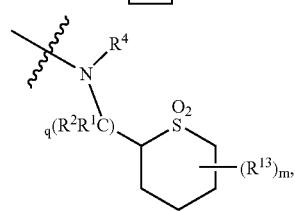

-continued

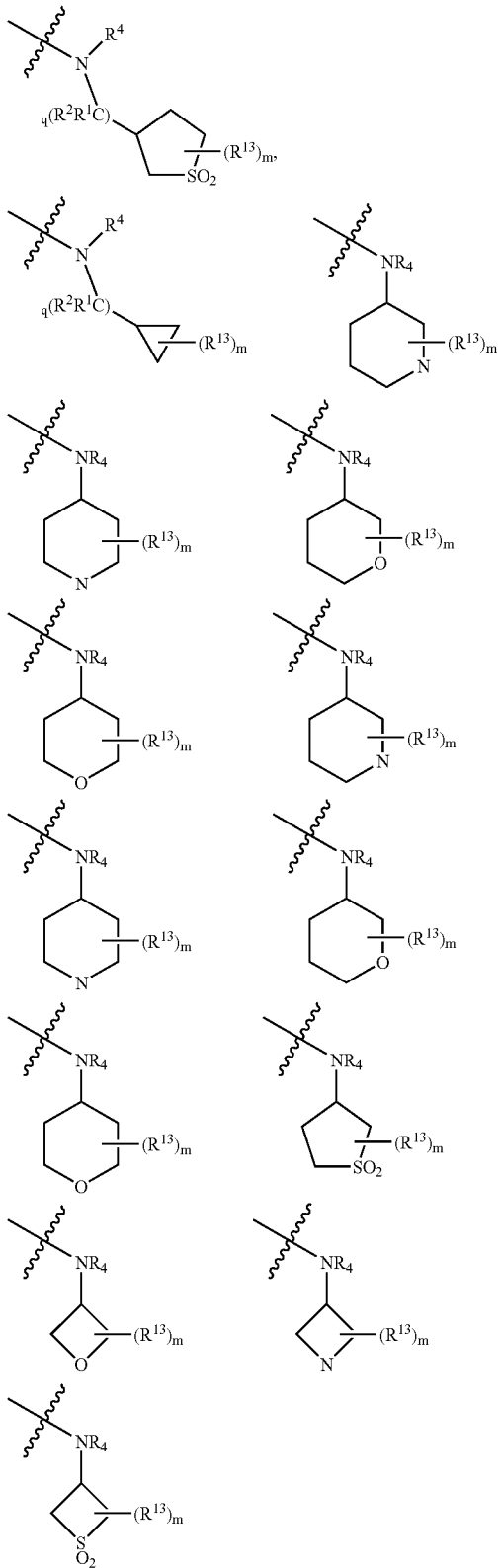

wherein q is an integer from 1 to 2.

A further embodiment of the present invention is a compound of formula 5:

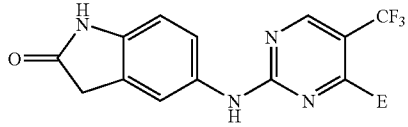

wherein E is selected from the group consisting of:

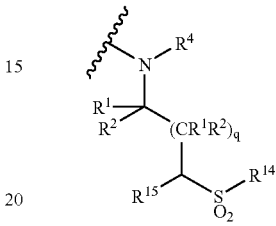

wherein $R^{14}$ is selected from the group consisting of $(C_1-C_6)$-alkyl, $(C_3-C_7)$-cycloalkyl, and $(C_2-C_9)$-heterocyclyl, and $R^{15}$ is selected from the group consisting of hydrogen, $(C_1-C_6)$-alkyl, $(C_3-C_7)$-cycloalkyl, and $(C_2-C_9)$-heterocyclyl.

Thus, the present invention provides a compound of formula 1, wherein $R^1$ is selected from hydrogen, hydroxy, and —$(C_1-C_6)$alkyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$.

The present invention further provides a compound of formula 1, wherein $R^1$ is —$(C_1-C_6)$alkyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$.

The present invention also provides a compound of formula 1 wherein $R^1$ is selected from the group consisting of —$(C_3-C_7)$cycloalkyl and —$(C_2-C_9)$heterocyclyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$.

The invention also contemplates compounds of formula 1 wherein $R^1$ is selected from —$O(C_1-C_6)$alkyl, —$O(C_3-C_7)$cycloalkyl, and —$O(C_2-C_9)$heterocyclyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^3$. In a preferred embodiment, $R^1$ is —$O(C_1-C_6)$alkyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_{10})$heterocyclyl, —$CO_2R^{12}$, —$CONR^5R^6$ and —$CONR^5R^8$.

One embodiment of the invention is a compound of formula 1 wherein $R^1$ is —$NR^5R^6$, optionally substituted by one to three moieties independently selected from the group consisting of hydrogen, halogen, hydroxy, —CN, —$(C_1-C_6)$ alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^8$ and —CONR$^5$R$^8$.

A further embodiment of the invention is a compound of formula 1 wherein R$^1$ is selected from —SR$^7$, —SOR$^7$, —SO$_2$R$^7$, and —SO$_2$NR$^5$R$^6$, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$. In a preferred embodiment, R$^1$ is —SO$_2$NR$^5$R$^6$ optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CON$^5$R$^8$.

The present invention also provides compounds of formula 1 wherein R$^1$ is —CO$_2$R$^{12}$, —CONR$^5$R$^6$, —NHCOR$_2$, —NR$^{12}$CONR$^5$R$^6$, or —NR$^{12}$SO$_2$R$^7$, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$. In a preferred embodiment, R$^1$ is —NR$^{12}$SO$_2$R$^7$, optionally substituted by one to three moieties independently selected from the group consisting of hydrogen, halogen, hydroxy, —CN, —(C$_1$–C$_6$)alkyl, —NR$^5$R$^5$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$.

Also provided is a compound of formula 1 wherein R$^2$ is hydrogen or —(C$_1$–C$_6$)alkyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^2$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups.

Further provided is a compound of formula 1 wherein R$^2$ is —(C$_3$–C$_7$)cycloalkyl, or —(C$_2$–C$_9$)heterocyclyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^2$SO$_2$R$^7$, wherein said —(C$_2$–C$_6$)alkenyl and —(C$_2$–C$_6$)alkynyl R$^2$ moieties may be optionally substituted by one to three R$^{12}$ groups.

Another embodiment of the present invention is a compound of formula 1 wherein R$^2$ is —CO$_2$R$^{12}$ and —CONR$^5$R$^6$ optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^5$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups.

Also provided is a compound of formula 1 wherein R$^1$ is selected from hydrogen, hydroxy, and —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; and R$^2$ is hydrogen or —(C$_1$–C$_6$)alkyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups.

The invention further provides a compound of formula 1 wherein R$^1$ is selected from hydrogen, hydroxy, and —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; and R$^2$ is hydrogen.

The present invention further provides a compound of formula 1, wherein R$^1$ is —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; and R$^2$ is hydrogen.

The present invention also provides a compound of formula 1 wherein R$^1$ is selected from the group consisting of —(C$_3$–C$_7$)cycloalkyl and —(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; and R$^2$ is hydrogen.

The invention also contemplates compounds of formula 1 wherein R$^1$ is selected from —O(C$_1$–C$_6$)alkyl, —O(C$_3$–C$_7$)cycloalkyl, and —O(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; and R$^2$ is hydrogen.

One embodiment of the invention is a compound of formula 1 wherein R$^1$ is —NR$^5$R$^6$, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; and R$^2$ is hydrogen.

A further embodiment of the invention is a compound of formula 1 wherein R$^1$ is selected from —SR$^7$, —SOR$^7$, —SO$_2$R$^7$, and —SO$_2$NR$^5$R$^6$ optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; and R$^2$ is hydrogen.

The present invention also provides compounds of formula 1 wherein R$^1$ is —CO$_2$R$^{12}$, —CONR$^5$R$^6$, —NHCOR$^2$, —NR$^{12}$CONR$^5$R$^6$, or —NR$^{12}$SO$_2$R$^7$, optionally substituted by one to moieties independently selected from the group consisting of hydrogen, halogen, hydroxy, —CN, —($C_1$–$C_6$) alkyl, —$NR^5R^6$, —$OR^{12}$, —($C_3$–$C_7$)cycloalkyl, —($C_2$–$C_9$) heterocyclyl, —$CO_2R^{12}$, —$CONR^5R^6$ and —$CONR^5R^8$; and $R^2$ is hydrogen.

Also provided is a compound of formula 1 wherein $R^2$ is hydrogen or —($C_1$–$C_6$)alkyl, optionally substituted by one to three moieties independently selected from the group consisting of hydrogen, halogen, hydroxy, —$NO_2$, —CN, —($C_1$–$C_6$)alkyl, —($C_2$–$C_6$)alkenyl, —($C_2$–$C_6$)alkynyl, —C=N—OH, —C=N—O(($C_1$–$C_6$)alkyl), —$NR^5R^6$, —$OR^{12}$, —($C_3$–$C_7$)cycloalkyl, —($C_2$–$C_9$)heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —($C_2$–$C_6$)alkenyl and —($C_2$–$C_6$)alkynyl $R^2$ moieties may be optionally substituted by one to three $R^1$ groups; and $R^1$ is hydrogen.

Further provided is a compound of formula 1 wherein $R^2$ is —($C_3$–$C_7$)cycloalkyl, or —($C_2$–$C_9$)heterocyclyl, optionally substituted by one to three moieties independently selected from the group consisting of hydrogen, halogen, hydroxy, —$NO_2$, —CN, —($C_1$–$C_6$)alkyl, —($C_2$–$C_6$)alkenyl, —($C_2$–$C_6$)alkynyl, —C=N—OH, —C=N—O (($C_1$–$C_6$)alkyl), —$NR^5R^6$, —$OR^{12}$, —($C_3$–$C_7$)cycloalkyl, —($C_2$–$C_9$)heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —($C_2$–$C_6$)alkenyl and —($C_2$–$C_6$)alkynyl $R^2$ moieties may be optionally substituted by one to three $R^{12}$ groups; and $R^1$ is hydrogen.

Another embodiment of the present invention is a compound of formula 1 wherein $R^2$ is —$CO_2R^{12}$ and —$CONR^5R^6$ optionally substituted by one to three moieties independently selected from the group consisting of hydrogen, halogen, hydroxy, —$NO_2$, —CN, —($C_1$–$C_6$)alkyl, —($C_2$–$C_6$)alkenyl, —($C_2$–$C_6$)alkynyl, —C=N—OH, —C=N—O(($C_1$–$C_6$)alkyl), —$NR^5R^6$, —$OR^{12}$, —($C_3$–$C_7$) cycloalkyl, —($C_2$–$C_9$)heterocyclyl, —$CO_2R^{12}$, —$CONR^5R^6$, —$CONR^5R^5$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —($C_2$–$C_6$)alkenyl and —($C_2$–$C_6$)alkynyl $R^2$ moieties may be optionally substituted by one to three $R^{12}$ groups; and $R^1$ is hydrogen.

The invention further provides a compound of formula 1 wherein $R^1$ is selected from hydrogen, hydroxy, and —($C_1$–$C_6$)alkyl, optionally substituted by one to three moieties independently selected from the group consisting of hydrogen, halogen, hydroxy, —CN, —($C_1$–$C_6$)alkyl, —$NR^5R^6$, —$OR^{12}$, —($C_3$–$C_7$)cycloalkyl, —($C_2$–$C_9$)heterocyclyl, —$CO_2R^{12}$, —$CONR^5R^6$ and —$CONR^5R^8$; and $R^2$ is —($C_1$–$C_6$)alkyl.

The present invention further provides a compound of formula 1, wherein $R^1$ is —($C_1$–$C_6$)alkyl, optionally substituted by one to three moieties independently selected from the group consisting of hydrogen, halogen, hydroxy, —CN, —($C_1$–$C_6$)alkyl, —$NR^5R^6$, —$OR^{12}$, —($C_3$–$C_7$)cycloalkyl, —($C_2$–$C_9$)heterocyclyl, —$CO_2R^{12}$, —$CONR^5R^6$ and —$CONR^5R^8$; and $R^2$ is —($C_1$–$C_6$)alkyl.

The present invention also provides a compound of formula 1 wherein $R^1$ is selected from the group consisting of —($C_3$–$C_7$)cycloalkyl and —($C_2$–$C_9$)heterocyclyl, optionally substituted by one to three moieties independently selected from the group consisting of hydrogen, halogen, hydroxy, —CN, —($C_1$–$C_6$)alkyl, —$NR^5R^6$, —$OR^{12}$, —($C_3$–$C_7$)cycloalkyl, —($C_2$–$C_9$)heterocyclyl, —$CO_2R^{12}$, —$CONR^5R^6$ and —$CONR^5R^8$; and $R^2$ is —($C_1$–$C_6$)alkyl.

The invention also contemplates compounds of formula 1 wherein $R^1$ is selected from —O($C_1$–$C_6$)alkyl, —O($C_3$–$C_7$) cycloalkyl, and —O($C_2$–$C_9$)heterocyclyl, optionally substituted by one to three moieties independently selected from the group consisting of hydrogen, halogen, hydroxy, —CN, —($C_1$–$C_6$)alkyl, —$NR^5R^6$, —$OR^{12}$, —($C_3$–$C_7$)cycloalkyl, —($C_2$–$C_9$)heterocyclyl, —$CO_2R^{12}$, —$CONR^5R^6$ and —$CONR^5R^8$; and $R^2$ is —($C_1$–$C_6$)alkyl.

One embodiment of the invention is a compound of formula 1 wherein $R^1$ is —$NR^5R^6$, optionally substituted by one to three moieties independently selected from the group consisting of hydrogen, halogen, hydroxy, —CN, —($C_1$–$C_6$) alkyl, —$NR^5R^6$, —$OR^{12}$, —($C_3$–$C_7$)cycloalkyl, —($C_2$–$C_9$) heterocyclyl, —$CO_2R^{12}$, —$CONR^5R^6$ and —$CONR^5R^8$; and $R^2$ is —($C_1$–$C_6$)alkyl.

A further embodiment of the invention is a compound of formula 1 wherein $R^1$ is selected from —$SR^7$, —$SOR^7$, —$SO_2R^7$, and —$SO_2NR^5R^6$, optionally substituted by one to three moieties independently selected from the group consisting of hydrogen, halogen, hydroxy, —CN, —($C_1$–$C_6$) alkyl, —$NR^5R^6$, —$OR^{12}$, —($C_3$–$C_7$)cycloalkyl, —($C_2$–$C_9$) heterocyclyl, —$CO_2R^{12}$, —$CONR^5R^6$ and —$CONR^5R^8$; and $R^2$ is —($C_1$–$C_6$)alkyl.

The present invention also provides compounds of formula 1 wherein $R^1$ is —$CO_2R^{12}$, —$CONR^5R^6$, —NHCOR$^{12}$, —$NR^{12}CONR^5R^6$, or —$NR^{12}SO_2R^7$, optionally substituted by one to three moieties independently selected from the group consisting of hydrogen, halogen, hydroxy, —CN, —($C_1$–$C_6$)alkyl, —$NR^5R^6$, —$OR^{12}$, —($C_3$–$C_7$)cycloalkyl, —($C_2$–$C_9$)heterocyclyl, —$CO_2R^{12}$, —$CONR^5R^6$ and —$CONR^5R^8$; and $R^2$ is —($C_1$–$C_6$)alkyl.

Also provided is a compound of formula 1 wherein $R^2$ is hydrogen or —($C_1$–$C_6$)alkyl, optionally substituted by one to three moieties independently selected from the group consisting of hydrogen, halogen, hydroxy, —$NO_2$, —CN, —($C_1$–$C_6$)alkyl, —($C_2$–$C_6$)alkenyl, —($C_2$–$C_6$)alkynyl, —C=N—OH, —C=N—O(($C_1$–$C_6$)alkyl), —$NR^5R^6$, —$OR^{12}$, —($C_3$–$C_7$)cycloalkyl, —($C_2$–$C_9$)heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —($C_2$–$C_6$)alkenyl and —($C_2$–$C_6$)alkynyl $R^2$ moieties may be optionally substituted by one to three $R^{12}$ groups; and $R^1$ is —($C_1$–$C_6$)alkyl.

Further provided is a compound of formula 1 wherein $R^2$ is —($C_3$–$C_7$)cycloalkyl, or —($C_2$–$C_9$)heterocyclyl, optionally substituted by one to three moieties independently selected from the group consisting of hydrogen, halogen, hydroxy, —$NO_2$, —CN, —($C_1$–$C_6$)alkyl, —($C_2$–$C_6$)alkenyl, —($C_2$–$C_6$)alkynyl, —C=N—OH, —C=N—O (($C_1$–$C_6$)alkyl), —$NR^5R^6$, —$OR^{12}$, —($C_3$–$C_7$)cycloalkyl, —($C_2$–$C_9$)heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —($C_2$–$C_6$)alkenyl and —($C_2$–$C_6$)alkynyl $R^2$ moieties may be optionally substituted by one to three $R^{12}$ groups; and $R^1$ is —($C_1$–$C_6$)alkyl.

Another embodiment of the present invention is a compound of formula 1 wherein $R^2$ is —$CO_2R^{12}$ and —$CONR^5R^6$ optionally substituted by one to three moieties independently selected from the group consisting of hydrogen, halogen, hydroxy, —$NO_2$, —CN, —($C_1$–$C_6$)alkyl, —($C_2$–$C_6$)alkenyl, —($C_2$–$C_6$)alkynyl, —C=N—OH, —C=N—O(($C_1$–$C_6$)alkyl), —$NR^5R^6$, —$OR^{12}$, —($C_3$–$C_7$) cycloalkyl, —($C_2$–$C_9$)heterocyclyl, —$CO_2R^{12}$, —$CONR^5R^6$, —$CONR^5R^8$, —$SR^7$, —$SOR^7$, —$SO_2R^7$, —$SO_2NR^5R^6$, —NHCOR$^2$, —$NR^{12}CONR^5R^6$, and —$NR^{12}SO_2R^7$, wherein said —($C_2$–$C_6$)alkenyl and —$(C_2–C_6)$alkynyl $R^2$ moieties may be optionally substituted by one to three $R^{12}$ groups; and $R^1$ is —$(C_1–C_6)$alkyl.

Also provided is a compound of formula 1 wherein $R^1$ is selected from hydrogen, hydroxy, and —$(C_1–C_6)$alkyl, optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8$; $R^2$ is hydrogen or —$(C_1–C_6)$alkyl, optionally substituted by one to three moieties independently selected from the group consisting of hydrogen, halogen, hydroxy, —$NO_2$, —CN, —$(C_1–C_6)$alkyl, —$(C_2–C_6)$alkenyl, —$(C_2–C_6)$alkynyl, —C=N—OH, —C=N—O$((C_1–C_6)$alkyl), —$NR^5R^6$, —$OR^{12}$, —$(C_3–C_7)$cycloalkyl, —$(C_2–C_9)$heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —$(C_2–C_6)$alkenyl and —$(C_2–C_6)$alkynyl $R^2$ moieties may be optionally substituted by one to three $R^{12}$ groups; and n is 1.

The invention further provides a compound of formula 1 wherein $R^1$ is selected from hydrogen, hydroxy, and —$(C_1–C_6)$alkyl, optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8$; $R^2$ is —$(C_1–C_6)$alkyl; and n is 1.

The present invention further provides a compound of formula 1, wherein $R^1$ is —$(C_1–C_6)$alkyl, optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8$; $R^2$ is —$(C_1–C_6)$ and n is 1.

The present invention also provides a compound of formula 1 wherein $R^1$ is selected from the group consisting of —$(C_3–C_7)$cycloalkyl and —$(C_2–C_9)$heterocyclyl, optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8 R^2$ is —$(C_1–C_6)$alkyl; and n is 1.

The invention also contemplates compounds of formula 1 wherein $R^1$ is selected from —$O(C_1–C_6)$alkyl, —$O(C_3–C_7)$cycloalkyl, and —$O(C_2–C_9)$heterocyclyl, optionally substituted by one to three moieties independently selected from the group consisting of hydrogen, halogen, hydroxy, —CN, —$(C_1–C_6)$alkyl, —$NR^5R^6$, —$OR^2$, —$(C_3–C_7)$cycloalkyl, —$(C_2–C_9)$heterocyclyl, —$CO_2R^{12}$, —$CONR^5R^6$ and —$CONR^5R^8$; $R^2$ is —$(C_1–C_6)$alkyl; and n is 1.

One embodiment of the invention is a compound of formula 1 wherein $R^1$ is —$NR^5R^6$, optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8$; $R^2$ is —$(C_1–C_6)$alkyl; and n is 1.

A further embodiment of the invention is a compound of formula 1 wherein $R^1$ is selected from —$SR^7$, —$SOR^7$, —$SO_2R^7$, and —$SO_2NR^5R^6$ optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8$; $R^2$ is —$(C_1–C_6)$alkyl; and n is 1.

The present invention also provides compounds of formula 1 wherein $R^1$ is —$CO_2R^{12}$, —$CONR^5R^6$, —NHCOR$^{12}$, $NR^{12}CONR^5R^6$, or —$NR^{12}SO_2R^7$, optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8$; $R^2$ is —$(C_1–C_6)$alkyl; and n is 1.

Also provided is a compound of formula 1 wherein $R^2$ is hydrogen or —$(C_1–C_6)$alkyl, optionally substituted by one to three moieties independently selected from the group consisting of hydrogen, halogen, hydroxy, —$NO_2$, —CN, —$(C_1–C_6)$alkyl, —$(C_2–C_6)$alkenyl, —$(C_2–C_6)$alkynyl, —C=N—OH, —C=N—O$((C_1–C_6)$alkyl), —$NR^5R^6$, —$OR^{12}$, —$(C_3–C_7)$cycloalkyl, —$(C_2–C_9)$heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —$(C_2–C_6)$alkenyl and —$(C_2–C_6)$alkynyl $R^2$ moieties may be optionally substituted by one to three $R^{12}$ groups; $R^1$ is —$(C_1–C_6)$alkyl; and n is 1.

Further provided is a compound of formula 1 wherein $R^2$ is —$(C_3–C_7)$cycloalkyl, or —$(C_2–C_9)$heterocyclyl, optionally substituted by one to three moieties independently selected from the group consisting of hydrogen, halogen, hydroxy, —$NO_2$, —CN, —$(C_1–C_6)$alkyl, —$(C_2–C_6)$alkenyl, —$(C_2–C_6)$alkynyl, —C=N—OH, —C=N—O$((C_1–C_6)$alkyl), —$NR^5R^6$, —$OR^{12}$, —$(C_3–C_7)$cycloalkyl, —$(C_2–C_9)$heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —$(C_2–C_6)$alkenyl and —$(C_2–C_6)$alkynyl $R^2$ moieties may be optionally substituted by one to three $R^{12}$ groups; $R^1$ is —$(C_1–C_6)$alkyl; and n is 1.

Another embodiment of the present invention is a compound of formula 1 wherein $R^2$ is —$CO_2R^{12}$ and —$CONR^5R^6$ optionally substituted by one to three moieties independently selected from the group consisting of hydrogen, halogen, hydroxy, —$NO_2$, —CN, —$(C_1–C_6)$alkyl, —$(C_2–C_6)$alkenyl, —$(C_2–C_6)$alkynyl, —C=N—OH, —C=N—O$((C_1–C_6)$alkyl), —$NR^5R^6$, —$OR^{12}$, —$(C_3–C_7)$cycloalkyl, —$(C_2–C_9)$heterocyclyl, —$CO_2R^{12}$, —$CONR^5R^6$, —$CONR^5R^8$, —$SR^7$, —$SOR^7$, —$SO_2R^7$, —$SO_2NR^5R^6$, —$NHCOR^{12}$, —$NR^{12}CONR^5R^6$, and —$NR^{12}SO_2R^7$, wherein said —$(C_2–C_6)$alkenyl and —$(C_2–C_6)$alkynyl $R^2$ moieties may be optionally substituted by one to three $R^{12}$ groups; $R^1$ is —$(C_1–C_6)$alkyl; and n is 1.

The invention further provides a compound of formula 1 wherein $R^1$ is selected from hydrogen, hydroxy, and —$(C_1–C_6)$alkyl, optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8$; $R^2$ is —$(C_1–C_6)$alkyl; and n is 1.

The present invention further provides a compound of formula 1, wherein $R^1$ is —$(C_1–C_6)$alkyl, optionally substituted by one to three moieties independently selected from the group consisting of hydrogen, halogen, hydroxy, —CN, —$(C_1–C_6)$alkyl, —$NR^5R^6$, —$OR^{12}$, —$(C_3–C_7)$cycloalkyl, —$(C_2–C_9)$heterocyclyl, —$CO_2R^{12}$, —$CONR^5R^6$ and —$CONR^5R^8$; $R^2$ is —$(C_1–C_6)$alkyl; and n is 1.

The present invention also provides a compound of formula 1 wherein $R^1$ is selected from the group consisting of —$(C_3–C_7)$cycloalkyl and —$(C_2–C_9)$heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 1.

The invention also contemplates compounds of formula 1 wherein R$^1$ is selected from —O(C$_1$–C$_6$)alkyl, —O(C$_3$–C$_7$)cycloalkyl, and —O(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 1.

One embodiment of the invention is a compound of formula 1 wherein R$^1$ is —NR$^5$R$^6$, optionally substituted by one to three moieties independently selected from the group consisting of hydrogen, halogen, hydroxy, —CN, —(C$_1$–C$_6$) alkyl, —NR$^5$R$^6$, —OR$^{12}$, —(C$_3$–C$_7$)cycloalkyl, —(C$_2$–C$_9$) heterocyclyl, CO$_2$R$^{12}$, —CONR$^5$R$^6$ and —CONR$^5$R$^8$; R$^2$ is —(C$_1$–C$_6$)alkyl; and n is 1.

A further embodiment of the invention is a compound of formula 1 wherein R$^1$ is selected from —SR$^7$, —SOR$^7$, —SO$_2$R$^7$, and —SO$_2$NR$^5$R$^6$, optionally substituted by one to three moieties independently selected from the group consisting of hydrogen, halogen, hydroxy, —CN, —(C$_1$–C$_6$) alkyl, —NR$^5$R$^6$, —OR$^{12}$, —(C$_3$–C$_7$)cycloalkyl, —(C$_2$–C$_9$) heterocyclyl, —CO$_2$R$^{12}$, —CONR$^5$R$^6$ and —CONR$^5$R$^8$; R$^2$ is —(C$_1$–C$_6$)alkyl; and n is 1.

The present invention also provides compounds of formula 1 wherein R$^1$ is —CO$_2$R$^{12}$, —CONR$^5$R$^6$, —NHCOR$^{12}$, —NR$^{12}$CONR$^5$R$^6$, or —NR$^{12}$SO$_2$R$^7$, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 1.

Also provided is a compound of formula 1 wherein R$^2$ is hydrogen or —(C$_1$–C$_6$)alkyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 1.

Further provided is a compound of formula 1 wherein R$^2$ is —(C$_3$–C$_7$)cycloalkyl, or —(C$_2$–C$_9$)heterocyclyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 1.

Another embodiment of the present invention is a compound of formula 1 wherein R$^2$ is —CO$_2$R$^{12}$ and —CONR$^5$R$^6$ optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$) cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 1.

Also provided is a compound of formula 1 wherein R$^1$ is selected from hydrogen, hydroxy, and —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^6$, R$^2$ is hydrogen or —(C$_1$–C$_6$)alkyl, optionally substituted by one to three moieties independently selected from the group consisting of hydrogen, halogen, hydroxy, —NO$_2$, —CN, —(C$_1$–C$_6$) alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$) cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; and n is 1.

The invention further provides a compound of formula 1 wherein R$^1$ is selected from hydrogen, hydroxy, and —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 1.

The present invention further provides a compound of formula 1, wherein R$^1$ is —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 1.

The present invention also provides a compound of formula 1 wherein R$^1$ is selected from the group consisting of —(C$_3$–C$_7$)cycloalkyl and —(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 1.

The invention also contemplates compounds of formula 1 wherein R$^1$ is selected from —O(C$_1$–C$_6$)alkyl, —O(C$_3$–C$_7$)cycloalkyl, and —O(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^3$; R$^2$ is hydrogen; and n is 1.

One embodiment of the invention is a compound of formula 1 wherein R$^1$ is —NR$^5$R$^6$, optionally substituted by one to three moieties independently selected from the group consisting of hydrogen, halogen, hydroxy, —CN, —(C$_1$–C$_6$) alkyl, —NR$^5$R$^5$, —OR$^{12}$, —(C$_3$–C$_7$)cycloalkyl, —(C$_2$–C$_9$) heterocyclyl, —CO$_2$R$^1$, —CONR$^5$R$^6$ and —CONR$^5$R$^8$; R$^2$ is hydrogen; and n is 1.

A further embodiment of the invention is a compound of formula 1 wherein R$^1$ is selected from —SR$^7$, —SOR$^7$, —$SO_2R^7$, and —$SO_2NR^5R^6$, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$; $R^2$ is hydrogen; and n is 1.

The present invention also provides compounds of formula 1 wherein $R^1$ is —$CO_2R^{12}$, —$CONR^5R^6$, —NHCOR$^{12}$, —$NR^{12}CONR^5R^6$, or —$NR^{12}SO_2R^7$, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$; $R^2$ is hydrogen; and n is 1.

Also provided is a compound of formula 1 wherein $R^2$ is hydrogen or —$(C_1-C_6)$alkyl, optionally substituted by one to three moieties independently selected from the group consisting of hydrogen, halogen, hydroxy, —$NO_2$, —CN, —$(C_1-C_6)$alkyl, —$(C_2-C_6)$alkenyl, —$(C_2-C_6)$alkynyl, —C=N—OH, —C=N—O($(C_1-C_6)$alkyl), —$NR^5R^6$, —$OR^{12}$, —$(C_3-C_7)$cycloalkyl, —$(C_2-C_9)$heterocyclyl, —$CO_2R^{12}$, —$CONR^5R^6$, —$CONR^5R^8$, —$SR^7$, —$SOR^7$, —$SO_2R^7$, —$SO_2NR^5R^6$, —NHCOR$^{12}$, —$NR^{12}CONR^5R^6$, and —$NR^{12}SO_2R^7$, wherein said —$(C_2-C_6)$alkenyl and —$(C_2-C_6)$alkynyl $R^2$ moieties may be optionally substituted by one to three $R^{12}$ groups; $R^1$ is hydrogen; and n is 1.

Further provided is a compound of formula 1 wherein $R^2$ is —$(C_3-C_7)$cycloalkyl, or —$(C_2-C_9)$heterocyclyl, optionally substituted by one to three moieties independently selected from the group consisting of hydrogen, halogen, hydroxy, —$NO_2$, —CN, —$(C_1-C_6)$alkyl, —$(C_2-C_6)$alkenyl, —$(C_2-C_6)$alkynyl, —C=N—OH, —C=N—O($(C_1-C_6)$alkyl), —$NR^5R^6$, —$OR^{12}$, —$(C_3-C_7)$cycloalkyl, —$(C_2-C_9)$heterocyclyl, —$CO_2R^{12}$, —$CONR^5R^6$, —$CONR^5R^8$, —$SR^7$, —$SOR^7$, —$SO_2R^7$, —$SO_2NR^5R^6$, —NHCOR$^{12}$, —$NR^2CONR^5R^6$, and —$NR^{12}SO_2R^7$, wherein said —$(C_2-C_6)$alkenyl and —$(C_2-C_6)$alkynyl $R^2$ moieties may be optionally substituted by one to three $R^{12}$ groups; $R^1$ is hydrogen; and n is 1.

Another embodiment of the present invention is a compound of formula 1 wherein $R^2$ is —$CO_2R^{12}$ and —$CONR^5R^6$ optionally substituted by one to three moieties independently selected from the group consisting of hydrogen, halogen, hydroxy, —$NO_2$, —CN, —$(C_1-C_6)$alkyl, —$(C_2-C_6)$alkenyl, —$(C_2-C_6)$alkynyl, —C=N—OH, —C=N—O($(C_1-C_6)$alkyl), —$NR^5R^6$, —$OR^{12}$, —$(C_3-C_7)$cycloalkyl, —$(C_2-C_9)$heterocyclyl, $CO_2R^{12}$, —$CONR^5R^6$, —$CONR^5R^8$, —$SR^7$, —$SOR^7$, —$SO_2R^7$, —$SO_2NR^5R^6$, —NHCOR$^{12}$, —$NR^{12}CONR^5R^6$, and —$NR^{12}SO_2R^7$, wherein said —$(C_2-C_6)$alkenyl and —$(C_2-C_6)$alkynyl $R^2$ moieties may be optionally substituted by one to three $R^{12}$ groups; $R^1$ is hydrogen; and n is 1.

Also provided is a compound of formula 1 wherein $R^1$ is selected from hydrogen, hydroxy, and —$(C_1-C_6)$alkyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$; $R^2$ is hydrogen or —$(C_1-C_6)$alkyl, optionally substituted by one to three moieties independently selected from the group consisting of hydrogen, halogen, hydroxy, —$NO_2$, —CN, —$(C_1-C_6)$alkyl, —$(C_2-C_6)$alkenyl, —$(C_2-C_6)$alkynyl, —C=N—OH, —C=N—O($(C_1-C_6)$alkyl), —$NR^5R^6$, —$OR^{12}$, —$(C_3-C_7)$cycloalkyl, —$(C_2-C_9)$heterocyclyl, —$CO_2R^{12}$, —$CONR^5R^6$, —$CONR^5R^8$, —$SR^7$, —$SOR^7$, —$SO_2R^7$, —$SO_2NR^5R^6$, —NHCOR$^{12}$, —$NR^{12}CONR^5R^6$, and —$NR^{12}SO_2R^7$, wherein said —$(C_2-C_6)$alkenyl and —$(C_2-C_6)$alkynyl $R^2$ moieties may be optionally substituted by one to three $R^{12}$ groups; and n is 2.

The invention further provides a compound of formula 1 wherein $R^1$ is selected from hydrogen, hydroxy, and —$(C_1-C_6)$alkyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$; $R^2$ is —$(C_1-C_6)$alkyl; and n is 2.

The present invention further provides a compound of formula 1, wherein $R^1$ is —$(C_1-C_6)$alkyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}CONR^5R^6$ and —$CONR^5R^8$; $R^2$ is —$(C_1-C_6)$alkyl; and n is 2.

The present invention also provides a compound of formula 1 wherein $R^1$ is selected from the group consisting of —$(C_3-C_7)$cycloalkyl and —$(C_2-C_9)$heterocyclyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$; $R^2$ is —$(C_1-C_6)$alkyl; and n is 2.

The invention also contemplates compounds of formula 1 wherein $R^1$ is selected from —$O(C_1-C_6)$alkyl, —$O(C_3-C_7)$cycloalkyl, and —$O(C_2-C_9)$heterocyclyl, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$; $R^2$ is —$(C_1-C_6)$alkyl; and n is 2.

One embodiment of the invention is a compound of formula 1 wherein $R^1$ is —$NR^5R^6$, optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$; $R^2$ is —$(C_1-C_6)$alkyl; and n is 2.

A further embodiment of the invention is a compound of formula 1 wherein $R^1$ is selected from —$SR^7$, —$SOR^7$, —$SO_2R^7$, and —$SO_2NR^5R^6$ optionally substituted by one to three moieties independently selected from the group consisting of hydrogen, halogen, hydroxy, —CN, —$(C_1-C_6)$alkyl, —$NR^5R^6$, —$OR^{12}$, —$(C_3-C_7)$cycloalkyl, —$(C_2-C_9)$heterocyclyl, —$CO_2R^{12}$, —$CONR^5R^6$ and —$CONR^5R^8$; $R^2$ is —$(C_1-C_6)$alkyl; and n is 2.

The present invention also provides compounds of formula 1 wherein $R^1$ is —$CO_2R^{12}$, —$CONR^5R^6$, —NHCOR$^{12}$, —$NR^{12}CONR^5R^6$, or —$NR^{12}SO_2R^7$, optionally substituted by one to three moieties independently selected from the group consisting of hydrogen, halogen, hydroxy, —CN, —$(C_1-C_6)$alkyl, —$NR^5R^6$, —$OR^7$, —$(C_3-C_7)$cycloalkyl, —$(C_2-C_9)$heterocyclyl, —$CO_2R^{12}$, —$CONR^5R^6$ and —$CONR^5R^8$; $R^2$ is —$(C_1-C_6)$alkyl; and n is 2.

Also provided is a compound of formula 1 wherein $R^2$ is hydrogen or —$(C_1-C_6)$alkyl, optionally substituted by one to three moieties independently selected from the group consisting of hydrogen, halogen, hydroxy, —$NO_2$, —CN, —$(C_1-C_6)$alkyl, —$(C_2-C_6)$alkenyl, —$(C_2-C_6)$alkynyl, —C=N—OH, —C=N—O($(C_1-C_6)$alkyl), —$NR^5R^6$, —$OR^{12}$, —$(C_3-C_7)$cycloalkyl, —$(C_2-C_9)$heterocyclyl, —$CO_2R^{12}$, —$CONR^5R^6$, —$CONR^5R^8$, —$SR^7$, —$SOR^7$, —$SO_2R^{12}$, —$SO_2NR^5R^6$, —NHCOR$^{12}$, —$NR^{12}CONR^5R^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 2.

Further provided is a compound of formula 1 wherein R$^2$ is —(C$_3$–C$_7$)cycloalkyl, or —(C$_2$–C$_9$)heterocyclyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 2.

Another embodiment of the present invention is a compound of formula 1 wherein R$^2$ is —CO$_2$R$^{12}$ and —CONR$^5$R$^6$ optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 2.

The invention further provides a compound of formula 1 wherein R$^1$ is selected from hydrogen, hydroxy, and —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 2.

The present invention further provides a compound of formula 1, wherein R$^1$ is —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 2.

The present invention also provides a compound of formula 1 wherein R$^1$ is selected from the group consisting of —(C$_3$–C$_7$)cycloalkyl and —(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 2.

The invention also contemplates compounds of formula 1 wherein R$^1$ is selected from —O(C$_1$–C$_6$)alkyl, —O(C$_3$–C$_7$)cycloalkyl, and —O(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 2.

One embodiment of the invention is a compound of formula 1 wherein R$^1$ is —NR$^5$R$^6$ optionally substituted by one to three moieties independently selected from the group consisting of hydrogen, halogen, hydroxy, —CN, —(C$_1$–C$_6$)alkyl, —NR$^5$R$^5$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl, and n is 2.

A further embodiment of the invention is a compound of formula 1 wherein R$^1$ is selected from —SR$^7$, —SOR$^7$, —SO$_2$R$^7$, and —SO$_2$NR$^5$R$^6$, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 2.

The present invention also provides compounds of formula 1 wherein R$^1$ is CO$_2$R$^{12}$, —CONR$^5$R$^6$, —NHCOR$^{12}$, —NR$^{12}$CONR$^5$R$^6$, or —NR$^{12}$SO$_2$R$^7$, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is —(C$_1$–C$_6$)alkyl; and n is 2.

Also provided is a compound of formula 1 wherein R$^2$ is hydrogen or —(C$_1$–C$_6$)alkyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 2.

Further provided is a compound of formula 1 wherein R$^2$ is —(C$_3$–C$_7$)cycloalkyl, or —(C$_2$–C$_9$)heterocyclyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, (C$_3$–C$_7$)cycloalkyl, —(C$_2$–C$_9$)heterocyclyl, —CO$_2$R$^{12}$, —CONR$^5$R$^6$, —CONR$^5$R$^6$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 2.

Another embodiment of the present invention is a compound of formula 1 wherein R$^2$ is —CO$_2$R$^{12}$ and —CONR$^5$R$^6$ optionally substituted by one to three moieties independently selected from the group consisting of hydrogen, halogen, hydroxy, —NO$_2$, —CN, —(C$_1$–C$_6$)alkyl, —(C$_2$–C$_8$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^2$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is —(C$_1$–C$_6$)alkyl; and n is 2.

Also provided is a compound of formula 1 wherein R$^1$ is selected from hydrogen, hydroxy, and —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen or —(C$_1$–C$_6$)alkyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^5$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; and n is 2.

The invention further provides a compound of formula 1 wherein R$^1$ is selected from hydrogen, hydroxy, and —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 2.

The present invention further provides a compound of formula 1, wherein R$^1$ is —(C$_1$–C$_6$)alkyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; a is 2.

The present invention also provides a compound of formula 1 wherein R$^1$ is selected from the group consisting of —(C$_3$–C$_7$)cycloalkyl and —(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 2.

The invention also contemplates compounds of formula 1 wherein R$^1$ is selected from —O(C$_1$–C$_6$)alkyl, —O(C$_3$–C$_7$)cycloalkyl, and —O(C$_2$–C$_9$)heterocyclyl, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 2.

One embodiment of the invention is a compound of formula 1 wherein R$^1$ is —NR$^5$R$^6$, optionally substituted by one to three moieties independently selected from the group consisting of hydrogen, halogen, hydroxy, —CN, —(C$_1$–C$_6$)alkyl, —NR$^5$R$^5$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 2.

A further embodiment of the invention is a compound of formula 1 wherein R$^1$ is selected from —SR$^7$, —SOR$^7$, —SO$_2$R$^7$, and —SO$_2$NR$^5$R$^6$ optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 2.

The present invention also provides compounds of formula 1 wherein R$^1$ is —CO$_2$R$^{12}$, —CONR$^5$R$^6$, —NHCOR$^{12}$, —NR$^2$CONR$^5$R$^6$, or —NR$^{12}$SO$_2$R$^7$, optionally substituted by one to three moieties independently selected from the group consisting of hydrogen, halogen, hydroxy, —CN, —(C$_1$–C$_6$)alkyl, —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$ and —CONR$^5$R$^8$; R$^2$ is hydrogen; and n is 2.

Also provided is a compound of formula 1 wherein R$^2$ is hydrogen or —(C$_1$–C$_6$)alkyl, optionally substituted by one to three moieties independently selected from the group consisting of hydrogen, halogen, hydroxy, —NO$^2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^5$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is hydrogen; and n is 2.

Further provided is a compound of formula 1 wherein R$^2$ is —(C$_3$–C$_7$)cycloalkyl, or —(C$_2$–C$_9$)heterocyclyl, optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is hydrogen; and n is 2.

Another embodiment of the present invention is a compound of formula 1 wherein R$^2$ is —CO$_2$R$^5$ and —CONR$^5$R$^6$ optionally substituted by one to three moieties independently selected from the group consisting of hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^5$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl R$^2$ moieties may be optionally substituted by one to three R$^{12}$ groups; R$^1$ is hydrogen; and n is 2.

The present invention also provides a compound of formula 1 in which R$^1$ and R$^2$ are taken together with the atom(s) to which they are attached to form a —(C$_3$–C$_{10}$) cycloalkyl optionally substituted by one to three moieties selected from the group consisting of a hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl moieties of said cyclic group may be optionally substituted by one to three R$^{12}$ groups.

The present invention further provides a compound of formula 1 in which R$^1$ and R$^2$ are taken together with the atom(s) to which they are attached to form a —(C$_2$–C$_9$) heterocyclyl optionally substituted by one to three moieties selected from the group consisting of a hydrogen, halogen, hydroxy, —NO$_2$, —CN, —(C$_1$–C$_6$)alkyl, —(C$_2$–C$_6$)alkenyl, —(C$_2$–C$_6$)alkynyl, —C=N—OH, —C=N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl moieties of said cyclic group may be optionally substituted by one to three R$^{12}$ groups.

The present invention also provides a compound of formula 1 in which R$^1$ and R$^2$ are taken together with the atom(s) to which they are attached to form a —(C$_3$–C$_{10}$) cycloalkyl optionally substituted by one to three moieties selected from the group consisting of a hydrogen, halogen, hydroxy, —NO$_2$, —CN, —(C$_1$–C$_6$)alkyl, —(C$_2$–C$_6$)alkenyl, —(C$_2$–C$_6$)alkynyl, —C═N—OH, —C═N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^8$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl moieties of said cyclic group may be optionally substituted by one to three R$^{12}$ groups; and n is 1.

The present invention further provides a compound of formula 1 in which R$^1$ and R$^2$ are taken together with the atom(s) to which they are attached to form a —(C$_2$–C$_9$)heterocyclyl optionally substituted by one to three moieties selected from the group consisting of a hydrogen, halogen, hydroxy, —NO$_2$, —CN, —(C$_1$–C$_6$)alkyl, —(C$_2$–C$_6$)alkenyl, —(C$_2$–C$_6$)alkynyl, —C═N—OH, —C═N—O((C$_1$–C$_6$)alkyl), —NR$^5$R$^6$, —OR$^{12}$, —(C$_3$–C$_7$)cycloalkyl, —(C$_2$–C$_9$)heterocyclyl, —CO$_2$R$^{12}$, —CONR$^5$R$^6$, —CONR$^5$R$^6$, —SR$^7$, —SOR$^7$, —SO$_2$R$^7$, —SO$_2$NR$^5$R$^6$, —NHCOR$^{12}$, —NR$^{12}$CONR$^5$R$^6$, and —NR$^{12}$SO$_2$R$^7$, wherein said —(C$_2$–C$_6$)alkenyl and —(C$_2$–C$_6$)alkynyl moieties of said cyclic group may be optionally substituted by one to three R$^{12}$ groups; and n is 1.

In a preferred embodiment, R$^4$ is a substituent selected from the group consisting of hydrogen, (C$_1$–C$_6$)alkyl, —(C$_3$–C$_7$)cycloalkyl, and —(C$_2$–C$_9$)heterocyclyl; wherein said (C$_1$–C$_6$)alkyl, —(C$_3$–C$_7$)cycloalkyl, and —(C$_2$–C$_9$)heterocyclyl R$^4$ substituents are optionally substituted by one to three moieties independently selected from the group consisting of hydrogen, halogen, hydroxyl, —(C$_1$–C$_6$)alkyl, —CN, —NR$^5$R$^6$, —OR$^{12}$, —(C$_3$–C$_7$)cycloalkyl, —(C$_2$–C$_9$)heterocyclyl, —CO$_2$R$^{12}$, and —CONR$^5$R$^8$; with the proviso that a heteroatom of the foregoing R$^4$ substituents may not be bound to an sp$^3$ carbon atom bound to another heteroatom; and wherein R$^5$ and R$^3$ of said —CONR$^5$R$^8$ group may be taken together with the atoms to which they are attached to form a —(C$_3$–C$_{10}$)cycloalkyl or —(C$_2$–C$_9$)heterocyclyl.

In a further preferred embodiment, R$^4$ is hydrogen.

Further, the invention provides a compound of formula 1 wherein R$^5$ and R$^6$ are each substituents independently selected from the group consisting of hydrogen and —(C$_1$–C$_6$)alkyl, optionally substituted as described above.

Specific embodiments of the present invention are compounds selected from

N-(1-Methyl-1-phenyl-ethyl)-3-{([2-(2-oxo-2,3-dihydro-1H-indol-5-ylamino)-5-trifluoromethyl-pyrimidin-4-ylamino]-methyl}-benzenesulfonamide;

3-{[2-(2-Oxo-2,3-dihydro-1H-indol-5-ylamino)-5-trifluoromethyl-pyrimidin-4-ylamino]-methyl}-benzenesulfonamide;

5-{4-[3-(Trifluoro-methanesulfonyl)-benzylamino]-5-trifluoromethyl-pyrimidin-2-ylamino}-1,3-dihydro-indol-2-one;

5-{4-[(Piperidin-3-ylmethyl)-amino]-5-trifluoromethyl-pyrimidin-2-ylamino}-1,3-dihydro-indol-2-one;

5-{4-[(1-Methanesulfonyl-piperidin-3-ylmethyl)-amino]-5-trifluoromethyl-pyrimidin-2-ylamino}-1,3-dihydro-indol-2-one;

N-(3-{[2-(2-Oxo-2,3-dihydro-1H-indol-5-ylamino)-5-trifluoromethyl-pyrimidin-4-ylamino]-methyl}-phenyl)-methanesulfonamide;

3-Oxo-3-(3-{[2-(2-oxo-2,3-dihydro-1H-indol-5-ylamino)-5-trifluoromethyl-pyrimidin-4-ylamino]-methyl}-piperidin-1-yl)-propionitrile;

5-{4-[3-(1,1-Dioxo-1N$^6$-isothiazolidin-2-yl)-propylamino]-5-trifluoromethyl-pyrimidin-4-ylamino}-1,3-dihydro-indol-2-one;

5-[4-(2-Methyl-butylamino)-5-trifluoromethyl-pyrimidin-2-ylamino]-1,3-dihydro-indol-2-one;

5-{4-[(1-Methanesulfonyl-piperidin-2-ylmethyl)-amino]-5-trifluoromethyl-pyrimidin-2-ylamino}-1,3-dihydro-indol-2-one;

N-{2-[2-(2-Oxo-2,3-dihydro-1H-indol-5-ylamino)-5-trifluoromethyl-pyrimidin-4-ylamino]-ethyl}-methanesulfonamide;

N-{4-[2-(2-Oxo-2,3-dihydro-1H-indol-5-ylamino)-5-trifluoromethyl-pyrimidin-4-ylamino]-butyl}-methanesulfonamide;

5-{4-[(1-Methanesulfonyl-piperidin-4-ylmethyl)-amino]-5-trifluoromethyl-pyrimidin-2-ylamino}-1,3-dihydro-indol-2-one;

N-Methyl-N-{2-[2-(2-oxo-2,3-dihydro-1H-indol-5-ylamino)-5-trifluoromethyl-pyrimidin-4-ylamino]-ethyl}-methanesulfonamide;

Methanesulfonic acid 3-{[2-(2-oxo-2,3-dihydro-1H-indol-5-ylamino)-5-trifluoromethyl-pyrimidin-4-ylamino]-methyl}-phenyl ester;

N-{3-[2-(2-Oxo-2,3-dihydro-1H-indol-5-ylamino)-5-trifluoromethyl-pyrimidin-4-ylamino]-propyl}-methanesulfonamide;

5-{4-[(4-Methanesulfonyl-morpholin-2-ylmethyl)-amino]-5-trifluoromethyl-pyrimidin-2-ylamino}-1,3-dihydro-indol-2-one;

N-(4-Fluoro-3-{[2-(2-oxo-2,3-dihydro-1H-indol-5-ylamino)-5-trifluoromethyl-pyrimidin-4-ylamino]-methyl}-phenyl)-methanesulfonamide;

5-{4-[(5-Oxo-morpholin-2-ylmethyl)-amino]-5-trifluoromethyl-pyrimidin-2-ylamino}-1,3-dihydro-indol-2-one;

N-(4-Methoxy-3-{[2-(2-oxo-2,3-dihydro-1H-indol-5-ylamino)-5-trifluoromethyl-pyrimidin-4-ylamino]-methyl}-phenyl)-methanesulfonamide;

N-(4-Methyl-3-{[2-(2-oxo-2,3-dihydro-1H-indol-5-ylamino)-5-trifluoromethyl-pyrimidin-4-ylamino]-methyl}-phenyl)-methanesulfonamide;

5-[4-(3-Methanesulfonylmethyl-benzylamino)-5-trifluoromethyl-pyrimidin-2-ylamino]-1,3-dihydro-indol-2-one;

5-{4-[(4-Trifluoroacetyl-morpholin-2-ylmethyl)-amino]-5-trifluoromethyl-pyrimidin-2-ylamino}-1,3-dihydro-indol-2-one;

5-{4-[(1-Methanesulfonyl-azetidin-3-ylmethyl)-amino]-5-trifluoromethyl-pyrimidin-2-ylamino}-1,3-dihydro-indol-2-one;

N-Methyl-N-(4-methyl-3-{[2-(2-oxo-2,3-dihydro-1H-indol-5-ylamino)-5-trifluoromethyl-pyrimidin-4-ylamino]-methyl}-phenyl)-methanesulfonamide;

5-{4-[(1-Methanesulfonyl-pyrrolidin-3-ylmethyl)-amino]-5-trifluoromethyl-pyrimidin-2-ylamino}-1,3-dihydro-indol-2-one;

N-Methyl-N-{3-[2-(2-oxo-2,3-dihydro-1H-indol-5-ylamino)-5-trifluoromethyl-pyrimidin-4-ylamino]-propyl}-methanesulfonamide;

5-{4-[2-(1-Methanesulfonyl-piperidin-2-yl)-ethylamino]-5-trifluoromethyl-pyrimidin-2-ylamino}-1,3-dihydro-indol-2-one;

5-{4-[(4-Methanesulfonyl-pyridin-2-ylmethyl)-amino]-5-trifluoromethyl-pyrimidin-2-ylamino}-1,3-dihydro-indol-2-one;

{2,2-Dimethyl-3-[2-(2-oxo-2,3-dihydro-1H-indol-5-ylamino)-5-trifluoromethyl-pyrimidin-4-ylamino]-propyl}-carbamic acid tert-butyl ester;

5-[4-(3-Isopropoxy-propylamino)-5-trifluoromethyl-pyrimidin-2-ylamino]-1,3-dihydro-indol-2-one;
5-{4-[(1-Methyl-piperidin-3-ylmethyl)-amino]-5-trifluoromethyl-pyrimidin-2-ylamino}-1,3-dihydro-indol-2-one;
5-{4-[(Tetrahydro-pyran-4-ylmethyl)-amino]-5-trifluoromethyl-pyrimidin-2-ylamino}-1,3-dihydro-indol-2-one;
5-[4-(2-Ethyl-butylamino)-5-trifluoromethyl-pyrimidin-2-ylamino]-1,3-dihydro-indol-2-one;
5-{4-[(Tetrahydro-furan-2R-ylmethyl)-amino]-5-trifluoromethyl-pyrimidin-2-ylamino}-1,3-dihydro-indol-2-one;
5-{4-[(Tetrahydro-furan-2S-ylmethyl)-amino]-5-trifluoromethyl-pyrimidin-2-ylamino}-1,3-dihydro-indol-2-one;
5-{4-[(5-Methyl-furan-2-ylmethyl)-amino]-5-trifluoromethyl-pyrimidin-2-ylamino}-1,3-dihydro-indol-2-one;
5-{4-[(1-Methanesulfonyl-pyrrolidin-2-ylmethyl)-amino]-5-trifluoromethyl-pyrimidin-2-ylamino}-1,3-dihydro-indol-2-one;
5-{4-[(Adamantan-2-ylmethyl)-amino]-5-trifluoromethyl-pyrimidin-2-ylamino}-1,3-dihydro-indol-2-one;
5-{4-[(Adamantan-2-ylmethyl)-amino]-5-trifluoromethyl-pyrimidin-2-ylamino}-1,3-dihydro-indol-2-one;
5-[4-(2-Methoxy-2-methyl-propylamino)-5-trifluoromethyl-pyrimidin-2-ylamino]-1,3-dihydro-indol-2-one;
5-{4-[(endo-Bicyclo[2.2.1]hept-5-en-2-ylmethyl)-amino]-5-trifluoromethyl-pyrimidin-2-ylamino}-1,3-dihydro-indol-2-one;
(3-{[2-(2-Oxo-2,3-dihydro-1H-indol-5-ylamino)-5-trifluoromethyl-pyrimidin-4-ylamino]-methyl}-benzyl)-phosphonic acid dimethyl ester;
5-[4-(3-Methyl-butylamino)-5-trifluoromethyl-pyrimidin-2-ylamino]-1,3-dihydro-indol-2-one;
5-{4-[(2-Hydroxy-cyclohexylmethyl)-amino]-5-trifluoromethyl-pyrimidin-2-ylamino}-1,3-dihydro-indol-2-one;
N-(4-Methoxy-3-{[2-(2-oxo-2,3-dihydro-1H-indol-5-ylamino)-5-trifluoromethyl-pyrimidin-4-ylamino]-methyl}-phenyl)-N-methyl-methanesulfonamide;
5-{4-[(4-Ethanesulfonyl-morpholin-2-ylmethyl)-amino]-5-trifluoromethyl-pyrimidin-2-ylamino}-1,3-dihydro-indol-2-one;
5-(4-{[4-(Propane-2-sulfonyl)-morpholin-2-ylmethyl]-amino}-5-trifluoromethyl-pyrimidin-2-ylamino)-1,3-dihydro-indol-2-one;
5-{4-[(4-Acetyl-morpholin-2-ylmethyl)-amino]-5-trifluoromethyl-pyrimidin-2-ylamino}-1,3-dihydro-indol-2-one;
5-{4-[(4-Propionyl-morpholin-2-ylmethyl)-amino]-5-trifluoromethyl-pyrimidin-2-ylamino}-1,3-dihydro-indol-2-one;
5-(4-{[4-(2,2-Dimethyl-propionyl)-morpholin-2-ylmethyl]-amino}-5-trifluoromethyl-pyrimidin-2-ylamino)-1,3-dihydro-indol-2-one;
2-{[2-(2-Oxo-2,3-dihydro-1H-indol-5-ylamino)-5-trifluoromethyl-pyrimidin-4-ylamino]methyl}-morpholine-4-carboxylic acid methyl ester;
5-{4-[(4-Methoxyacetyl-morpholin-2-ylmethyl)-amino]-5-trifluoromethyl-pyrimidin-2-ylamino}-1,3-dihydro-indol-2-one;
5-[4-(3-Ethanesulfonyl-benzylamino)-5-trifluoromethyl-pyrimidin-2-ylamino]-1,3-dihydro-indol-2-one;
5-{4-[(4-Methanesulfonyl-morpholin-2R-ylmethyl)-amino]-5-trifluoromethyl-pyrimidin-2-ylamino}-1,3-dihydro-indol-2-one;
5-{4-[(4-Methanesulfonyl-morpholin-2S-ylmethyl)-amino]-5-trifluoromethyl-pyrimidin-2-ylamino}-1,3-dihydro-indol-2-one;
5-{4-[(Pyrimidin-2-ylmethyl)-amino]-5-trifluoromethyl-pyrimidin-2-ylamino}-1,3-dihydro-indol-2-one;
5-{4-[(Pyrazin-2-ylmethyl)-amino]-5-trifluoromethyl-pyrimidin-2-ylamino}-1,3-dihydro-indol-2-one;
N-(4-Fluoro-3-{[2-(2-oxo-2,3-dihydro-1H-indol-5-ylamino)-5-trifluoromethyl-pyrimidin-4-ylamino]-methyl}-phenyl)-N-methyl-methanesulfonamide;
5-{4-[(1-Methanesulfonyl-piperidin-3-ylmethyl)-amino]-5-trifluoromethyl-pyrimidin-2-ylamino}-1,3-dihydro-indol-2-one;
5-{4-[(4-Isobutyryl-morpholin-2-ylmethyl)-amino]-5-trifluoromethyl-pyrimidin-2-ylamino}-1,3-dihydro-indol-2-one;
5-[4-(3,3-Dimethyl-2-oxo-butylamino)-5-trifluoromethyl-pyrimidin-2-ylamino]-1,3-dihydro-indol-2-one;
5-[4-(1,2-Dimethyl-propylamino)-5-trifluoromethyl-pyrimidin-2-ylamino]-1,3-dihydro-indol-2-one;
5-[4-(2-Methoxy-1-methyl-ethylamino)-5-trifluoromethyl-pyrimidin-2-ylamino]-1,3-dihydro-indol-2-one;
5-{4-[2-(1,1-Dioxo-1D$^6$-isothiazolidin-2-yl)-ethylamino]-5-trifluoromethyl-pyrimidin-2-ylamino}-1,3-dihydro-indol-2-one;
5-[4-(3-Methylamino-propylamino)-5-trifluoromethyl-pyrimidin-2-ylamino]-1,3-dihydro-indol-2-one;
5-{4-[(Pyridin-3-ylmethyl)-amino]-5-trifluoromethyl-pyrimidin-2-ylamino}-1,3-dihydro-indol-2-one;
5-{4-[(6-Methanesulfonyl-pyridin-2-ylmethyl)-amino]-5-trifluoromethyl-pyrimidin-2-ylamino}-1,3-dihydro-indol-2-one;
5-{4-[3-(1,1-Dioxo-1,1,6-isothiazolidin-2-yl)-benzylamino]-5-trifluoromethyl-pyrimidin-2-ylamino}-1,3-dihydro-indol-2-one;
5-[4-(1R-Phenyl-ethylamino)-5-trifluoromethyl-pyrimidin-2-ylamino]-1,3-dihydro-indol-2-one;
5-(4-Isopropylamino-5-trifluoromethyl-pyrimidin-2-ylamino)-1,3-dihydro-indol-2-one;
5-(4R-sec-Butylamino-5-trifluoromethyl-pyrimidin-2-ylamino)-1,3-dihydro-indol-2-one;
5-(4S-sec-Butylamino-5-trifluoromethyl-pyrimidin-2-ylamino)-1,3-dihydro-indol-2-one;
5-[4-(2-Methylamino-ethylamino)-5-trifluoromethyl-pyrimidin-2-ylamino]-1,3-dihydro-indol-2-one;
5-[4-(1S-Phenyl-ethylamino)-5-trifluoromethyl-pyrimidin-2-ylamino]-1,3-dihydro-indol-2-one;
5-{4-[(2-Methanesulfonylmethyl-thiazol-4-ylmethyl)-amino]-5-trifluoromethyl-pyrimidin-2-ylamino}-1,3-dihydro-indol-2-one;
5-(4-Propylamino-5-trifluoromethyl-pyrimidin-2-ylamino)-1,3-dihydro-indol-2-one;
5-[4-(2-Hydroxy-1-methyl-ethylamino)-5-trifluoromethyl-pyrimidin-2-ylamino]-1,3-dihydro-indol-2-one;
5-[4-(1-Hydroxymethyl-propylamino)-5-trifluoromethyl-pyrimidin-2-ylamino]-1,3-dihydro-indol-2-one;
5-{4-[(5-Methanesulfonyl-pyridin-3-ylmethyl)-amino]-5-trifluoromethyl-pyrimidin-2-ylamino}-1,3-dihydro-indol-2-one;
5-{4-[(Pyridin-4-ylmethyl)-amino]-5-trifluoromethyl-pyrimidin-2-ylamino-1,3-dihydro-indol-2-one;
5-[4-(1,3-Dimethyl-butylamino)-5-trifluoromethyl-pyrimidin-2-ylamino]-1,3-dihydro-indol-2-one;
N-Isopropyl-N-{3-[2-(2-oxo-2,3-dihydro-1H-indol-5-ylamino)-5-trifluoromethyl-pyrimidin-4-ylamino]-propyl}-methanesulfonamide;
5-[4-(1S-Hydroxymethyl-2-methyl-propylamino)-5-trifluoromethyl-pyrimidin-2-ylamino]-1,3-dihydro-indol-2-one;
N-Cyclohexyl-N-{3-[2-(2-oxo-2,3-dihydro-1H-indol-5-ylamino)-5-trifluoromethyl-pyrimidin-4-ylamino]-propyl}-methanesulfonamide;

5-[4-(1,2,3,4-Tetrahydro-naphthalen-1-ylamino)-5-trifluoromethyl-pyrimidin-2-ylamino]-1,3-dihydro-indol-2-one;

5-{4-[(1-Methanesulfonyl-pyrrolidin-2S-ylmethyl)-amino]-5-trifluoromethyl-pyrimidin-2-ylamino}-1,3-dihydro-indol-2-one;

5-{4-[(3-Methyl-thiophen-2-ylmethyl)-amino]-5-trifluoromethyl-pyrimidin-2-ylamino}-1,3-dihydro-indol-2-one;

5-{4-[(1-Methanesulfonyl-pyrrolidin-3R-ylmethyl)-amino]-5-trifluoromethyl-pyrimidin-2-ylamino}-1,3-dihydro-indol-2-one;

5-[4-(2-Hydroxy-1S-phenyl-ethylamino)-5-trifluoromethyl-pyrimidin-2-ylamino]-1,3-dihydro-indol-2-one;

5-[4-(2-Hydroxy-1S-methyl-ethylamino)-5-trifluoromethyl-pyrimidin-2-ylamino]-1,3-dihydro-indol-2-one;

5-[4-(1R-Hydroxymethyl-propylamino)-5-trifluoromethyl-pyrimidin-2-ylamino]-1,3-dihydro-indol-2-one;

5-[4-(1-Pyrimidin-4-y-ethylamino)-5-trifluoromethyl-pyrimidin-2-ylamino]-1,3-dihydro-indol-2-one;

5-[4-(1,1-Dioxo-tetrahydro-1-thiophen-3-ylamino)-5-trifluoromethyl-pyrimidin-2-ylamino]-1,3-dihydro-indol-2-one;

5-{4-[(1H-Imidazol-2-ylmethyl)-amino]-5-trifluoromethyl-pyrimidin-2-ylamino)-1,3-dihydro-indol-2-one;

5-[4-(2-Piperidin-2-yl-ethylamino)-5-trifluoromethyl-pyrimidin-2-ylamino]-1,3-dihydro-indol-2-one;

5-[4-(sobutyl-methyl-amino)-5-trifluoromethyl-pyrimidin-2-ylamino]-1,3-dihydro-indol-2-one;

N-Methyl-N-(3-{[2-(2-oxo-2,3-dihydro-1H-indol-5-ylamino)-5-trifluoromethyl-pyrimidin-4-ylamino]-methyl}-phenyl)-methanesulfonamide;

N-Ethyl-N-(3-{[2-(2-oxo-2,3-dihydro-1H-indol-5-ylamino)-5-trifluoromethyl-pyrimidin-4-ylamino]-methyl}-phenyl)-methanesulfonamide;

5-[4-(2-Methanesulfonyl-benzylamino)-5-trifluoromethyl-pyrimidin-2-ylamino]-1,3-dihydro-indol-2-one;

N-Isopropyl-N-(3-{[2-(2-oxo-2,3-dihydro-1H-indol-5-ylamino)-5-trifluoromethyl-pyrimidin-4-ylamino]-methyl}-phenyl)-methanesulfonamide;

5-{4-[(3,4,5,6-Tetrahydro-2H-[1,2]bipyridinyl-3-ylmethyl)-amino]-5-trifluoromethyl-pyrimidin-2-ylamino}-1,3-dihydro-indol-2-one;

5-{4-[(1-Pyrimidin-2-yl-piperidin-3-ylmethyl)-amino]-5-trifluoromethyl-pyrimidin-2-ylamino}-1,3-dihydro-indol-2-one;

5-{4-[2R-(1-Methanesulfonyl-piperidin-2-yl)-ethylamino]-5-trifluoromethyl-pyrimidin-2-ylamino}-1,3-dihydro-indol-2-one;

5-{4-[2S-(1-Methanesulfonyl-piperidin-2-yl)-ethylamino]-5-trifluoromethyl-pyrimidin-2-ylamino}-1,3-dihydro-indol-2-one;

5-[4-(3-Methylsulfanyl-propylamino)-5-trifluoromethyl-pyrimidin-2-ylamino]-1,3-dihydro-indol-2-one;

5-[4-(1S-Hydroxymethyl-3-methylsulfanyl-propylamino)-5-trifluoromethyl-pyrimidin-2-ylamino]-1,3-dihydro-indol-2-one;

5-[4-(2-Hydroxy-1R-methyl-ethylamino)-5-trifluoromethyl-pyrimidin-2-ylamino]-1,3-dihydro-indol-2-one;

5-[4-(1R-Hydroxymethyl-2-methyl-propylamino)-5-trifluoromethyl-pyrimidin-2-ylamino]-1,3-dihydro-indol-2-one;

N-Ethyl-N-{3-[2-(2-oxo-2,3-dihydro-1H-indol-5-ylamino)-5-trifluoromethyl-pyrimidin-4-ylamino]-propyl}-methanesulfonamide;

5-{4-[(1-Methanesulfonyl-pyrrolidin-3R-ylmethyl)-amino]-5-trifluoromethyl-pyrimidin-2-ylamino}-1,3-dihydro-indol-2-one;

5-[4-(1S-Hydroxymethyl-propylamino)-5-trifluoromethyl-pyrimidin-2-ylamino]-1,3-dihydro-indol-2-one;

5-[4-(3,5-Dinitro-benzylamino)-5-trifluoromethyl-pyrimidin-2-ylamino]-1,3-dihydro-indol-2-one;

N-(2-{[2-(2-Oxo-2,3-dihydro-1H-indol-5-ylamino)-5-trifluoromethyl-pyrimidin-4-ylamino]-methyl}-phenyl)-methanesulfonamide;

N-Isopropyl-N-{2-[2-(2-oxo-2,3-dihydro-1H-indol-5-ylamino)-5-trifluoromethyl-pyrimidin-4-ylamino]-ethyl}-methanesulfonamide;

5-[4-(2-Hydroxy-1-phenyl-ethylamino)-5-trifluoromethyl-pyrimidin-2-ylamino]-1,3-dihydro-indol-2-one;

5-[4-(1R-Hydroxymethyl-3-methyl-butylamino)-5-trifluoromethyl-pyrimidin-2-ylamino]-1,3-dihydro-indol-2-one;

5-[4-(1S-Hydroxymethyl-3-methyl-butylamino)-5-trifluoromethyl-pyrimidin-2-ylamino]-1,3-dihydro-indol-2-one;

5-{4-[(1-Methanesulfonyl-piperidin-2S-ylmethyl)-amino]-5-trifluoromethyl-pyrimidin-2-ylamino}-1,3-dihydro-indol-2-one;

5-{4-[(1-Methanesulfonyl-pyrrolidin-2R-ylmethyl)-amino]-5-trifluoromethyl-pyrimidin-2-ylamino}-1,3-dihydro-indol-2-one;

5-[4-(Methyl-pyridin-2-ylmethyl-amino)-5-trifluoromethyl-pyrimidin-2-ylamino]-1,3-dihydro-indol-2-one;

5-{4-[(3-Methanesulfonyl-benzyl)-methyl-amino]-5-trifluoromethyl-pyrimidin-2-ylamino}-1,3-dihydro-indol-2-one;

N-Methyl-N-(2-{[2-(2-oxo-2,3-dihydro-1H-indol-5-ylamino)-5-trifluoromethyl-pyrimidin-4-ylamino]-methyl}-phenyl)-methanesulfonamide;

5-[4-(Methyl-pyridin-3-ylmethyl-amino)-5-trifluoromethyl-pyrimidin-2-ylamino]-1,3-dihydro-indol-2-one;

5-{4-[(1-Methanesulfonyl-piperidin-3-ylmethyl)-methyl-amino]-5-trifluoromethyl-pyrimidin-2-ylamino}-1,3-dihydro-indol-2-one;

5-[4-(Methyl-pyridin-4-ylmethyl-amino)-5-trifluoromethyl-pyrimidin-2-ylamino]-1,3-dihydro-indol-2-one;

5-(4-Cyclopentylamino-5-trifluoromethyl-pyrimidin-2-ylamino)-1,3-dihydro-indol-2-one;

5-[4-(2,6-Dimethoxy-benzylamino)-5-trifluoromethyl-pyrimidin-2-ylamino]-1,3-dihydro-indol-2-one;

5-{4-[(1,5-Dimethyl-1H-pyrazol-3-ylmethyl)-amino]-5-trifluoromethyl-pyrimidin-2-ylamino}-1,3-dihydro-indol-2-one and 5-[4-(2-Imidazol-1-yl-ethylamino)-5-trifluoromethyl-pyrimidin-2-ylamino]-1,3-dihydro-indol-2-one.

Certain preferred embodiments of the invention are compounds selected from:

5-{4-[(1-Methanesulfonyl-piperidin-3-ylmethyl)-amino]-5-trifluoromethyl-pyrimidin-2-ylamino}-1,3-dihydro-indol-2-one;

N-Methyl-N-{2-[2-(2-oxo-2,3-dihydro-1H-indol-5-ylamino)-5-trifluoromethyl-pyrimidin-4-ylamino]-ethyl}-methanesulfonamide;

N-Methyl-N-{3-[2-(2-oxo-2,3-dihydro-1H-indol-5-ylamino)-5-trifluoromethyl-pyrimidin-4-ylamino]-propyl}-methanesulfonamide;

5-{4-[2-(1-Methanesulfonyl-piperidin-2-yl)-ethylamino]-5-trifluoromethyl-pyrimidin-2-ylamino}-1,3-dihydro-indol-2-one;

5-{4-[(Bicyclo[2.2.1]hept-5-en-2-ylmethyl)-amino]-5-trifluoromethyl-pyrimidin-2-ylamino}-1,3-dihydro-indol-2-one;

5-[4-(3-Methyl-butylamino)-5-trifluoromethyl-pyrimidin-2-ylamino]-1,3-dihydro-indol-2-one;

5-{4-[(1-Methanesulfonyl-piperidin-3-ylmethyl)-amino]-5-trifluoromethyl-pyrimidin-2-ylamino}-1,3-dihydro-indol-2-one;

N-Isopropyl-N-{3-[2-(2-oxo-2,3-dihydro-1H-indol-5-ylamino)-5-trifluoromethyl-pyrimidin-4-ylamino]-propyl}-methanesulfonamide;

N-Cyclohexyl-N-{3-[2-(2-oxo-2,3-dihydro-1H-indol-5-ylamino)-5-trifluoromethyl-pyrimidin-4-ylamino]-propyl}-methanesulfonamide;

5-{4-[2-(1-Methanesulfonyl-piperidin-2-yl)-ethylamino]-5-trifluoromethyl-pyrimidin-2-ylamino}-1,3-dihydro-indol-2-one;

N-Isopropyl-N-{2-[2-(2-oxo-2,3-dihydro-1H-indol-5-ylamino)-5-trifluoromethyl-pyrimidin-4-ylamino]-ethyl}-methanesulfonamide;

5-{4-[(1-Methanesulfonyl-pyrrolidin-2-ylmethyl)-amino]-5-trifluoromethyl-pyrimidin-2-ylamino}-1,3-dihydro-indol-2-one;

5-(4-Cyclopentylamino-5-trifluoromethyl-pyrimidin-2-ylamino)-1,3-dihydro-indol-2-one;

Ethanesulfonic acid methyl-{3-[2-(2-oxo-2,3-dihydro-1H-indol-5-ylamino)-5-trifluoromethyl-pyrimidin-4-ylamino]-propyl}-amide;

2,2,2-Trifluoro-N-methyl-N-{3-[2-(2-oxo-2,3-dihydro-1H-indol-5-ylamino)-5-trifluoromethyl-pyrimidin-4-ylamino]-propyl}-acetamide;

N-Methyl-N-{2-[2-(2-oxo-2,3-dihydro-1H-indol-5-ylamino)-5-trifluoromethyl-pyrimidin-4-ylamino]-ethyl}-methanesulfonamide;

5-(4-Cyclobutylamino-5-trifluoromethyl-pyrimidin-2-ylamino)-1,3-dihydro-indol-2-one;

5-{4-[2-Hydroxy-2-(1-methanesulfonyl-piperidin-2-yl)-ethylamino]-5-trifluoromethyl-pyrimidin-2-ylamino}-1,3-dihydro-indol-2-one;

3-Oxo-3-(3-{[2-(2-oxo-2,3-dihydro-1H-indol-5-ylamino)-5-trifluoromethyl-pyrimidin-4-ylamino]-methyl}-piperidin-1-yl)-propionitrile;

5-{4-[(1-Methanesulfonyl-piperidin-4-ylmethyl)-amino]-5-trifluoromethyl-pyrimidin-2-ylamino}-1,3-dihydro-indol-2-one;

5-{4-[(4-Methanesulfonyl-morpholin-2-ylmethyl)-amino]-5-trifluoromethyl-pyrimidin-2-ylamino}-1,3-dihydro-indol-2-one;

5-{4-[(5-Oxo-morpholin-2-ylmethyl)-amino]-5-trifluoromethyl-pyrimidin-2-ylamino}-1,3-dihydro-indol-2-one;

5-4-[(1-Methanesulfonyl-pyrrolidin-3-ylmethyl)-amino]-5-trifluoromethyl-pyrimidin-2-ylamino}-1,3-dihydro-indol-2-one;

5-[4-(3-Isopropoxy-propylamino)-5-trifluoromethyl-pyrimidin-2-ylamino]-1,3-dihydro-indol-2-one;

5-{4-[(Adamantan-2-ylmethyl)-amino]-5-trifluoromethyl-pyrimidin-2-ylamino}-1,3-dihydro-indol-2-one;

N-{2,2-Dimethyl-3-[2-(2-oxo-2,3-dihydro-1H-indol-5-ylamino)-5-trifluoromethyl-pyrimidin-4-ylamino]-propyl}-methanesulfonamide;

5-{4-[(1-Hydroxy-cyclopentylmethyl)-amino]-5-trifluoromethyl-pyrimidin-2-ylamino}-1,3-dihydro-indol-2-one;

5-{4-[(4-Hydroxy-tetrahydro-pyran-4-yl methyl)-amino]-5-trifluoromethyl-pyrimidin-2-ylamino}-1,3-dihydro-indol-2-one;

5-{4-[(2-Hydroxy-cyclohexylmethyl)-amino]-5-trifluoromethyl-pyrimidin-2-ylamino}-1,3-dihydro-indol-2-one;

5-[4-(3-Methanesulfonyl-propylamino)-5-trifluoromethyl-pyrimidin-2-ylamino]-1,3-dihydro-indol-2-one;

5-{4-[(1-Pyrimidin-2-yl-piperidin-3-ylmethyl)-amino]-5-trifluoromethyl-pyrimidin-2-ylamino}-1,3-dihydro-indol-2-one;

3-[2-(2-Oxo-2,3-dihydro-1H-indol-5-ylamino)-5-trifluoromethyl-pyrimidin-4-ylamino]-propionic acid ethyl ester;

5-{4-[(1-Ethyl-5-oxo-pyrrolidin-3-ylmethyl)-amino]-5-trifluoromethyl-pyrimidin-2-ylamino}-1,3-dihydro-indol-2-one;

2,N-Dimethyl-N-{2-[2-(2-oxo-2,3-dihydro-1H-indol-5-ylamino)-5-trifluoromethyl-pyrimidin-4-ylamino]-ethyl}-butyramide;

2-Methoxy-N-methyl-N-{3-[2-(2-oxo-2,3-dihydro-1H-indol-5-ylamino)-5-trifluoromethyl-pyrimidin-4-ylamino]-propyl}-acetamide;

5-{4-[2-(1-Acetyl-piperidin-2-yl)-ethylamino]-5-trifluoromethyl-pyrimidin-2-ylamino}-1,3-dihydro-indol-2-one;

5-{4-[(1-Methanesulfonyl-piperidin-2-ylmethyl)-amino]-5-trifluoromethyl-pyrimidin-2-ylamino}-1,3-dihydro-indol-2-one;

5-{4-[(1-Methanesulfonyl-pyrrolidin-3-ylmethyl)-amino]-5-trifluoromethyl-pyrimidin-2-ylamino}-1,3-dihydro-indol-2-one;

5-{4-[(1-Pyrimidin-2-yl-piperidin-3-ylmethyl)-amino]-5-trifluoromethyl-pyrimidin-2-ylamino}-1,3-dihydro-indol-2-one;

3-{[2-(2-Oxo-2,3-dihydro-1H-indol-5-ylamino)-5-trifluoromethyl-pyrimidin-4-ylamino]-methyl}-benzenesulfonamide;

N-(3-{[2-(2-Oxo-2,3-dihydro-1H-indol-5-ylamino)-5-trifluoromethyl-pyrimidin-4-ylamino]-methyl}-phenyl)-methanesulfonamide;

N-(4-Methoxy-3-{[2-(2-oxo-2,3-dihydro-1H-indol-5-ylamino)-5-trifluoromethyl-pyrimidin-4-ylamino]-methyl}-phenyl)-methanesulfonamide;

5-[4-(3-Methanesulfonylmethyl-benzylamino)-5-trifluoromethyl-pyrimidin-2-ylamino]-1,3-dihydro-indol-2-one;

N-Methyl-N-(4-methyl-3-{[2-(2-oxo-2,3-dihydro-1H-indol-5-ylamino)-5-trifluoromethyl-pyrimidin-4-ylamino]-methyl}-phenyl)-methanesulfonamide;

5-{4-[(4-Methanesulfonyl-pyridin-2-ylmethyl)-amino]-5-trifluoromethyl-pyrimidin-2-ylamino}-1,3-dihydro-indol-2-one;

5-{4-[(5-Methyl-furan-2-ylmethyl)-amino]-5-trifluoromethyl-pyrimidin-2-ylamino}-1,3-dihydro-indol-2-one;

(3-{[2-(2-Oxo-2,3-dihydro-1H-indol-5-ylamino)-5-trifluoromethyl-pyrimidin-4-ylamino]-methyl}-benzyl)-phosphonic acid dimethyl ester;

5-{4-[(Pyridin-2-ylmethyl)-amino]-5-trifluoromethyl-pyrimidin-2-ylamino}-1,3-dihydro-indol-2-one;

5-[5-Trifluoromethyl-4-(2-trifluoromethyl-benzylamino)-pyrimidin-2-ylamino]-1,3-dihydro-indol-2-one;

5-[4-(3-Ethanesulfonyl-benzylamino)-5-trifluoromethyl-pyrimidin-2-ylamino]-1,3-dihydro-indol-2-one;

5-{4-[(Pyrimidin-2-ylmethyl)-amino]-5-trifluoromethyl-pyrimidin-2-ylamino}-1,3-dihydro-indol-2-one;

5-{4-[(Pyrazin-2-ylmethyl)-amino]-5-trifluoromethyl-pyrimidin-2-ylamino}-1,3-dihydro-indol-2-one;

N-(4-Fluoro-3-{[2-(2-oxo-2,3-dihydro-1H-indol-5-ylamino)-5-trifluoromethyl-pyrimidin-4-ylamino]-methyl}-phenyl)-N-methyl-methanesulfonamide;

5-{4-[(Pyridin-3-ylmethyl)-amino]-5-trifluoromethyl-pyrimidin-2-ylamino}-1,3-dihydro-indol-2-one;

5-{4-[(6-Methanesulfonyl-pyridin-2-ylmethyl)-amino]-5-trifluoromethyl-pyrimidin-2-ylamino}-1,3-dihydro-indol-2-one;

5-{4-[(2-Methanesulfonylmethyl-thiazol-4-ylmethyl)-amino]-5-trifluoromethyl-pyrimidin-2-ylamino}-1,3-dihydro-indol-2-one;

5-{4-[(5-Methanesulfonyl-pyridin-3-ylmethyl)-amino]-5-trifluoromethyl-pyrimidin-2-ylamino}-1,3-dihydro-indol-2-one;

5-{4-[(3-Methyl-thiophen-2-ylmethyl)-amino]-5-trifluoromethyl-pyrimidin-2-ylamino}-1,3-dihydro-indol-2-one;

5-{4-[(1H-Imidazol-2-ylmethyl)-amino]-5-trifluoromethyl-pyrimidin-2-ylamino}-1,3-dihydro-indol-2-one;

N-Methyl-N-(3-{[2-(2-oxo-2,3-dihydro-1H-indol-5-ylamino)-5-trifluoromethyl-pyrimidin-4-ylamino]-methyl}-phenyl)-methanesulfonamide;

5-[4-(2-Methanesulfonyl-benzylamino)-5-trifluoromethyl-pyrimidin-2-ylamino]-1,3-dihydro-indol-2-one;

N-(2-{[2-(2-Oxo-2,3-dihydro-1H-indol-5-ylamino)-5-trifluoromethyl-pyrimidin-4-ylamino]-methyl}-phenyl)-methanesulfonamide;

N-Methyl-N-(2-{[2-(2-oxo-2,3-dihydro-1H-indol-5-ylamino)-5-trifluoromethyl-pyrimidin-4-ylamino]-methyl}-phenyl)-methanesulfonamide;

5-{4-[(1,5-Dimethyl-1H-pyrazol-3-ylmethyl)-amino]-5-trifluoromethyl-pyrimidin-2-ylamino}-1,3-dihydro-indol-2-one;

5-[4-(2-Imidazol-1-yl-ethylamino)-5-trifluoromethyl-pyrimidin-2-ylamino]-1,3-dihydro-indol-2-one;

N-(5-Methyl-2-{[2-(2-oxo-2,3-dihydro-1H-indol-5-ylamino)-5-trifluoromethyl-pyrimidin-4-ylamino]-methyl}-phenyl)-methanesulfonamide;

5-{4-[(3-Methyl-pyridin-2-ylmethyl)-amino]-5-trifluoromethyl-pyrimidin-2-ylamino}-1,3-dihydro-indol-2-one;

5-[4-(3-Methanesulfonyl-benzylamino)-5-trifluoromethyl-pyrimidin-2-ylamino]-1,3-dihydro-indol-2-one;

5-{4-[(Isochroman-1-ylmethyl)-amino]-5-trifluoromethyl-pyrimidin-2-ylamino}-1,3-dihydro-indol-2-one;

5-{4-[2-(Pyridin-3-yloxy)-propylamino]-5-trifluoromethyl-pyrimidin-2-ylamino}-1,3-dihydro-indol-2-one;

5-{4-[2-(6-Methyl-pyridin-2-yl)-ethylamino]-5-trifluoromethyl-pyrimidin-2-ylamino}-1,3-dihydro-indol-2-one;

5-{4-[(2,3-Dihydro-benzo[1,4]dioxin-2-ylmethyl)-amino]-5-trifluoromethyl-pyrimidin-2-ylamino}-1,3-dihydro-indol-2-one;

5-{4-[2-(4-Methyl-1H-imidazol-2-yl)-ethylamino]-5-trifluoromethyl-pyrimidin-2-ylamino}-1,3-dihydro-indol-2-one;

5-[4-[2-(1H-Benzoimidazol-2-yl)-ethylamino]-5-trifluoromethyl-pyrimidin-2-ylamino]-1,3-dihydro-indol-2-one;

5-{4-[(5-Phenyl-4H-[1,2,4]triazol-3-ylmethyl)-amino]-5-trifluoromethyl-pyrimidin-2-ylamino}-1,3-dihydro-indol-2-one;

5-{4-[(3-Methyl-imidazo[2,1-b]thiazol-6-ylmethyl)-amino]-5-trifluoromethyl-pyrimidin-2-ylamino}-1,3-dihydro-indol-2-one;

N-Methyl-N-(2-methyl-6-{[2-(2-oxo-2,3-dihydro-1H-indol-5-ylamino)-5-trifluoromethyl-pyrimidin-4-ylamino]-methyl}-phenyl)-methanesulfonamide;

N-(2-Methyl-6-{[2-(2-oxo-2,3-dihydro-1H-indol-5-ylamino)-5-trifluoromethyl-pyrimidin-4-ylamino]-methyl}-phenyl)-methanesulfonamide;

N-(3-Methanesulfonylamino-5-{[2-(2-oxo-2,3-dihydro-1H-indol-5-ylamino)-5-trifluoromethyl-pyrimidin-4-ylamino]-methyl}-phenyl)-methanesulfonamide; and N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide.

Preferred embodiment of the present invention are selected from

5-[4-(3-Methanesulfonyl-benzylamino)-5-trifluoromethyl-pyrimidin-2-ylamino]-1,3-dihydro-indol-2-one;

Ethanesulfonic acid methyl-{3-[2-(2-oxo-2,3-dihydro-1H-indol-5-ylamino)-5-trifluoromethyl-pyrimidin-4-ylamino]-propyl}-amide;

5-{4-[(Isochroman-1-ylmethyl)-amino]-5-trifluoromethyl-pyrimidin-2-ylamino}-1,3-dihydro-indol-2-one;

5-{4-[2-(Pyridin-3-yloxy)-propylamino]-5-trifluoromethyl-pyrimidin-2-ylamino}-1,3-dihydro-indol-2-one;

3-{[2-(2-Oxo-2,3-dihydro-1H-indol-5-ylamino)-5-trifluoromethyl-pyrimidin-4-ylamino]-methyl}-benzenesulfonamide;

5-{4-[(1-Methanesulfonyl-piperidin-3-ylmethyl)-amino]-5-trifluoromethyl-pyrimidin-2-ylamino}-1,3-dihydro-indol-2-one;

N-(3-{[2-(2-Oxo-2,3-dihydro-1H-indol-5-ylamino)-5-trifluoromethyl-pyrimidin-4-ylamino]-methyl}-phenyl)-methanesulfonamide;

N-Methyl-N-{2-[2-(2-oxo-2,3-dihydro-1H-indol-5-ylamino)-5-trifluoromethyl-pyrimidin-4-ylamino]-ethyl}-methanesulfonamide;

5-{4-[(4-Methanesulfonyl-morpholin-2-ylmethyl)-amino]-5-trifluoromethyl-pyrimidin-2-ylamino}-1,3-dihydro-indol-2-one;

5-[4-(3-Methanesulfonylmethyl-benzylamino)-5-trifluoromethyl-pyrimidin-2-ylamino]-1,3-dihydro-indol-2-one;

5-{4-[(1-Methanesulfonyl-pyrrolidin-3-ylmethyl)-amino]-5-trifluoromethyl-pyrimidin-2-ylamino}-1,3-dihydro-indol-2-one;

N-Methyl-N-{3-[2-(2-oxo-2,3-dihydro-1H-indol-5-ylamino)-5-trifluoromethyl-pyrimidin-4-ylamino]-propyl}-methanesulfonamide;

5-{4-[2-(1-Methanesulfonyl-piperidin-2-yl)-ethylamino]-5-trifluoromethyl-pyrimidin-2-ylamino}-1,3-dihydro-indol-2-one;

5-{4-[(4-Methanesulfonyl-pyridin-2-ylmethyl)-amino]-5-trifluoromethyl-pyrimidin-2-ylamino}-1,3-dihydro-indol-2-one;

5-[4-(3-Isopropoxy-propylamino)-5-trifluoromethyl-pyrimidin-2-ylamino]-1,3-dihydro-indol-2-one;

5-{4-[(5-Methyl-furan-2-ylmethyl)-amino]-5-trifluoromethyl-pyrimidin-2-ylamino}-1,3-dihydro-indol-2-one;

5-{4-[(Bicyclo[2.2.1]hept-5-en-2-ylmethyl)-amino]-5-trifluoromethyl-pyrimidin-2-ylamino}-1,3-dihydro-indol-2-one;

N-(4-Fluoro-3-{[2-(2-oxo-2,3-dihydro-1H-indol-5-ylamino)-5-trifluoromethyl-pyrimidin-4-ylamino]-methyl}-phenyl)-N-methyl-methanesulfonamide;

5-{4-[(1-Methanesulfonyl-piperidin-3-ylmethyl)-amino]-5-trifluoromethyl-pyrimidin-2-ylamino}-1,3-dihydro-indol-2-one;

5-{4-[(6-Methanesulfonyl-pyridin-2-ylmethyl)-amino]-5-trifluoromethyl-pyrimidin-2-ylamino}-1,3-dihydro-indol-2-one;

5-{4-[(5-Methanesulfonyl-pyridin-3-ylmethyl)-amino]-5-trifluoromethyl-pyrimidin-2-ylamino}-1,3-dihydro-indol-2-one;

5-[4-(2-Methanesulfonyl-benzylamino)-5-trifluoromethyl-pyrimidin-2-ylamino]-1,3-dihydro-indol-2-one;

5-{4-[(1-Pyrimidin-2-yl-piperidin-3-ylmethyl)-amino]-5-trifluoromethyl-pyrimidin-2-ylamino}-1,3-dihydro-indol-2-one;

5-{4-[2-(1-Methanesulfonyl-piperidin-2-yl)-ethylamino]-5-trifluoromethyl-pyrimidin-2-ylamino}-1,3-dihydro-indol-2-one;

5-{4-[2-(1-Methanesulfonyl-piperidin-2-yl)-ethylamino]-5-trifluoromethyl-pyrimidin-2-ylamino}-1,3-dihydro-indol-2-one;

N-(2-{[2-(2-Oxo-2,3-dihydro-1H-indol-5-ylamino)-5-trifluoromethyl-pyrimidin-4-ylamino]-methyl}-phenyl)-methanesulfonamide;

5-{4-[(1-Methanesulfonyl-pyrrolidin-2-ylmethyl)-amino]-5-trifluoromethyl-pyrimidin-2-ylamino}-1,3-dihydro-indol-2-one;

N-Methyl-N-(2-{[2-(2-oxo-2,3-dihydro-1H-indol-5-ylamino)-5-trifluoromethyl-pyrimidin-4-ylamino]-methyl}-phenyl)-methanesulfonamide;

N-Methyl-N-(2-methyl-6-{[2-(2-oxo-2,3-dihydro-1H-indol-5-ylamino)-5-trifluoromethyl-pyrimidin-4-ylamino]-methyl}-phenyl)-methanesulfonamide;

5-[4-(2-Hydroxy-indan-1-ylamino)-5-trifluoromethyl-pyrimidin-2-ylamino]-1,3-dihydro-indol-2-one;

5-{4-[(1-Hydroxy-cyclopentylmethyl)-amino]-5-trifluoromethyl-pyrimidin-2-ylamino}-1,3-dihydro-indol-2-one;

5-{4-[2-Hydroxy-2-(1-methanesulfonyl-piperidin-2-yl)-ethylamino]-5-trifluoromethyl-pyrimidin-2-ylamino}-1,3-dihydro-indol-2-one; and N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide.

Certain specific embodiments of the present invention include the following compounds:

N-Methyl-N-{3-[({methyl-[2-(2-oxo-2,3-dihydro-1H-indol-5-ylamino)-5-trifluoromethyl-pyrimidin-4-yl]-amino})-methyl]-phenyl}-methanesulfonamide;

N-Methyl-N-{4-methyl-3-[({methyl-[2-(2-oxo-2,3-dihydro-1H-indol-5-ylamino)-5-trifluoromethyl-pyrimidin-4-yl]-amino})-methyl]-phenyl}-methanesulfonamide;

N-(5-Methyl-2-{[2-(2-oxo-2,3-dihydro-1H-indol-5-ylamino)-5-trifluoromethyl-pyrimidin-4-ylamino]-methyl}-phenyl)-methanesulfonamide;

N-(3-Methyl-2-{[2-(2-oxo-2,3-dihydro-1H-indol-5-ylamino)-5-trifluoromethyl-pyrimidin-4-ylamino]-methyl}-phenyl)-methanesulfonamide;

N-(4-Methyl-2-{[2-(2-oxo-2,3-dihydro-1H-indol-5-ylamino)-5-trifluoromethyl-pyrimidin-4-ylamino]-methyl}-phenyl)-methanesulfonamide;

N-(2-Methyl-6-{[2-(2-oxo-2,3-dihydro-1H-indol-5-ylamino)-5-trifluoromethyl-pyrimidin-4-ylamino]-methyl}-phenyl)-methanesulfonamide;

5-[4-(3-Methanesulfonyl-propylamino)-5-trifluoromethyl-pyrimidin-2-ylamino]-1,3-dihydro-indol-2-one;

N-Methyl-N-(5-methyl-2-{[2-(2-oxo-2,3-dihydro-1H-indol-5-ylamino)-5-trifluoromethyl-pyrimidin-4-ylamino]-methyl}-phenyl)-methanesulfonamide;

N-(3-Methanesulfonylamino-5-{[2-(2-oxo-2,3-dihydro-1H-indol-5-ylamino)-5-trifluoromethyl-pyrimidin-4-ylamino]-methyl}-phenyl)-methanesulfonamide;

N-Methyl-N-(4-methyl-2-{[2-(2-oxo-2,3-dihydro-1H-indol-5-ylamino)-5-trifluoromethyl-pyrimidin-4-ylamino]-methyl}-phenyl)-methanesulfonamide;

N-Methyl-N-(2-methyl-6-{[2-(2-oxo-2,3-dihydro-1H-indol-5-ylamino)-5-trifluoromethyl-pyrimidin-4-ylamino]-methyl}-phenyl)-methanesulfonamide;

N-Methyl-N-(3-methyl-2-{[2-(2-oxo-2,3-dihydro-1H-indol-5-ylamino)-5-trifluoromethyl-pyrimidin-4-ylamino]-methyl}-phenyl)-methanesulfonamide;

5-{4-[((1S,2R)-2-Hydroxy-cyclohexylmethyl)-amino]-5-trifluoromethyl-pyrimidin-2-ylamino}-1,3-dihydro-indol-2-one;

5-[4-((1R,2S)-2-Hydroxy-indan-1-ylamino)-5-trifluoromethyl-pyrimidin-2-ylamino]-1,3-dihydro-indol-2-one;

5-[4-((S)-1-Hydroxymethyl-2-phenyl-ethylamino)-5-trifluoromethyl-pyrimidin-2-ylamino]-1,3-dihydro-indol-2-one;

N-(3-(Methanesulfonyl-methyl-amino)-5-{[2-(2-oxo-2,3-dihydro-1H-indol-5-ylamino)-5-trifluoromethyl-pyrimidin-4-ylamino]-methyl}-phenyl)-N-methyl-methanesulfonamide;

5-{4-[(1-Hydroxy-cyclopentylmethyl)-amino]-5-trifluoromethyl-pyrimidin-2-ylamino}-1,3-dihydro-indol-2-one;

N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide;

N-(3-Fluoro-2-{[2-(2-oxo-2,3-dihydro-1H-indol-5-ylamino)-5-trifluoromethyl-pyrimidin-4-ylamino]-methyl}-phenyl)-N-methyl-methanesulfonamide;

5-{4-[2-((S)-1-Methanesulfonyl-pyrrolidin-2-yl)-ethylamino]-5-trifluoromethyl-pyrimidin-2-ylamino}-1,3-dihydro-indol-2-one;

5-{4-[(1-Hydroxy-cyclobutylmethyl)-amino]-5-trifluoromethyl-pyrimidin-2-ylamino}-1,3-dihydro-indol-2-one;

5-{4-[2-((R)-1-Methanesulfonyl-pyrrolidin-2-yl)-ethylamino]-5-trifluoromethyl-pyrimidin-2-ylamino}-1,3-dihydro-indol-2-one;

N-(2-Fluoro-6-{[2-(2-oxo-2,3-dihydro-1H-indol-5-ylamino)-5-trifluoromethyl-pyrimidin-4-ylamino]-methyl}-phenyl)-N-methyl-methanesulfonamide;

N-(4-Fluoro-2-{[2-(2-oxo-2,3-dihydro-1H-indol-5-ylamino)-5-trifluoromethyl-pyrimidin-4-ylamino]-methyl}-phenyl)-N-methyl-methanesulfonamide;

N-Methyl-N-(4-{[2-(2-oxo-2,3-dihydro-1H-indol-5-ylamino)-5-trifluoromethyl-pyrimidin-4-ylamino]-methyl}-pyridin-2-yl)-methanesulfonamide;

N-2,2-Dimethyl-3-[2-(2-oxo-2,3-dihydro-1H-indol-5-ylamino)-5-trifluoromethyl-pyrimidin-4-ylamino]-propyl}-N-methyl-methanesulfonamide;

N-Methyl-N-(6-{[2-(2-oxo-2,3-dihydro-1H-indol-5-ylamino)-5-trifluoromethyl-pyrimidin-4-ylamino]-methyl}-pyridin-2-yl)-methanesulfonamide;

N-(2,4-Difluoro-6-{[2-(2-oxo-2,3-dihydro-1H-indol-5-ylamino)-5-trifluoromethyl-pyrimidin-4-ylamino]-methyl}-phenyl)-N-methyl-methanesulfonamide;

5-[4-((R)-1-Methanesulfonyl-piperidin-3-ylamino)-5-trifluoromethyl-pyrimidin-2-ylamino]-1,3-dihydro-indol-2-one;

N-Methyl-N-(6-methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(5-{[2-(2-oxo-2,3-dihydro-1H-indol-5-ylamino)-5-trifluoromethyl-pyrimidin-4-ylamino]-methyl}-pyridin-3-yl)-methanesulfonamide;

5-[4-(1-Methanesulfonyl-piperidin-4-ylamino)-5-trifluoromethyl-pyrimidin-2-ylamino]-1,3-dihydro-indol-2-one;

5-{4-[Methyl-((R)-1-phenyl-ethyl)-amino]-5-trifluoromethyl-pyrimidin-2-ylamino}-1,3-dihydro-indol-2-one;

5-(4-Benzylamino-5-trifluoromethyl-pyrimidin-2-ylamino)-1,3-dihydro-indol-2-one;

N-(4,6-Dimethyl-3-{[2-(2-oxo-2,3-dihydro-1H-indol-5-ylamino)-5-trifluoromethyl-pyrimidin-4-ylamino]-methyl}-pyridin-2-yl)-N-methyl-methanesulfonamide;

5-(4-tert-Butylamino-5-trifluoromethyl-pyrimidin-2-ylamino)-1,3-dihydro-indol-2-one;

5-[4-((1R,5S,6S)-3-Methanesulfonyl-3-aza-bicyclo[3.1.0]hex-6-ylamino)-5-trifluoromethyl-pyrimidin-2-ylamino]-1,3-dihydro-indol-2-one;

N-Methyl-N-{3-methyl-3-[2-(2-oxo-2,3-dihydro-1H-indol-5-ylamino)-5-trifluoromethyl-pyrimidin-4-ylamino]-butyl}-methanesulfonamide;

N-(6-Methyl-3-{([2-(2-oxo-2,3-dihydro-1H-indol-5-ylamino)-5-trifluoromethyl-pyrimidin-4-ylamino]-methyl}-pyridin-2-yl)-methanesulfonamide;

5-{4-[(2-Methanesulfonyl-pyridin-4-ylmethyl)-amino]-5-trifluoromethyl-pyrimidin-2-ylamino}-1,3-dihydro-indol-2-one;

2-[2-(2-Oxo-2,3-dihydro-1H-indol-5-ylamino)-5-trifluoromethyl-pyrimidin-4-ylamino]-ethanesulfonic acid amide;

N-(3-{Methyl-[2-(2-oxo-2,3-dihydro-1H-indol-5-ylamino)-5-trifluoromethyl-pyrimidin-4-yl]-amino}-propyl)-methanesulfonamide;

N-(2-{Methyl-[2-(2-oxo-2,3-dihydro-1H-indol-5-ylamino)-5-trifluoromethyl-pyrimidin-4-yl]-amino}-ethyl)-methanesulfonamide;

5-[4-(2-Methanesulfonylmethyl-benzylamino)-5-trifluoromethyl-pyrimidin-2-ylamino]-1,3-dihydro-indol-2-one;

2-[2-(2-Oxo-2,3-dihydro-1H-indol-5-ylamino)-5-trifluoromethyl-pyrimidin-4-ylamino]-ethanesulfonic acid dimethylamide;

N-Methyl-N-(3-{[2-(2-oxo-2,3-dihydro-1H-indol-5-ylamino)-5-trifluoromethyl-pyrimidin-4-ylamino]-methyl}-pyrazin-2-yl)-methanesulfonamide;

Ethanesulfonic acid methyl-(2-{[2-(2-oxo-2,3-dihydro-1H-indol-5-ylamino)-5-trifluoromethyl-pyrimidin-4-ylamino]-methyl}-phenyl)-amide;

Ethanesulfonic acid (2-{[2-(2-oxo-2,3-dihydro-1H-indol-5-ylamino)-5-trifluoromethyl-pyrimidin-4-ylamino]-methyl}-phenyl)-amide;

N-Ethyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide;

N-{1,1-Dimethyl-3-[2-(2-oxo-2,3-dihydro-1H-indol-5-ylamino)-5-trifluoromethyl-pyrimidin-4-ylamino]-propyl}-methanesulfonamide;

N-(5,6-Dimethyl-3-{[2-(2-oxo-2,3-dihydro-1H-indol-5-ylamino)-5-trifluoromethyl-pyrimidin-4-ylamino]-methyl}-pyrazin-2-yl)-N-methyl-methanesulfonamide;

5-{4-[((R)-4-Methanesulfonyl-morpholin-3-ylmethyl)-amino]-5-trifluoromethyl-pyrimidin-2-ylamino}-1,3-dihydro-indol-2-one;

Propane-1-sulfonic acid (2-{[2-(2-oxo-2,3-dihydro-1H-indol-5-ylamino)-5-trifluoromethyl-pyrimidin-4-ylamino]-methyl}-phenyl)-amide;

5-{4-[2-((R)-4-Methanesulfonyl-morpholin-3-yl)-ethylamino]-5-trifluoromethyl-pyrimidin-2-ylamino}-1,3-dihydro-indol-2-one;

Ethanesulfonic acid methyl-(3-{[2-(2-oxo-2,3-dihydro-1H-indol-5-ylamino)-5-trifluoromethyl-pyrimidin-4-ylamino]-methyl}-pyridin-2-yl)-amide;

Trifluoro-N-methyl-N-{3-[2-(2-oxo-2,3-dihydro-1H-indol-5-ylamino)-5-trifluoromethyl-pyrimidin-4-ylamino]-propyl}-methanesulfonamide;

Cyclopropanesulfonic acid methyl-{3-[2-(2-oxo-2,3-dihydro-1H-indol-5-ylamino)-5-trifluoromethyl-pyrimidin-4-ylamino]-propyl}-amide;

N-Ethyl-N-(2-{[2-(2-oxo-2,3-dihydro-1H-indol-5-ylamino)-5-trifluoromethyl-pyrimidin-4-ylamino]-methyl}-phenyl)-methanesulfonamide;

Ethanesulfonic acid methyl-(5-methyl-2-{[2-(2-oxo-2,3-dihydro-1H-indol-5-ylamino)-5-trifluoromethyl-pyrimidin-4-ylamino]-methyl}-phenyl)-amide;

Ethanesulfonic acid ethyl-(2-{[2-(2-oxo-2,3-dihydro-1H-indol-5-ylamino)-5-trifluoromethyl-pyrimidin-4-ylamino]-methyl}-phenyl)-amide;

Ethanesulfonic acid ethyl-(5-methyl-2-{[2-(2-oxo-2,3-dihydro-1H-indol-5-ylamino)-5-trifluoromethyl-pyrimidin-4-ylamino]-methyl}-phenyl)-amide;

N-Ethyl-N-(5-methyl-2-{[2-(2-oxo-2,3-dihydro-1H-indol-5-ylamino)-5-trifluoromethyl-pyrimidin-4-ylamino]-methyl}-phenyl)-methanesulfonamide;

Ethanesulfonic acid (5-methyl-2-{[2-(2-oxo-2,3-dihydro-1H-indol-5-ylamino)-5-trifluoromethyl-pyrimidin-4-ylamino]-methyl}-phenyl)-amide;

Ethanesulfonic acid (3-methyl-2-{[2-(2-oxo-2,3-dihydro-1H-indol-5-ylamino)-5-trifluoromethyl-pyrimidin-4-ylamino]-methyl}-phenyl)-amide;

Ethanesulfonic acid methyl-(3-methyl-2-{[2-(2-oxo-2,3-dihydro-1H-indol-5-ylamino)-5-trifluoromethyl-pyrimidin-4-ylamino]-methyl}-phenyl)-amide;

2-[2-(2-Oxo-2,3-dihydro-1H-indol-5-ylamino)-5-trifluoromethyl-pyrimidin-4-ylamino]-ethanesulfonic acid methylamide;

Ethanesulfonic acid {3-[2-(2-oxo-2,3-dihydro-1H-indol-5-ylamino)-5-trifluoromethyl-pyrimidin-4-ylamino]-propyl}-amide;

C-Methanesulfonyl-N-{3-[2-(2-oxo-2,3-dihydro-1H-indol-5-ylamino)-5-trifluoromethyl-pyrimidin-4-ylamino]-propyl}-methanesulfonamide;

Ethanesulfonic acid {2-[2-(2-oxo-2,3-dihydro-1H-indol-5-ylamino)-5-trifluoromethyl-pyrimidin-4-ylamino]-ethyl}-amide;

C-Methanesulfonyl-N-{2-[2-(2-oxo-2,3-dihydro-1H-indol-5-ylamino)-5-trifluoromethyl-pyrimidin-4-ylamino]-ethyl}-methanesulfonamide;

N-Methyl-N-(4-methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide;

5-(4-{[1-(2,2,2-Trifluoro-acetyl)-piperidin-3-ylmethyl]-amino}-5-trifluoromethyl-pyrimidin-2-ylamino)-1,3-dihydro-indol-2-one;

2,2,2-Trifluoro-ethanesulfonic acid {3-[2-(2-oxo-2,3-dihydro-1H-indol-5-ylamino)-5-trifluoromethyl-pyrimidin-4-ylamino]-propyl}-amide;

N-Methyl-N-(4-{[2-(2-oxo-2,3-dihydro-1H-indol-5-ylamino)-5-trifluoromethyl-pyrimidin-4-ylamino]-methyl}-pyrimidin-2-yl)-methanesulfonamide;

N-Cyclopropyl-N-(2-{[2-(2-oxo-2,3-dihydro-1H-indol-5-ylamino)-5-trifluoromethyl-pyrimidin-4-ylamino]-methyl}-phenyl)-methanesulfonamide;

N-Methyl-N-(2-{[2-(2-oxo-2,3-dihydro-1H-indol-5-ylamino)-5-trifluoromethyl-pyrimidin-4-ylamino]-methyl}-pyrimidin-4-yl)-methanesulfonamide;

N-Methyl-N-(6-{[2-(2-oxo-2,3-dihydro-1H-indol-5-ylamino)-5-trifluoromethyl-pyrimidin-4-ylamino]-methyl}-pyrazin-2-yl)-methanesulfonamide;

N-Methyl-N-(2-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(3-{[2-(2-oxo-2,3-dihydro-1H-indol-5-ylamino)-5-trifluoromethyl-pyrimidin-4-ylamino]-methyl}-pyridin-4-yl)-methanesulfonamide;

N-Cyclopropyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(6-methyl-3-{[2-(2-oxo-2,3-dihydro-1H-indol-5-ylamino)-5-trifluoromethyl-pyrimidin-4-ylamino]-methyl}-pyrazin-2-yl)-methanesulfonamide;

5-{4-[(2-Methanesulfonylmethyl-pyridin-3-ylmethyl)-amino]-5-trifluoromethyl-pyrimidin-2-ylamino}-1,3-dihydro-indol-2-one;

N-Methyl-N-(4-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(3-methyl-6-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(5-methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(4-methyl-6-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(2-methyl-5-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(5-methyl-6-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(6-methyl-2-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(5-methyl-2-{[2-(2-oxo-2,3-dihydro-1H-indol-5-ylamino)-5-trifluoromethyl-pyrimidin-4-ylamino]-methyl}-pyrimidin-4-yl)-methanesulfonamide;

N-Methyl-N-(5-methyl-2-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(4-methyl-2-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(3-methyl-4-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(5-methyl-4-{[2-(2-oxo-2,3-dihydro-1H-indol-5-ylamino)-5-trifluoromethyl-pyrimidin-4-ylamino]-methyl}-pyrimidin-2-yl)-methanesulfonamide;

N-Methyl-N-(6-methyl-5-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(6-methyl-2-{[2-(2-oxo-2,3-dihydro-1H-indol-5-ylamino)-5-trifluoromethyl-pyrimidin-4-ylamino]-methyl}-pyrimidin-4-yl)-methanesulfonamide;

N-Methyl-N-(5-methyl-4-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(2-methyl-3-{[2-(2-oxo-2,3-dihydro-1H-indol-5-ylamino)-5-trifluoromethyl-pyrimidin-4-ylamino]-methyl}-pyridin-4-yl)-methanesulfonamide;

N-Methyl-N-(6-methyl-4-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(5-methyl-3-{[2-(2-oxo-2,3-dihydro-1H-indol-5-ylamino)-5-trifluoromethyl-pyrimidin-4-ylamino]-methyl}-pyridin-4-yl)-methanesulfonamide;

N-Methyl-N-(5-methyl-6-{[2-(2-oxo-2,3-dihydro-1H-indol-5-ylamino)-5-trifluoromethyl-pyrimidin-4-ylamino]-methyl}-pyrimidin-4-yl)-methanesulfonamide;

N-Methyl-N-(5-methyl-4-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(6-{[2-(2-oxo-2,3-dihydro-1H-indol-5-ylamino)-5-trifluoromethyl-pyrimidin-4-ylamino]-methyl}-pyrimidin-4-yl)-methanesulfonamide;

N-Methyl-N-(6-methyl-4-{[2-(2-oxo-2,3-dihydro-1H-indol-5-ylamino)-5-trifluoromethyl-pyrimidin-4-ylamino]-methyl}-pyridin-2-yl)-methanesulfonamide;

N-Methyl-N-(2-methyl-4-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(5-{[2-(2-oxo-2,3-dihydro-1H-indol-5-ylamino)-5-trifluoromethyl-pyrimidin-4-ylamino]-methyl}-pyrimidin-4-yl)-methanesulfonamide;

N-Methyl-N-(2-methyl-6-{[2-(2-oxo-2,3-dihydro-1H-indol-5-ylamino)-5-trifluoromethyl-pyrimidin-4-ylamino]-methyl}-pyrimidin-4-yl)-methanesulfonamide;

N-Methyl-N-(6-methyl-4-{[2-(2-oxo-2,3-dihydro-1H-indol-5-ylamino)-5-trifluoromethyl-pyrimidin-4-ylamino]-methyl}-pyridin-3-yl)-methanesulfonamide;

N-Methyl-N-(4-{[2-(2-oxo-2,3-dihydro-1H-indol-5-ylamino)-5-trifluoromethyl-pyrimidin-4-ylamino]-methyl}-pyrimidin-5-yl)-methanesulfonamide;

N-Methyl-N-(2-methyl-5-{[2-(2-oxo-2,3-dihydro-1H-indol-5-ylamino)-5-trifluoromethyl-pyrimidin-4-ylamino]-methyl}-pyrimidin-4-yl)-methanesulfonamide;

N-Methyl-N-(4-methyl-6-{[2-(2-oxo-2,3-dihydro-1H-indol-5-ylamino)-5-trifluoromethyl-pyrimidin-4-ylamino]-methyl}-pyrimidin-5-yl)-methanesulfonamide;

N-Methyl-N-(5-methyl-6-{[2-(2-oxo-2,3-dihydro-1H-indol-5-ylamino)-5-trifluoromethyl-pyrimidin-4-ylamino]-methyl}-pyrazin-2-yl)-methanesulfonamide;

N-Methyl-N-(5-methyl-3-{[2-(2-oxo-2,3-dihydro-1H-indol-5-ylamino)-5-trifluoromethyl-pyrimidin-4-ylamino]-methyl}-pyrazin-2-yl)-methanesulfonamide;

N-Methyl-N-(2-methyl-6-{[2-(2-oxo-2,3-dihydro-1H-indol-5-ylamino)-5-trifluoromethyl-pyrimidin-4-ylamino]-methyl}-pyrimidin-5-yl)-methanesulfonamide;

N-Methyl-N-(3-methyl-6-{[2-(2-oxo-2,3-dihydro-1H-indol-5-ylamino)-5-trifluoromethyl-pyrimidin-4-ylamino]-methyl}-pyrazin-2-yl)-methanesulfonamide; and N-Methyl-N-(6-methyl-5-{[2-(2-oxo-2,3-dihydro-1H-indol-5-ylamino)-5-trifluoromethyl-pyrimidin-4-ylamino]-methyl}-pyrimidin-4-yl)-methanesulfonamide.

This invention also relates to a method for the treatment of abnormal cell growth in a mammal, including a human, comprising administering to said mammal an amount of a compound of the formula 1, as defined above, or a pharmaceutically acceptable salt, solvate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound of formula 1 that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt, solvate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the formula 1, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of formula 1, or a pharmaceutically acceptable salt, solvate or prodrug thereof, that is effective in treating abnormal cell growth in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. The invention also contemplates a pharmaceutical composition for treating abnormal cell growth wherein the composition includes a compound of formula 1, as defined above, or a pharmaceutically acceptable salt, solvate or prodrug thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a method for the treatment of a disorder associated with angiogenesis in a mammal, including a human, comprising administering to said mammal an amount of a compound of the formula 1, as defined above, or a pharmaceutically acceptable salt, solvate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of formula 1, or a pharmaceutically acceptable salt, solvate or prodrug thereof, in combination with an amount of one or more substances selected from anti-angiogenesis agents, signal transduction inhibitors, and anti-proliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxamide;

3-endo-3-[4-(4-fluoro-phenoxy)-benzenesulfonylamino]-8-oxa-bicyclo[3.2.1]octane-3-carboxylic acid hydroxamide; and 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

VEGF inhibitors, for example, SU-11248, SU-5416 and SU-6668 (Sugen Inc. of South San Francisco, Calif., USA), can also be combined with a compound of formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of formula 1. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following U.S. patent applications Ser. No.: 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

A compound of formula 1 may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application No. 60/113,647 (filed Dec. 23, 1998) which is herein incorporated by reference in its entirety.

A compound of formula I may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds of the present invention may be used alone or in combination with one or more of a variety of anti-cancer agents or supportive care agents. For example, the compounds of the present invention may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. The invention also contemplates the use of the compounds of the present invention together with hormonal therapy, e.g., exemestane (Aromasin), Lupron, anastrozole (Arimidex), tamoxifen citrate (Nolvadex), Trelstar, and combinations thereof. Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds of the invention may be used with antitumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds of the invention.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin;

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid;

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin;

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof;

Plant derived anti-tumor substances include for example those selected from mitotic inhibitors, for example vinblastine, docetaxel (Taxotere) and paclitaxel;

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof;

Immunologicals include interferons and numerous other immune enhancing agents. Interferons include interferon alpha, interferon alpha-2a, interferon, alpha-2b, interferon beta, interferon gamma-la or interferon gamma-n1. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, Provenge;

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex;

Other anticancer agents include alitretinoin, ampligen, atrasentan bexarotene, bortezomib. Bosentan, calcitriol, exisulind, finasteride,fotemustine, ibandronic acid, miltefosine, mitoxantrone, I-asparaginase, procarbazine, dacarbazine, hydroxycarbamide, pegaspargase, pentostatin, tazarotne, TLK-286, Velcade, Tarceva, or tretinoin;

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin;

Platinum-coordinated compounds include but are not limited to, cisplatin, carboplatin, nedaplatin, or oxaliplatin;

Camptothecin derivatives include but are not limited to camptothecin, 10-hydroxycamptothecin, 9-aminocamptothecin, irinotecan, SN-38, edotecarin, and topotecan;

Tyrosine kinase inhibitors are Iressa or SU5416;

Antibodies include Herceptin, Erbitux, Avastin, or Rituximab;

Interferons include interferon alpha, interferon alpha-2a, interferon, alpha-2b, interferon beta, interferon gamma-1a or interferon gamma-n1;

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex; and Other antitumor agents include mitoxantrone, I-asparaginase, procarbazine, dacarbazine, hydroxycarbamide, pentostatin, or tretinoin.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The compounds of the present invention are potent inhibitors of the FAK protein tyrosine kinases, and thus are all adapted to therapeutic use as antiproliferative agents (e.g., anticancer), antitumor (e.g., effective against solid tumors), antiangiogenesis (e.g., stop or prevent proliferationation of blood vessels) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

In one preferred embodiment of the present invention cancer is selected from lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

In a more preferred embodiment cancer is selected a solid tumor, such as, but not limited to, breast, lung, colon, brain, prostate, stomach, pancreatic, ovarian, skin (melanoma), endocrine, uterine, testicular, and bladder.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

A particular aspect of this invention is directed to methods for treating or preventing a condition that presents with low bone mass in a mammal (including a human being) which comprise administering to a mammal in need of such treatment a condition that presents with low bone mass treating amount of a Formula I compound or a pharmaceutically acceptable salt of said compound.

This invention is particularly directed to such methods wherein the condition that presents with low bone mass is osteoporosis, frailty, an osteoporotic fracture, a bone defect, childhood idiopathic bone loss, alveolar bone loss, mandibular bone loss, bone fracture, osteotomy, periodontitis or prosthetic ingrowth.

A particular aspect of this invention is directed to methods for treating osteoporosis in a mammal (including a human being) which comprise administering to a mammal in need of such treatment an osteoporosis treating amount of a Formula I compound or a pharmaceutically acceptable salt of said compound.

Another aspect of this invention is directed to methods for treating a bone fracture or an osteoporotic fracture in a mammal which comprise administering to a mammal in need of such treatment a bone fracture treating or an osteoporotic fracture treating amount of a Formula I compound or a pharmaceutically acceptable salt of said compound.

The term "osteoporosis" includes primary osteoporosis, such as senile, postmenopausal and juvenile osteoporosis, as well as secondary osteoporosis, such as osteoporosis due to hyperthyroidism or Cushing syndrome (due to corticosteroid use), acromegaly, hypogonadism, dysosteogenesis and hypophospatasemia.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 1 mg to 1 gram, preferably 1 mg to 250 mg, more preferably 10 mg to 100 mg.

The present invention also encompasses sustained release compositions.

DETAILED DESCRIPTION OF THE INVENTION

The compounds of formula 1 can be prepared using the synthetic route outlined in Scheme 1. The substituents in Scheme 1 have the same meaning as the substituents defined for formula 1.

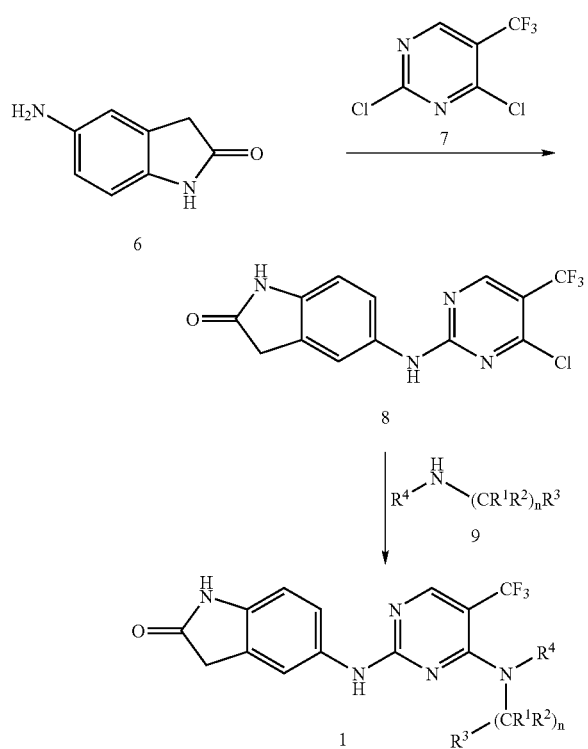

Compounds of formula 1 can be prepared starting from the 5-amino-oxindole (6) and pyrimidine (7). Combining 7 with a Lewis Acid at temperatures ranging from −15 to 45° C. for a time period of 10–60 minutes in an inert solvent (or solvent mixture) followed by addition of 6 and a suitable base provides after the period of 1–24 hours the intermediate 4-chloropyrimidine (8) in high yields. Examples of inert solvents include but are not limited to THF, 1,4-dioxane, n-BuOH, i-PrOH, dichloromethane and 1,2-dichloroethane. Examples of suitable bases employed may include but are not limited to (i) non-nucleophilic organic bases for example triethylamine or diisopropylethylamine (ii) inorganic bases such as potassium carbonate or cesium carbonate or (iii) resin bound bases such as MP-carbonate.

Examples of Lewis Acids include but are not limited to halide salts of magnesium, copper, zinc, tin or titanium. In the next reaction, intermediate 8 is reacted with an amine of the formula 9 either neat or in the presence of an inert solvent (or solvent mixture) at temperatures ranging from 0 to 150° C. to provide the compounds of formula 1. Optionally this reaction can be run in the presence of a suitable base. Examples of suitable solvents for this reaction include but are not limited to THF, 1,4-dioxane, DMF, N-methylpyrrolidinone, EtOH, n-BuOH, i-PrOH, dichloromethane, 1,2-dichloroethane, DMSO or acetonitrile. Suitable bases are as outlined above.

Compounds of the present invention may be synthetically transformed into other compounds of the invention by techniques known to those skilled in the art. Simply for illustrative purposes and without limitation, such methods include:

a) removal of a protecting group by methods outlined in T. W. Greene and P. G. M. Wuts, "Protective Groups in Organic Synthesis", Second Edition, John Wiley and Sons, New York, 1991; e.g., emoval of a BOC protecting group with an acid source such as HCl or trifluoroacetic acid;

b) displacement of a leaving group (halide, mesylate, tosylate, etc) with functional groups such as but not limited to a primary or secondary amine, thiol or alcohol to form a secondary or tertiary amine, thioether or ether, respectively;

c) treatment of phenyl (or substituted phenyl) carbamates with primary of secondary amines to form the corresponding ureas as in Thavonekham, B et. al. Synthesis (1997), 10, p 1189;

d) reduction of propargyl or homopropargyl alcohols or N-BOC protected primary amines to the corresponding E-allylic or E-homoallylic derivatives by treatment with sodium bis(2-methoxyethoxy)aluminum hydride (Red-Al) as in Denmark, S. E.; Jones, T. K. J. Org. Chem. (1982) 47, 4595–4597 or van Benthem, R. A. T. M.; Michels, J. J.; Speckamp, W. N. Synlett (1994), 368–370;

e) reduction of alkynes to the corresponding Z-alkene derivatives by treatment hydrogen gas and a Pd catalyst as in Tomassy, B. et. al. Synth. Commun. (1998), 28, p 1201;

f) treatment of primary and secondary amines with an isocyanate, acid chloride (or other activated carboxylic acid derivative), alkyl/aryl chloroformate or sulfonyl chloride to provide the corresponding urea, amide, carbamate or sulfonamide;

g) reductive amination of a primary or secondary amine using an aldehyde or ketone and an appropriate reducing reagent;

h) treatment of alcohols with an isocyanate, acid chloride (or other activated carboxylic acid derivative), alkyl/aryl chloroformate or sulfonyl chloride to provide the corresponding carbamate, ester, carbonate or sulfonic acid ester.

Amines of the formula 9 may be purchased and used directly or alternatively be prepared by one skilled in the art using ordinary chemical transformations. For example; arylalkylamines or heteroarylalkylamines may be prepared from the corresponding nitrile by catalytic hydrogenation using catalysts such as Pd/C or Raney Nickel or by lithium aluminum hydride reduction, (see Rylander, Catalytic Hydrogenation in Organic Synthesis, Academic Press, 1979).

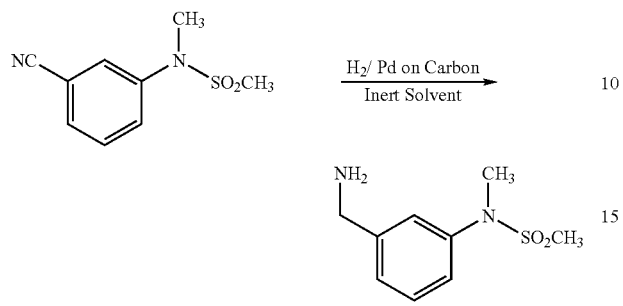

The nitrile starting materials can be either purchased or prepared from the corresponding aryl/heteroaryl bromide, iodide or triflate and Zn(CN)2 using Pd coupling conditions found in Tschaen, D. M., et. al Synthetic Communications (1994), 24, 6, pp 887–890.

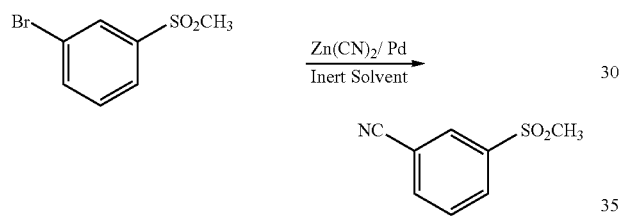

Alternatively, benzylamines or heteroarylmethylamines can be prepared by reacting the appropriate arylalkyl or heteroarylalkyl halide and the potassium salt of (BOC)$_2$NH (reference) and subsequent removal of the BOC groups with acid.

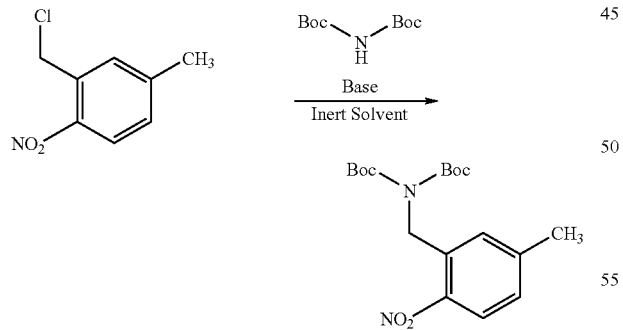

Amines, protected forms of amines, precursors to amines and precursors to the protected forms of amines of formula 9 can be prepared by combining the appropriate alkyne, or alkenyl stannane, alkenyl borane, alkenyl boronic acid, boronic ester with the appropriate aryl or heteroaryl bromide, iodide or triflate using Pd coupling conditions as found in Tsuji, J.; Palladium Reagents and Catalysis, John Wiley and Sons 1999 and references cited therein.

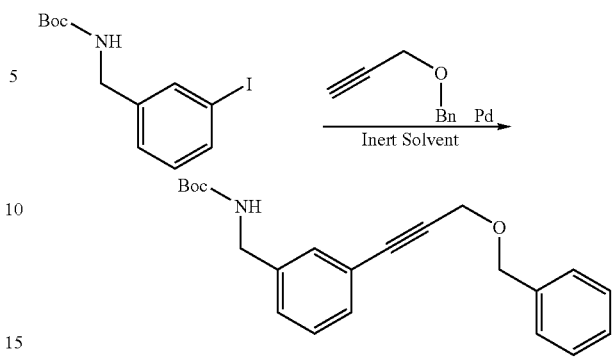

Appropriately protected amines of formula 9 may be converted to different amines of formula 9 according to methods familiar to those skilled in the art for exampleas but limited to:

(a) oxidation of a thioether to a sulfoxide or sulfone.

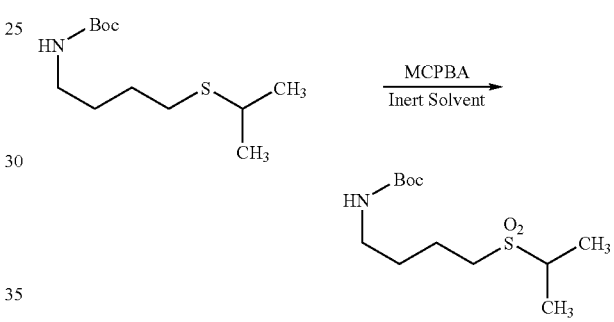

(b) N-alkylation of a sulfanilide can be achieved under phase transfer using conditions described by Brehme, R. "Synthesis", (1976), pp 113–114.

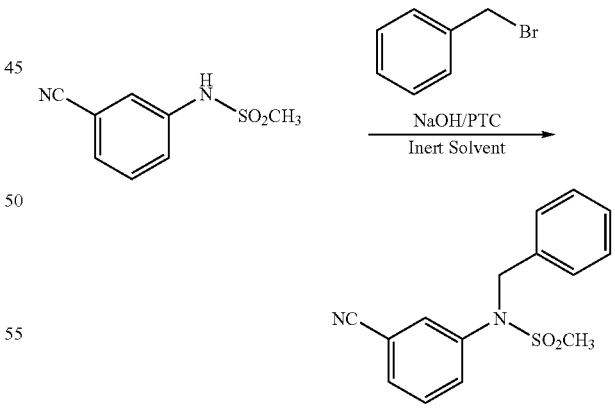

As understood by those skilled in the art, the chemical transformation to convert an aryl halide or triflate or heteroaryl halide or triflate to an aromatic or heteroaromatic amine may be carried out using conditions currently outlined in the literature, see Hartwig, J. F.: "Angew. Chem. Int. Ed." (1998), 37, pp. 2046–2067, Wolfe, J. P.; Wagaw, S.; Marcoux, J. F.; Buchwald, S. L.; "Acc. Chem. Res.", (1998), 31, pp 805–818, Wolfe, J. P.; Buchwald, S. L.; "J. Org. Chem.", (2000), 65, pp 1144–1157, Muci, A. R.; Buchwald, S. L.; "Topics in Current Chemistry" (2002), pp 131–209 and references cited therein. Further, as understood by those skilled in the art, these same aryl or heteroaryl aminatiion chemical transformations may alternatively be carried out on nitrile (or primary amide) precursors which provide amines of the formula 5 after nitrile (or amide) reduction. Protected amines of formula 5 may be further converted to different amines of formula 5 according to methods familiar to those skilled in the art.

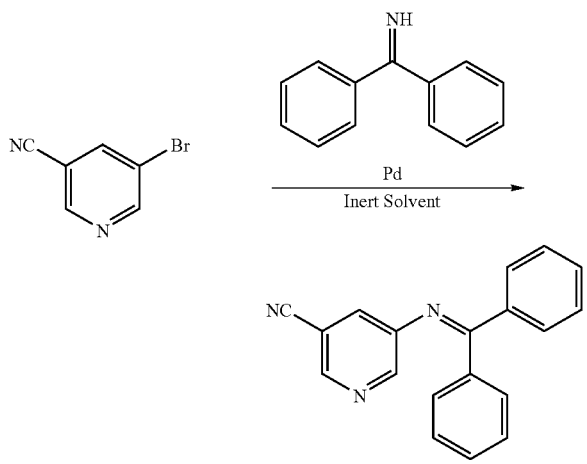

The in vitro activity of the compounds of formula 1 may be determined by the following procedure. More particularly, the following assay provides a method to determine whether compounds of the formula 1 inhibit the tyrosine kinase activity of the catalytic construct FAK(410-689). The assay is an ELISA-based format, measuring the inhibition of poly-glu-tyr phosphorylation by FAK(410-689).

The assay protocol has three parts:
I. Purification and cleavage of His-FAK(410-689)
II. FAK410-689 (a.k.a. FAKcd) Activation
III. FAKcd Kinase ELISA Materials:
  Ni-NTA agarose (Qiagen)
  XK-16 column (Amersham-Pharmacia)
  300 mM Imidizole
  Superdex 200 HiLoad 16/60 prep grade column (Amersham Biotech.)
  Antibody: Anti-Phosphotyrosine HRP-Conjugated Py20 (Transduction labs)
  FAKcd: Purified and activated in house
  TMB Microwell Peroxidase Substrate (Oncogene Research Products #CL07)
  BSA: Sigma #A3294
  Tween-20: Sigma #P1379
  DMSO: Sigma #D-5879
  D-PBS: Gibco #14190-037

Reagents for Purification:
  Buffer A: 50 mM HEPES pH 7.0
  500 mM NaCl
  0.1 mM TCEP
  Complete™ protease inhibitor cocktail tablets (Roche)
  Buffer B: 25 mM HEPES pH 7.0
  400 mM NaCl
  0.1 mM TCEP
  Buffer C: 10 mM HEPES pH 7.5
  200 mM Ammonium Sulfate
  0.1 mM TCEP Reaqents for Activation
  FAK(410-689): 3 tubes of frozen aliquots at 150 ul/tube for a total of 450 ul at 1.48 mg/ml (660 ug)
  His-Src(249-524): ~0.74 mg/ml stock in 10 mM HEPES, 200 mM (NH4)2SO4
  Src reaction buffer (Upstate Biotech):
  100 mM Tris-HCl pH7.2
  125 mM MgCl2
  25 mM MnCl2
  2 mM EDTA
  250 uM Na3VO4
  2 mM DTT
  Mn2+/ATP cocktail (Upstate Biotech)
  75 mM MnCl2
  500 uM ATP
  20 mM MOPS pH 7.2
  1 mM Na3VO4
  25 mM □-glycerol phosphate
  5 mM EGTA
  1 mM DTT
  ATP: 150 mM stock
  MgCl$_2$: 1 M Stock
  DTT: 1 M stock Reagents for FAKcd Kinase ELISA
  Phosphorylation Buffer:
  50 mM HEPES, pH 7.5
  125 mM NaCl
  48 mM MgCl2
  Wash Buffer: TBS+0.1% Tween-20.
  Blocking Buffer:
  Tris Buffer Saline
  3% BSA
  0.05% Tween-20, filtered
  Plate Coating Buffer:
  50 mg/ml Poly-Glu-Tyr (Sigma #P0275) in Phosphate buffer Saline (DPBS).
  ATP: 0.1M ATP in H2O or HEPES, pH7
  Note: ATP Assay Buffer:
  Make up as 75 uM ATP in PBS, so that 80 ul in 120 ul reaction volume=50 uM final ATP concentration.

I. Purification of His-FAKcd(410-689)
  1. Resuspend 130 g baculovirus cell paste containing the over expressed His-FAKcd410-689 recombinant protein in 3 volumes (400 ml) of Buffer A.
  2. Lyse cells with one pass on a microfluidizer.
  3. Remove cell debris by centrifugation at 4° C. for 35 minutes at 14,000 rpm in a Sorval SLA-1500 rotor.
  4. Transfer the supernatant to a clean tube and add 6.0 ml of Ni-NTA agarose (Qiagen).
  5. Incubate the suspension with gentle rocking at 4° C. for 1 hour.
  6. Centrifuge suspension at 700×g in a swinging bucket rotor.
  7. Discard the supernatant and resuspend the agarose beads in 20.0 ml of Buffer A.
  8. Transfer the beads to an XK-16 column (Amersham-Pharmacia) connected to a FPLCA™.
  9. Wash the agarose-beads with 5 column volumes of Buffer A and elute off the column with a step gradient of Buffer A containing 300 mM Imidizole.
  10. Perform a buffer exchange of the eluted fractions into Buffer B.

11. Following buffer exchange, pool the fractions and add thrombin at a 1:300 (w/w) ratio and incubated overnight at 13° C. to remove the N-terminal His-tag (His-FAK410-698→FAK410-689 (a.k.a. FAKcd)).

12. Add the reaction mixture back onto the Ni-NTA column equilibrated with Buffer A and collect the flow-through.

13. Concentrate the flow-through down to 1.7 ml and load directly onto a Superdex 200 HiLoad 16/60 prep grade column equilibrated with Buffer C. The desired protein elutes between 85–95 ml.

14. Aliquot the FAKcd protein and store frozen at –80° C.

II. FAK activation

1. To 450 ul of FAK(410-689) at 1.48 mg/ml (660 ug) add the following:
   30 ul of 0.037 mg/ml (1 uM) His-Src(249-524)
   30 ul of 7.5 mM ATP
   12 ul of 20 mM MgCl2
   10 ul Mn2+/ATP cocktail (UpState Biotech.)
   4 ul of 6.7 mM DTT
   60 ul Src Reaction Buffer (UpState Biotech.)

2. Incubate Reaction for at least 3 hours at room temperature

At time $t_0$, almost all of the FAK(410-689) is singly phosphorylated. The second phosphorylation is slow. At $t_{120}$ (t=120 minutes), add 10 ul of 150 mM ATP.

$T_0$=(Start) 90% singly phosphorylated FAK(410-689) (1 PO4)

$T_{43}$=(43 min) 65% singly phosphorylated (1 PO4), 35% doubly phosphorylated (2 PO4)

$T_{90}$=(90 min) 45% 1 PO4, 55% 2 PO4

$T_{150}$=15% 1 PO4, 85% 2 PO4

$T_{210}$=<10% 1 PO4, >90% 2 PO4 desalted sample

3. Add 180 ul aliquots of the desalted material to NiNTA spin column and incubate on spin column 4. Spin at 10 k rpm (microfuge), for 5 minutes to isolate and collect flow through (Activated FAK(410-689)) and remove His-Src (captured on column)

III. FAKcd Kinase ELISA

1. Coat 96-well Nunc MaxiSorp plates with poly-glu-tyr (pGT) at 10 ug/well: Prepare 10 ug/ml of pGT in PBS and aliquot 100 ul/well. Incubate the plates at 37° C. overnight, aspirate the supernatant, wash the plates 3 times with Wash Buffer, and flick to dry before storing at 4° C.

2. Prepare compound stock solutions of 2.5 mM in 100% DMSO. The stocks are subsequently diluted to 60× of the final concentration in 100% DMSO, and diluted 1:5 in Kinase Phosphorylation Buffer.

3. Prepare a 75 uM working ATP solution in Kinase phosphorylation buffer. Add 80 ul to each well for a final ATP concentration of 50 uM.

4. Transfer 10 ul of the diluted compounds (0.5 log serial dilutions) to each well of the pGT assay plate, running each compound in triplicates on the same plate.

5. Dilute on ice, FAKcd protein to 1:1000 in Kinase Phosphorylation Buffer. Dispense 30 ul per well.

6. Note: Linearity and the appropriate dilution must be pre-determined for each batch of protein. The enzyme concentration selected should be such that quantitation of the assay signal will be approximately 0.8–1.0 at OD450, and in the linear range of the reaction rate.

7. Prepare both a No ATP control (noise) and a No Compound Control (Signal):

8. (Noise) One blank row of wells receives 10 ul of 1:5 diluted compounds in DMSO, 80 ul of Phosphorylation buffer (minus ATP), and 30 ul FAKcd solution.

9. (Signal) Control wells receive 10 ul of 1:5 diluted DMSO (minus Compound) in Kinase phosphorylation buffer, 80 ul of 75 uM ATP, and 30 ul of 1:1000 FAKcd enzyme.

10. Incubate reaction at room temperature for 15 minutes with gentle shaking on a plate shaker.

11. Terminate the reaction by aspirating off the reaction mixture and washing 3 times with wash buffer.

12. Dilute phospho-tyrosine HRP-conjugated (pY20HRP) antibody to 0.250 ug/ml (1:1000 of Stock) in blocking buffer. Dispense 100 ul per well, and incubate with shaking for 30 minutes at R.T.

13. Aspirate the supernatant and wash the plate 3 times with wash buffer.

14. Add 100 ul per well of room temperature TMB solution to initiate color development. Color development is terminated after approximately 15–30 sec. by the addition of 100 ul of 0.09M H2SO4 per well.

15. The signal is quantitated by measurement of absorbance at 450 nm on the BioRad microplate reader or a microplate reader capable of reading at OD450.

16. Inhibition of tyrosine kinase activity would result in a reduced absorbance signal. The signal is typically 0.8–1.0 OD units. The values are reported as $IC_{50}$s, uM concentration.

FAK Inducible cell-based ELISA: Final Protocol

Materials:
Reacti-Bind Goat Anti-Rabbit Plates 96-well (Pierce Product#15135ZZ @115.00 USD)
FAKpY397 rabbit polyclonal antibody (Biosource #44624 @315.00 USD)
ChromePure Rabbit IgG, whole molecule (Jackson Laboratories #001-000-003 @60/25 mg USD)
UBI αFAK clone 2A7 mouse monoclonal antibody (Upstate#05-182 @ 289.00 USD)
Peroxidase-conjugated AffiniPure Goat Anti-Mouse IgG (Jackson Labs #115-035-146 @95/1.5 ml USD)
SuperBlock TBS (Pierce Product#37535ZZ @99 USD)
Bovine Serum Albumin (Sigma #A-9647 @117.95/100 g USD)
TMB Peroxidase substrate (Oncogene Research Products #CL07-100 ml @40.00 USD)
Na3VO4 Sodium Orthovanadate (Sigma #S6508 @43.95/50 g USD)
MTT substrate (Sigma # M-2128 @25.95/500 mg USD)
Growth Media: DMEM+10% FBS, P/S, Glu, 750 ug/ml Zeocin and 50 ug/ml Hygromycin (Zeocin InVitrogen #R250-05 @ 725 USD and Hygromycon InVitrogen #R220-05 @ 150 USD)
Mifepristone InVitrogen # H 110-01 @ 125 USD
Complete EDTA-free Protease Inhibitor pellet Boehringer Mannheim #1873580

FAK cell-based Protocol for selectivity of kinase-dependent phosphoFAKY397

Procedure:
An inducible FAK cell-based assay in ELISA format for the screening of chemical matter to identify tyrosine kinase specific inhibitors was developed. The cell-based assay exploits the mechanism of the GeneSwitch™ system (InVitrogen) to exogenously control the expression and phosphorylation of FAK and the kinase-dependent autophosphorylation site at residue Y397.

Inhibition of the kinase-dependent autophosphorylation at Y397 results in a reduced absorbance signal at OD450. The signal is typically 0.9 to 1.5 OD450 units with the noise falling in the range of 0.08 to 0.1 OD450 units. The values are reported as $IC_{50}$s, uM concentration.

On day 1, grow A431•FAKwt in T175 flasks. On the day prior to running the FAK cell-assay, seed A431•FAKwt cells in growth media on 96-well U-bottom plates. Allow cells to sit at 37° C., 5% CO2 for 6 to 8 hours prior to FAK induction. Prepare Mifepristone stock solution of 10 uM in 100% Ethanol. The stock solution is subsequently diluted to 10× of the final concentration in Growth Media. Transfer 10 ul of this dilution (final concentration of 0.1 nM Mifepristone) into each well. Allow cells to sit at 37° C., 5% CO2 overnight (12 to 16 hours). Also, prepare control wells without Mifepristone induction of FAK expression and phosphorylation.

On day 2, coat Goat Anti-Rabbit plate(s) with 3.5 ug/ml of phosphospecific FAKpY397 polyclonal antibody prepared in SuperBlock TBS buffer, and allow plate(s) to shake on a plate shaker at room temperature for 2 hours. Optionally, control wells may be coated with 3.5 ug/ml of control Capture antibody (Whole Rabbit IgG molecules) prepared in SuperBlock TBS. Wash off excess FAKpY397 antibody 3 times using buffer. Block Anti-FAKpY397 coated plate(s) with 200 ul per well of 3% BSA/0.5% Tween Blocking buffer for 1 hour at room temperature on the plate shaker. While the plate(s) are blocking, prepare compound stock solutions of 5 mM in 100% DMSO. The stock solutions are subsequently serially diluted to 100× of the final concentration in 100% DMSO. Make a 1:10 dilution using the 10× solution into growth media and transfer 10 ul of the appropriate compound dilutions to each well containing either the FAK induced or uninduced control A431 cells for 30 minutes at 37° C., 5% CO2. Prepare RIPA lysis buffer (50 mM Tris-HCl, pH7.4, 1% NP-40, 0.25% Na-deoxycholate, 150 mM NaCl, 1 mM EDTA, 1 mM Na3VO4, 1 mM NaF, and one CompleteTM EDTA-free protease inhibitor pellet per 50 ml solution). At the end of 30 minutes compound treatment, wash off compound 3 times using TBS-T wash buffer. Lyse cells with 100 ul/well of RIPA buffer.

To the coated plate, remove blocking buffer and wash 3 times using TBS-T wash buffer. Using a 96-well automated microdispenser, transfer 100 ul of whole cell-lysate (from step 6) to the Goat Anti-Rabbit FAKpY397 coated plate(s) to capture phosphoFAKY397 proteins. Shake at room temperature for 2 hours. Wash off unbound proteins 3 times using TBS-T wash buffer. Prepare 0.5 ug/ml (1:2000 dilution) of UBI αFAK detection antibody in 3% BSA/0.5% Tween blocking buffer. Dispense 100 ul of UBI αFAK solution per well and shake for 30 minutes at room temperature. Wash off excess UBI αFAK antibody 3 times using TBS-T wash buffer. Prepare 0.08 ug/ml (1:5000 dilution) of secondary Anti-Mouse Peroxidase (Anti-2MHRP) conjugated antibody. Dispense 100 ul per well of the Anti-2MHRP solution and shake for 30 minutes at room temperature. Wash off excess Anti-2MHRP antibody 3 times using TBS-T wash buffer. Add 100 ul per well of room temperature TMB substrate solution to allow for color development. Terminate the TMB reaction with 100 ul per well of TMB stop solution (0.09M H2SO4) and quantitate the signal by measurement of absorbance at 450 nm on the BioRad microplate reader.

Additional FAK cell assays are hereby incorporated by reference from Pfizer Provisional Application No. 60/412,078 entitled "INDUCIBLE FOCAL ADHESION KINASE CELL ASSAY".

In a preferred embodiment, the compounds of the present invention have an in vitro activity as determined by a kinase assay, e.g., such as that described herein, of less than 500 nM. Preferably, the compounds have an $IC_{50}$ of less than 25 nM in the kinase assay, and more preferably less than 10 nM. In a further preferred embodiment, the compounds exhibit an $IC_{50}$ in a FAK cell based assay, e.g., such as that described herein, of less than 1 μM, more preferably less than 100 nM, and most preferably less than 25 nM.

Still further, the following assay(s) may be used to assess the ability of a compound of the present invention to inhibit osteoporosis and/or low bone mass, as described above.

(1) Effect of Test Compound on Body Weight, Body Composition and Bone Density in the Aged Intact and Ovariectomized Female Rat This assay may be used to test the effects of a test compound in aged intact or ovariectomized (OVX) female rat model.

Study Protocol

Sprague-Dawley female rats are sham-operated or OVX at 18 months of age, while a group of rats is necropsied at day 0 to serve as baseline controls. One day post-surgery, the rats are treated with either vehicle or test compound. The vehicle or test compound is administered twice a week (Tuesday and Friday) by subcutaneous injection (s.c.), with the test compound being administered at an average dose of 10 milligrams per kilogram of body weight per day (10 mg/kg/day).

All rats are given s.c. injection of 10 mg/kg of calcein (Sigma, St. Louis, Mo.) for fluorescent bone label 2 and 12 days before necropsy. On the day of necropsy, all rats under ketamine/xylazine anesthesia are weighed and undergoe dual-energy X-ray absorptiometry (DXA, QDR4500/W, Hologic Inc., Waltham, Mass.) equipped with Rat Whole Body Scan software for lean and fat body mass determination. The rats are necropsied, then autopsied and blood is obtained by cardiac puncture. The distal femoral metaphysis and femoral shafts from each rat are analyzed by peripheral quantitative computerized tomography (pQCT), and volumetric total, trabecular and cortical bone mineral content and density are determined.

Peripheral Quantitative Computerized Tomography (pQCT) Analysis: Excised femurs are scanned by a pQCT X-ray machine (Stratec XCT Research M, Norland Medical Systems, Fort Atkinson, Wis.) with software version 5.40. A 1 millimeter (mm) thick cross section of the femur metaphysis is taken at 5.0 mm (proximal femoral metaphysis, a primary cancellous bone site) and 13 mm (femoral shafts, a cortical bone site) proximal from the distal end with a voxel size of 0.10 mm. Cortical bone is defined and analyzed using contour mode 2 and cortical mode 4. An outer threshold setting of 340 mg/cm$^3$ is used to distinguish the cortical shell from soft tissue and an inner threshold of 529 mg/cm$^3$ to distinguish cortical bone along the endocortical surface. Trabecular bone is determined using peel mode 4 with a threshold of 655 mg/cm$^3$ to distinguish (sub)cortical from cancellous bone. An additional concentric peel of 1% of the defined cancellous bone is used to ensure that (sub)cortical bone is eliminated from the analysis. Volumetric content, density, and area are determined for both trabecular and cortical bone (Jamsa T. et al., Bone 23:155–161, 1998; Ke, H. Z. et al., *Journal of Bone and Mineral Research*, 16:765–773, 2001).

Vaginal histology: Vaginal tissue is fixed and embedded in paraffin. Five micron sections are cut and stained with Alcian Blue staining. Histology examination of vaginal luminal epithelial thickness and mucopolysaccharide (secreted cells) is performed.

The experimental groups for the protocol are as follows:
Group I: Baseline controls
Group II: Sham+Vehicle
Group III: OVX+Vehicle
Group IV: OVX+Test Compound at 10 mg/kg/day (in Vehicle)

(2) Fracture Healing Assays (a) Assay for Effects on Fracture Healing after Systemic Administration Fracture Technique: Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10–12 animals per each subgroup per time point for testing the fracture healing. The first group receives daily gavage of vehicle (water: 100% Ethanol=95:5) at 1 ml/rat, while the others receive daily gavage from 0.01 to 100 mg/kg/day of the compound to be tested (1 ml/rat) for 10, 20, 40 and 80 days.

At 10, 20, 40 and 80 days, 10–12 rats from each group are anesthetized with Ketamine and sacrificed by exsanguination. Both tibiofibular bones are removed by dissection and all soft tissue is stripped. Bones from 5–6 rats for each group are stored in 70% ethanol for histological analysis, and bones from another 5–6 rats for each group are stored in a buffered Ringer's solution (+4° C., pH 7.4) for radiographs and biomechanical testing which is performed.

Histological Analysis: The methods for histologic analysis of fractured bone have been previously published by Mosekilde and Bak (The Effects of Growth Hormone on Fracture Healing in Rats: A Histological Description. Bone, 14:19–27, 1993). Briefly, the fracture site is sawed 8 mm to each side of the fracture line, embedded undecalcified in methymethacrylate, and cut frontals sections on a Reichert-Jung Polycut microtome in 8 μm thick. Masson-Trichrome stained mid-frontal sections (including both tibia and fibula) are used for visualization of the cellullar and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

(b) Assay for Effects on Fracture Healing after Local Administration

Fracture Technique: Female or male beagle dogs at approximately 2 years of age are used under anesthesia in the study. Transverse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499–507; 1985). A wire is pulled through the fracture site to ensure complete anatomical disruption of the bone. Thereafter, local delivery of prostaglandin agonists to the fracture site is achieved by slow release of compound delivered by slow release pellets or by administration of the compounds in a suitable formulation such as a paste gel solution or suspension for 10, 15, or 20 weeks.

Histological Analysis: The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of alendronate on fracture healing and bone remodeling in dogs. J. Orthop. Res. 14:74–70, 1996) and Mosekilde and Bak (The Effects of Growth Hormone on Fracture Healing in Rats: A Histological Description. Bone, 14:19–27, 1993). Briefly, after sacrifice, the fracture site is sawed 3 cm to each side of the fracture line, embedded undecalcified in methymethacrylate, and cut on a Reichert-Jung Polycut microtome in 8 μm thick of frontal sections. Masson-Trichrome stained mid-frontal sections (including both tibia and fibula) are used for visualization of the cellullar and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs. J. Orthop. Res. 14:74–70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxo-quinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodexe (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Where HPLC chromatography is referred to in the preparations and examples below, the general conditions used, unless otherwise indicated, are as follows. The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 mL/minute.

EXAMPLES

General Methods:

Preparation of 5-nitro-oxindole

To a solution of oxindole (26 g) in 100 mL of concentrated sulfuric acid at −15° C. was added fuming nitric acid (8.4 mL) dropwise. Careful attention was paid to maintain the reaction temperature at −15° C. After the addition was complete, the reaction was stirred for 30 minutes and then poured into ice water. A yellow precipitate was formed which was isolated by filtration to provide 34 grams (98%) of 5-nitro oxindole.

Preparation of 5-amino-oxindole (2)

To a solution of 5-nitro-oxindole (25 g) in 120 mL of dimethylacetamide in a Parr bottle was added 10% Pd/C (0.5 g). The mixture was hydrogenated (40 psi H2) for 16 hours. The catalyst was removed by filtration and the filtrate was diluted with ether (2 L) to provide 5-amino-oxindole (10.5 g; 50%).

Preparation of 2.4-dichloro-5-trifluoromethylpyrimidine (3)

5-Trifluoromethyluracil (250 g, 1.39 mol) and phosphorous oxychloride (655 mL, 6.94 mol, 5 equiv) were charged to a 3 L 4-neck flask equipped with overhead stirrer, a reflux condenser, an addition funnel and an internal theromocouple. The contents were maintained under a nitrogen atmosphere as concentrated phosphoric acid (85 wt %, 9.5 mL, 0.1 equiv) was added in one portion to the slurry, resulting in a moderate exotherm. Diisopropylethylamine (245 mL, 1.39 mol, 1 equiv) was then added dropwise over 15 minutes at such a rate that the internal temperature of the reaction reached 85–90° C. by the end of the addition. By the end of the amine addition the reaction mixture was a homogenous light-orange solution. Heating was initiated and the orange solution was maintained at 100° C. for 20 hours, at which time HPLC analysis of the reaction mixture indicated that the starting material was consumed. External heating was removed and the contents of the flask were cooled to 40° C. and then added dropwise to a cooled mixture of 3N HCl (5 L, 10 equiv) and diethyl ether (2 L) keeping the temperature of the quench pot between 10 and 15° C. The layers were separated, and the aqueous layer was extracted once with ether (1 L). The combined organic layers were combined, washed with water until the washes were neutral (5×1.5 L washes), dried with MgSO$_4$ and concentrated to provide 288 g (95% yield) of a light yellow-orange oil of 96% purity (HPLC). This material can be further purified by distillation (bp 109° C. at 79 mmHg).

Preparation of 5-(4-Chloro-5-trifluoromethyl-pyrimidin-2-ylamino)-1,3-dihydro-indol-2-one (4)

To a solution of 5-trifluoromethyl-2,4-dichloropyrimidine (214.8 g; 0.921 mol) in 1:1 DCE/tBuOH (1.240 L) was added Zinc chloride 1M solution in ether (1 eq; 0.921 L). After 0.5 hour, 5-amino-oxindole (124 g; 0.837 mol) was added followed by triethylamine (129.4 ml; 0.921 mol) keeping temperature at 25° C. The reaction was allowed to stir at room temperature overnight, then was concentrated and the product triturated from methanol as a yellow solid (224.3 g; 82%). $^1$H NMR (DMSO-d$_6$, 400 MHz) □ 3.29 (s, 2H), 6.76 (d, J=7.9 Hz, 2H), 7.39 (d, J=8.3 Hz), 7.51 (br s, 1H), 8.71 (s, 1H), 10.33 (s, 1H), 10.49 (s, 1H), $^{13}$C NMR (DMSO-d$_6$, 100 MHz) □ 177.0, 161.3, 158.7 (br), 140.7, 132.8, 126.9, 123.7 (q, J=268 Hz), 121.0, 118.7, 111.2 (q, J=32 Hz), 109.6, 36.7; HPLC ret. time: 5.759 min. LRMS (M+) 329.1, 331.1.

Example 1

5-[4-(R-1-Phenyl-ethylamino)-5-trifluoromethyl-pyrimidin-2-ylamino]-1,3-dihydro-indol-2-one

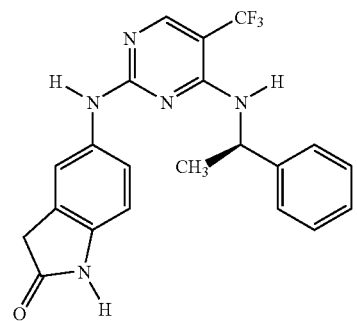

To a solution of 1:1 DCE/t-BuOH alcohol (1:1 ratio, 4 mL) and 5-(4-Chloro-5-trifluoromethyl-pyrimidin-2-ylamino)-1,3-dihydro-indol-2-one (0.15 g; 0.456 mmole) was added (R)(+) alpha phenethyl amine (0.071 mL; 0.547 mmole) and diisopropyl ethyl amine (0.081 mL, 0.456 mmole). The resultant solution was stirred under nitrogen and heated to 80° C. for 16 hours. The reaction was cooled to room temperature, diluted with ~10 mL of a 1:1 mixture of dichloromethane and methanol followed by the addition of 0.5 g of MP-carbonate. The resultant mixture was stirred, filtered, concentrated and purified by silica gel chromatography (97:2.8:0.3 ratio of chloroform/methanol/concentrated ammonium hydroxide). The desired title compounds was obtained as a white solid (0.021 g; 11%). HPLC ret. time: 6.46 min. LRMS (M+)413.4

The following compounds of the invention were prepared by heating chloropyrimidine (4) with an appropriate amine as in Example 1. Amines used in these reactions were either obtained commercially and used as received or alternatively they were prepared by common synthetic methods for amines known to those skilled in the art. Unless otherwise noted, compounds having chiral centers were prepared as racemic mixtures.

TABLE 1

Compounds Prepared by the Method of Example 1:

| Compound Name | HPLC Retention Time (min.) | MS Data (M + H) |
| --- | --- | --- |
| N-(1-Methyl-1-phenyl-ethyl)-3-{[2-(2-oxo-2,3-dihydro-1H-indol-5-ylamino)-5-trifluoromethyl-pyrimidin-4-ylamino]-methyl}-benzenesulfonamide | 6.46 | 597.5 |
| 3-{[2-(2-Oxo-2,3-dihydro-1H-indol-5-ylamino)-5-trifluoromethyl-pyrimidin-4-ylamino]-methyl}-benzenesulfonamide | 4.87 | 479.1 |
| 5-{4-[3-(Trifluoro-methanesulfonyl)-benzylamino]-5-trifluoromethyl-pyrimidin-2-ylamino}-1,3-dihydro-indol-2-one | 6.35 | 532.1 |
| 5-{4-[(Piperidin-3-ylmethyl)-amino]-5-trifluoromethyl-pyrimidin-2-ylamino}-1,3-dihydro-indol-2-one | 3.74 | 407.3 |
| 5-{4-[(1-Methanesulfonyl-piperidin-3-ylmethyl)-amino]-5-trifluoromethyl-pyrimidin-2-ylamino}-1,3-dihydro-indol-2-one | 5.21 | 485.2 |
| N-(3-{[2-(2-Oxo-2,3-dihydro-1H-indol-5-ylamino)-5-trifluoromethyl-pyrimidin-4-ylamino]-methyl}-phenyl)-methanesulfonamide | 5.22 | 493.3 |

TABLE 1-continued

Compounds Prepared by the Method of Example 1:

| Compound Name | HPLC Retention Time (min.) | MS Data (M + H) |
|---|---|---|
| 3-Oxo-3-(3-{[2-(2-oxo-2,3-dihydro-1H-indol-5-ylamino)-5-trifluoromethyl-pyrimidin-4-ylamino]-methyl}-piperidin-1-yl)-propionitrile | 4.92 | 474.3 |
| 5-{4-[3-(1,1-Dioxo-1N$^6$-isothiazolidin-2-yl)-propylamino]-5-trifluoromethyl-pyrimidin-2-ylamino}-1,3-dihydro-indol-2-one | 4.89 | 471.1 |
| 5-[4-(2-Methyl-butylamino)-5-trifluoromethyl-pyrimidin-2-ylamino]-1,3-dihydro-indol-2-one | 6.53 | 380.3 |
| 5-{4-[(1-Methanesulfonyl-piperidin-2-ylmethyl)-amino]-5-trifluoromethyl-pyrimidin-2-ylamino}-1,3-dihydro-indol-2-one | 5.17 | 485.3 |
| N-{2-[2-(2-Oxo-2,3-dihydro-1H-indol-5-ylamino)-5-trifluoromethyl-pyrimidin-4-ylamino]-ethyl}-methanesulfonamide | 4.38 | 431.2 |
| N-{4-[2-(2-Oxo-2,3-dihydro-1H-indol-5-ylamino)-5-trifluoromethyl-pyrimidin-4-ylamino]-butyl}-methanesulfonamide | 4.78 | 459.3 |
| 5-{4-[(1-Methanesulfonyl-piperidin-4-ylmethyl)-amino]-5-trifluoromethyl-pyrimidin-2-ylamino}-1,3-dihydro-indol-2-one | 5.22 | 485.3 |
| N-Methyl-N-{2-[2-(2-oxo-2,3-dihydro-1H-indol-5-ylamino)-5-trifluoromethyl-pyrimidin-4-ylamino]-ethyl}-methanesulfonamide | 4.81 | 445.1 |
| Methanesulfonic acid 3-{[2-(2-oxo-2,3-dihydro-1H-indol-5-ylamino)-5-trifluoromethyl-pyrimidin-4-ylamino]-methyl}-phenyl ester | 5.67 | 494.1 |
| N-{3-[2-(2-Oxo-2,3-dihydro-1H-indol-5-ylamino)-5-trifluoromethyl-pyrimidin-4-ylamino]-propyl}-methanesulfonamide | 4.58 | 445.1 |
| 5-{4-[(4-Methanesulfonyl-morpholin-2-ylmethyl)-amino]-5-trifluoromethyl-pyrimidin-2-ylamino}-1,3-dihydro-indol-2-one | 4.87 | 487.2 |
| N-(4-Fluoro-3-{[2-(2-oxo-2,3-dihydro-1H-indol-5-ylamino)-5-trifluoromethyl-pyrimidin-4-ylamino]-methyl}-phenyl)-methanesulfonamide | 5.29 | 511.1 |
| 5-{4-[(5-Oxo-morpholin-2-ylmethyl)-amino]-5-trifluoromethyl-pyrimidin-2-ylamino}-1,3-dihydro-indol-2-one | 4.12 | 423.3 |
| N-(4-Methoxy-3-{[2-(2-oxo-2,3-dihydro-1H-indol-5-ylamino)-5-trifluoromethyl-pyrimidin-4-ylamino]-methyl}-phenyl)-methanesulfonamide | 5.38 | 523.2 |
| N-(4-Methyl-3-{[2-(2-oxo-2,3-dihydro-1H-indol-5-ylamino)-5-trifluoromethyl-pyrimidin-4-ylamino]-methyl}-phenyl)-methanesulfonamide | 5.30 | 507.2 |
| 5-[4-(3-Methanesulfonylmethyl-benzylamino)-5-trifluoromethyl-pyrimidin-2-ylamino]-1,3-dihydro-indol-2-one | 5.14 | 492.2 |
| 5-{4-[(4-Trifluoroacetyl-morpholin-2-ylmethyl)-amino]-5-trifluoromethyl-pyrimidin-2-ylamino}-1,3-dihydro-indol-2-one | 5.64 | 505.1 |
| 5-{4-[(1-Methanesulfonyl-azetidin-3-ylmethyl)-amino]-5-trifluoromethyl-pyrimidin-2-ylamino}-1,3-dihydro-indol-2-one | 4.76 | 457.2 |
| N-Methyl-N-(4-methyl-3-{[2-(2-oxo-2,3-dihydro-1H-indol-5-ylamino)-5-trifluoromethyl-pyrimidin-4-ylamino]-methyl}-phenyl)-methanesulfonamide | 6.66 | 521.3 |
| 5-{4-[(1-Methanesulfonyl-pyrrolidin-3-ylmethyl)-amino]-5-trifluoromethyl-pyrimidin-2-ylamino}-1,3-dihydro-indol-2-one | 4.97 | 471.2 |
| N-Methyl-N-{3-[2-(2-oxo-2,3-dihydro-1H-indol-5-ylamino)-5-trifluoromethyl-pyrimidin-4-ylamino]-propyl}-methanesulfonamide | 5.02 | 459.2 |
| 5-{4-[2-(1-Methanesulfonyl-piperidin-2-yl)-ethylamino]-5-trifluoromethyl-pyrimidin-2-ylamino}-1,3-dihydro-indol-2-one | 5.71 | 499.4 |
| 5-{4-[(4-Methanesulfonyl-pyridin-2-ylmethyl)-amino]-5-trifluoromethyl-pyrimidin-2-ylamino}-1,3-dihydro-indol-2-one | 4.68 | 479.1 |
| {2,2-Dimethyl-3-[2-(2-oxo-2,3-dihydro-1H-indol-5-ylamino)-5-trifluoromethyl-pyrimidin-4-ylamino]-propyl}-carbamic acid tert-butyl ester | 7.01 | 495.0 |
| 5-[4-(3-Isopropoxy-propylamino)-5-trifluoromethyl-pyrimidin-2-ylamino]-1,3-dihydro-indol-2-one | 6.27 | 410.4 |

TABLE 1-continued

Compounds Prepared by the Method of Example 1:

| Compound Name | HPLC Retention Time (min.) | MS Data (M + H) |
|---|---|---|
| 5-{4-[(1-Methyl-piperidin-3-ylmethyl)-amino]-5-trifluoromethyl-pyrimidin-2-ylamino}-1,3-dihydro-indol-2-one | 3.71 | 421.0 |
| 5-{4-[(Tetrahydro-pyran-4-ylmethyl)-amino]-5-trifluoromethyl-pyrimidin-2-ylamino}-1,3-dihydro-indol-2-one | 5.16 | 408.3 |
| 5-[4-(2-Ethyl-butylamino)-5-trifluoromethyl-pyrimidin-2-ylamino]-1,3-dihydro-indol-2-one | 6.95 | 394.3 |
| 5-{4-[(Tetrahydro-furan-2R-ylmethyl)-amino]-5-trifluoromethyl-pyrimidin-2-ylamino}-1,3-dihydro-indol-2-one | 5.30 | 394.3 |
| 5-{4-[(Tetrahydro-furan-2S-ylmethyl)-amino]-5-trifluoromethyl-pyrimidin-2-ylamino}-1,3-dihydro-indol-2-one | 5.30 | 394.3 |
| 5-{4-[(5-Methyl-furan-2-ylmethyl)-amino]-5-trifluoromethyl-pyrimidin-2-ylamino}-1,3-dihydro-indol-2-one | 5.98 | 404.2 |
| 5-{4-[(1-Methanesulfonyl-pyrrolidin-2-ylmethyl)-amino]-5-trifluoromethyl-pyrimidin-2-ylamino}-1,3-dihydro-indol-2-one | 5.08 | 471.3 |
| 5-{4-[(Adamantan-2-ylmethyl)-amino]-5-trifluoromethyl-pyrimidin-2-ylamino}-1,3-dihydro-indol-2-one | 7.89 | 458.3 |
| 5-{4-[(Adamantan-2-ylmethyl)-amino]-5-trifluoromethyl-pyrimidin-2-ylamino}-1,3-dihydro-indol-2-one | 5.20 | 473.3 |
| 5-[4-(2-Methoxy-2-methyl-propylamino)-5-trifluoromethyl-pyrimidin-2-ylamino]-1,3-dihydro-indol-2-one | 5.87 | 396.3 |
| 5-{4-[(endo-Bicyclo[2.2.1]hept-5-en-2-ylmethyl)-amino]-5-trifluoromethyl-pyrimidin-2-ylamino}-1,3-dihydro-indol-2-one | 6.74 | 416.3 |
| (3-{[2-(2-Oxo-2,3-dihydro-1H-indol-5-ylamino)-5-trifluoromethyl-pyrimidin-4-ylamino]-methyl}-benzyl)-phosphonic acid dimethyl ester | 5.03 | 522.2 |
| 5-[4-(3-Methyl-butylamino)-5-trifluoromethyl-pyrimidin-2-ylamino]-1,3-dihydro-indol-2-one | 6.87 | 380.2 |
| 5-{4-[(2-Hydroxy-cyclohexylmethyl)-amino]-5-trifluoromethyl-pyrimidin-2-ylamino}-1,3-dihydro-indol-2-one | 6.66 | 422.2 |
| N-(4-Methoxy-3-{[2-(2-oxo-2,3-dihydro-1H-indol-5-ylamino)-5-trifluoromethyl-pyrimidin-4-ylamino]-methyl}-phenyl)-N-methyl-methanesulfonamide | 5.69 | 537.2 |
| 5-{4-[(4-Ethanesulfonyl-morpholin-2-ylmethyl)-amino]-5-trifluoromethyl-pyrimidin-2-ylamino}-1,3-dihydro-indol-2-one | 5.11 | 501.3 |
| 5-(4-{[4-(Propane-2-sulfonyl)-morpholin-2-ylmethyl]-amino}-5-trifluoromethyl-pyrimidin-2-ylamino)-1,3-dihydro-indol-2-one | 5.35 | 515.2 |
| 5-{4-[(4-Acetyl-morpholin-2-ylmethyl)-amino]-5-trifluoromethyl-pyrimidin-2-ylamino}-1,3-dihydro-indol-2-one | 4.43 | 451.2 |
| 5-{4-[(4-Propionyl-morpholin-2-ylmethyl)-amino]-5-trifluoromethyl-pyrimidin-2-ylamino}-1,3-dihydro-indol-2-one | 4.74 | 465.2 |
| 5-(4-{[4-(2,2-Dimethyl-propionyl)-morpholin-2-ylmethyl]-amino}-5-trifluoromethyl-pyrimidin-2-ylamino)-1,3-dihydro-indol-2-one | 5.43 | 493.2 |
| 2-{[2-(2-Oxo-2,3-dihydro-1H-indol-5-ylamino)-5-trifluoromethyl-pyrimidin-4-ylamino]-methyl}-morpholine-4-carboxylic acid methyl ester | 5.04 | 467.2 |
| 5-{4-[(4-Methoxyacetyl-morpholin-2-ylmethyl)-amino]-5-trifluoromethyl-pyrimidin-2-ylamino}-1,3-dihydro-indol-2-one | 4.44 | 481.2 |
| 5-[4-(3-Ethanesulfonyl-benzylamino)-5-trifluoromethyl-pyrimidin-2-ylamino]-1,3-dihydro-indol-2-one | 5.36 | 492.3 |
| 5-{4-[(4-Methanesulfonyl-morpholin-2R-ylmethyl)-amino]-5-trifluoromethyl-pyrimidin-2-ylamino}-1,3-dihydro-indol-2-one | 4.84 | 487.3 |
| 5-{4-[(4-Methanesulfonyl-morpholin-2S-ylmethyl)-amino]-5-trifluoromethyl-pyrimidin-2-ylamino}-1,3-dihydro-indol-2-one | 4.86 | 487.3 |
| 5-{4-[(Pyrimidin-2-ylmethyl)-amino]-5-trifluoromethyl-pyrimidin-2-ylamino}-1,3-dihydro-indol-2-one | 4.53 | 402.3 |
| 5-{4-[(Pyrazin-2-ylmethyl)-amino]-5-trifluoromethyl- | 4.42 | 402.1 |

TABLE 1-continued

Compounds Prepared by the Method of Example 1:

| Compound Name | HPLC Retention Time (min.) | MS Data (M + H) |
|---|---|---|
| pyrimidin-2-ylamino}-1,3-dihydro-indol-2-one | | |
| N-(4-Fluoro-3-{[2-(2-oxo-2,3-dihydro-1H-indol-5-ylamino)-5-trifluoromethyl-pyrimidin-4-ylamino]-methyl}-phenyl)-N-methyl-methanesulfonamide | 5.55 | 523.3 |
| 5-{4-[(1-Methanesulfonyl-piperidin-3-ylmethyl)-amino]-5-trifluoromethyl-pyrimidin-2-ylamino}-1,3-dihydro-indol-2-one | 5.17 | 485.3 |
| 5-{4-[(4-Isobutyryl-morpholin-2-ylmethyl)-amino]-5-trifluoromethyl-pyrimidin-2-ylamino}-1,3-dihydro-indol-2-one | 5.03 | 479.2 |
| 5-[4-(3,3-Dimethyl-2-oxo-butylamino)-5-trifluoromethyl-pyrimidin-2-ylamino]-1,3-dihydro-indol-2-one | 6.00 | 408.2 |
| 5-[4-(1,2-Dimethyl-propylamino)-5-trifluoromethyl-pyrimidin-2-ylamino]-1,3-dihydro-indol-2-one | 6.65 | 380.3 |
| 5-[4-(2-Methoxy-1-methyl-ethylamino)-5-trifluoromethyl-pyrimidin-2-ylamino]-1,3-dihydro-indol-2-one | 5.57 | 382.3 |
| 5-{4-[2-(1,1-Dioxo-1D$^6$-isothiazolidin-2-yl)-ethylamino]-5-trifluoromethyl-pyrimidin-2-ylamino}-1,3-dihydro-indol-2-one | 4.59 | 457.3 |
| 5-[4-(3-Methylamino-propylamino)-5-trifluoromethyl-pyrimidin-2-ylamino]-1,3-dihydro-indol-2-one | 3.47 | 381.3 |
| 5-{4-[(Pyridin-3-ylmethyl)-amino]-5-trifluoromethyl-pyrimidin-2-ylamino}-1,3-dihydro-indol-2-one | 4.62 | 401.3 |
| 5-{4-[(6-Methanesulfonyl-pyridin-2-ylmethyl)-amino]-5-trifluoromethyl-pyrimidin-2-ylamino}-1,3-dihydro-indol-2-one | 4.89 | 479.3 |
| 5-{4-[3-(1,1-Dioxo-1,I,6-isothiazolidin-2-yl)-benzylamino]-5-trifluoromethyl-pyrimidin-2-ylamino}-1,3-dihydro-indol-2-one | 5.45 | 519.2 |
| 5-[4-(1R-Phenyl-ethylamino)-5-trifluoromethyl-pyrimidin-2-ylamino]-1,3-dihydro-indol-2-one | 6.42 | 414.4 |
| 5-(4-Isopropylamino-5-trifluoromethyl-pyrimidin-2-ylamino)-1,3-dihydro-indol-2-one | 5.84 | 352.2 |
| 5-(4R-sec-Butylamino-5-trifluoromethyl-pyrimidin-2-ylamino)-1,3-dihydro-indol-2-one | 6.22 | 366.2 |
| 5-(4S-sec-Butylamino-5-trifluoromethyl-pyrimidin-2-ylamino)-1,3-dihydro-indol-2-one | 6.23 | 366.2 |
| 5-[4-(2-Methylamino-ethylamino)-5-trifluoromethyl-pyrimidin-2-ylamino]-1,3-dihydro-indol-2-one | 3.29 | 367.3 |
| 5-[4-(1S-Phenyl-ethylamino)-5-trifluoromethyl-pyrimidin-2-ylamino]-1,3-dihydro-indol-2-one | 6.42 | 414.3 |
| 5-{4-[(2-Methanesulfonylmethyl-thiazol-4-ylmethyl)-amino]-5-trifluoromethyl-pyrimidin-2-ylamino}-1,3-dihydro-indol-2-one | 4.72 | 499.3 |
| 5-(4-Propylamino-5-trifluoromethyl-pyrimidin-2-ylamino)-1,3-dihydro-indol-2-one | 5.91 | 352.2 |
| 5-[4-(2-Hydroxy-1-methyl-ethylamino)-5-trifluoromethyl-pyrimidin-2-ylamino]-1,3-dihydro-indol-2-one | 4.49 | 368.2 |
| 5-[4-(1-Hydroxymethyl-propylamino)-5-trifluoromethyl-pyrimidin-2-ylamino]-1,3-dihydro-indol-2-one | 4.85 | 382.2 |
| 5-{4-[(5-Methanesulfonyl-pyridin-3-ylmethyl)-amino]-5-trifluoromethyl-pyrimidin-2-ylamino}-1,3-dihydro-indol-2-one | 4.55 | 479.4 |
| 5-{4-[(Pyridin-4-ylmethyl)-amino]-5-trifluoromethyl-pyrimidin-2-ylamino}-1,3-dihydro-indol-2-one | 4.49 | 401.2 |
| 5-[4-(1,3-Dimethyl-butylamino)-5-trifluoromethyl-pyrimidin-2-ylamino]-1,3-dihydro-indol-2-one | 6.99 | 394.3 |
| N-Isopropyl-N-{3-[2-(2-oxo-2,3-dihydro-1H-indol-5-ylamino)-5-trifluoromethyl-pyrimidin-4-ylamino]-propyl}-methanesulfonamide | 5.12 | 487.3 |
| 5-[4-(1S-Hydroxymethyl-2-methyl-propylamino)-5-trifluoromethyl-pyrimidin-2-ylamino]-1,3-dihydro-indol-2-one | 5.23 | 396.3 |
| N-Cyclohexyl-N-{3-[2-(2-oxo-2,3-dihydro-1H-indol-5-ylamino)-5-trifluoromethyl-pyrimidin-4-ylamino]-propyl}-methanesulfonamide | 6.24 | 527.2 |
| 5-[4-(1,2,3,4-Tetrahydro-naphthalen-1-ylamino)-5-trifluoromethyl-pyrimidin-2-ylamino]-1,3-dihydro-indol-2-one | 440.4 | 7.17 |
| 5-{4-[(1-Methanesulfonyl-pyrrolidin-2S-ylmethyl)-amino]-5-trifluoromethyl-pyrimidin-2-ylamino}-1,3-dihydro-indol-2-one | 5.07 | 471.2 |
| 5-{4-[(3-Methyl-thiophen-2-ylmethyl)-amino]-5- | 6.18 | 420.4 |

TABLE 1-continued

Compounds Prepared by the Method of Example 1:

| Compound Name | HPLC Retention Time (min.) | MS Data (M + H) |
|---|---|---|
| trifluoromethyl-pyrimidin-2-ylamino}-1,3-dihydro-indol-2-one | | |
| 5-{4-[(1-Methanesulfonyl-pyrrolidin-3R-ylmethyl)-amino]-5-trifluoromethyl-pyrimidin-2-ylamino}-1,3-dihydro-indol-2-one | 4.95 | 471.2 |
| 5-[4-(2-Hydroxy-1S-phenyl-ethylamino)-5-trifluoromethyl-pyrimidin-2-ylamino]-1,3-dihydro-indol-2-one | 5.28 | 430.3 |
| 5-[4-(2-Hydroxy-1S-methyl-ethylamino)-5-trifluoromethyl-pyrimidin-2-ylamino]-1,3-dihydro-indol-2-one | 4.49 | 368.3 |
| 5-[4-(1R-Hydroxymethyl-propylamino)-5-trifluoromethyl-pyrimidin-2-ylamino]-1,3-dihydro-indol-2-one | 4.85 | 382.2 |
| 5-[4-(1-Pyrimidin-4-yl-ethylamino)-5-trifluoromethyl-pyrimidin-2-ylamino]-1,3-dihydro-indol-2-one | 4.84 | 416.3 |
| 5-[4-(1,1-Dioxo-tetrahydro-1-thiophen-3-ylamino)-5-trifluoromethyl-pyrimidin-2-ylamino]-1,3-dihydro-indol-2-one | 4.67 | 426.3 |
| 5-{4-[(1H-Imidazol-2-ylmethyl)-amino]-5-trifluoromethyl-pyrimidin-2-ylamino}-1,3-dihydro-indol-2-one | 3.27 | 390.3 |
| 5-[4-(2-Piperidin-2-yl-ethylamino)-5-trifluoromethyl-pyrimidin-2-ylamino]-1,3-dihydro-indol-2-one | 3.79 | 421.4 |
| 5-[4-(Isobutyl-methyl-amino)-5-trifluoromethyl-pyrimidin-2-ylamino]-1,3-dihydro-indol-2-one | 6.82 | 380.3 |
| N-Methyl-N-(3-{[2-(2-oxo-2,3-dihydro-1H-indol-5-ylamino)-5-trifluoromethyl-pyrimidin-4-ylamino]-methyl}-phenyl)-methanesulfonamide | 5.49 | 507.4 |
| N-Ethyl-N-(3-{[2-(2-oxo-2,3-dihydro-1H-indol-5-ylamino)-5-trifluoromethyl-pyrimidin-4-ylamino]-methyl}-phenyl)-methanesulfonamide | 5.67 | 521.3 |
| 5-[4-(2-Methanesulfonyl-benzylamino)-5-trifluoromethyl-pyrimidin-2-ylamino]-1,3-dihydro-indol-2-one | 5.47 | 478.2 |
| N-Isopropyl-N-(3-{[2-(2-oxo-2,3-dihydro-1H-indol-5-ylamino)-5-trifluoromethyl-pyrimidin-4-ylamino]-methyl}-phenyl)-methanesulfonamide | 5.81 | 535.3 |
| 5-{4-[(3,4,5,6-Tetrahydro-2H-[1,2']bipyridinyl-3-ylmethyl)-amino]-5-trifluoromethyl-pyrimidin-2-ylamino}-1,3-dihydro-indol-2-one | 5.79 | 484.3 |
| 5-{4-[(1-Pyrimidin-2-yl-piperidin-3-ylmethyl)-amino]-5-trifluoromethyl-pyrimidin-2-ylamino}-1,3-dihydro-indol-2-one | 6.17 | 485.3 |
| 5-{4-[2R-(1-Methanesulfonyl-piperidin-2-yl)-ethylamino]-5-trifluoromethyl-pyrimidin-2-ylamino}-1,3-dihydro-indol-2-one | 5.70 | 499.4 |
| 5-{4-[2S-(1-Methanesulfonyl-piperidin-2-yl)-ethylamino]-5-trifluoromethyl-pyrimidin-2-ylamino}-1,3-dihydro-indol-2-one | 5.70 | 499.4 |
| 5-[4-(3-Methylsulfanyl-propylamino)-5-trifluoromethyl-pyrimidin-2-ylamino]-1,3-dihydro-indol-2-one | 5.83 | 398.2 |
| 5-[4-(1S-Hydroxymethyl-3-methylsulfanyl-propylamino)-5-trifluoromethyl-pyrimidin-2-ylamino]-1,3-dihydro-indol-2-one | 5.02 | 428.2 |
| 5-[4-(2-Hydroxy-1R-methyl-ethylamino)-5-trifluoromethyl-pyrimidin-2-ylamino]-1,3-dihydro-indol-2-one | 4.49 | 368.3 |
| 5-[4-(1R-Hydroxymethyl-2-methyl-propylamino)-5-trifluoromethyl-pyrimidin-2-ylamino]-1,3-dihydro-indol-2-one | 5.23 | 396.4 |
| N-Ethyl-N-{3-[2-(2-oxo-2,3-dihydro-1H-indol-5-ylamino)-5-trifluoromethyl-pyrimidin-4-ylamino]-propyl}-methanesulfonamide | 5.31 | 473.3 |
| 5-{4-[(1-Methanesulfonyl-pyrrolidin-3R-ylmethyl)-amino]-5-trifluoromethyl-pyrimidin-2-ylamino}-1,3-dihydro-indol-2-one | 4.94 | 471.4 |
| 5-[4-(1S-Hydroxymethyl-propylamino)-5-trifluoromethyl-pyrimidin-2-ylamino]-1,3-dihydro-indol-2-one | 4.86 | 382.3 |
| 5-[4-(3,5-Dinitro-benzylamino)-5-trifluoromethyl-pyrimidin-2-ylamino]-1,3-dihydro-indol-2-one | 6.04 | 490.1 |
| N-(2-{[2-(2-Oxo-2,3-dihydro-1H-indol-5-ylamino)-5-trifluoromethyl-pyrimidin-4-ylamino]-methyl}-phenyl)-methanesulfonamide | 5.84 | 493.1 |

TABLE 1-continued

Compounds Prepared by the Method of Example 1:

| Compound Name | HPLC Retention Time (min.) | MS Data (M + H) |
|---|---|---|
| N-Isopropyl-N-{2-[2-(2-oxo-2,3-dihydro-1H-indol-5-ylamino)-5-trifluoromethyl-pyrimidin-4-ylamino]-ethyl}-methanesulfonamide | 5.37 | 473.3 |
| 5-[4-(2-Hydroxy-1-phenyl-ethylamino)-5-trifluoromethyl-pyrimidin-2-ylamino]-1,3-dihydro-indol-2-one | 5.29 | 430.3 |
| 5-[4-(1R-Hydroxymethyl-3-methyl-butylamino)-5-trifluoromethyl-pyrimidin-2-ylamino]-1,3-dihydro-indol-2-one | 5.59 | 410.4 |
| 5-[4-(1S-Hydroxymethyl-3-methyl-butylamino)-5-trifluoromethyl-pyrimidin-2-ylamino]-1,3-dihydro-indol-2-one | 5.59 | 410.4 |
| 5-{4-[(1-Methanesulfonyl-piperidin-2S-ylmethyl)-amino]-5-trifluoromethyl-pyrimidin-2-ylamino}-1,3-dihydro-indol-2-one | 5.16 | 485.3 |
| 5-{4-[(1-Methanesulfonyl-pyrrolidin-2R-ylmesthyl)-amino]-5-trifluoromethyl-pyrimidin-2-ylamino}-1,3-dihydro-indol-2-one | 5.08 | 471.3 |
| 5-[4-(Methyl-pyridin-2-ylmethyl-amino)-5-trifluoromethyl-pyrimidin-2-ylamino]-1,3-dihydro-indol-2-one | 5.37 | 415.3 |
| 5-{4-[(3-Methanesulfonyl-benzyl)-methyl-amino]-5-trifluoromethyl-pyrimidin-2-ylamino}-1,3-dihydro-indol-2-one | 5.66 | 492.3 |
| N-Methyl-N-(2-{[2-(2-oxo-2,3-dihydro-1H-indol-5-ylamino)-5-trifluoromethyl-pyrimidin-4-ylamino]-methyl}-phenyl)-methanesulfonamide | 5.63 | 507.3 |
| 5-[4-(Methyl-pyridin-3-ylmethyl-amino)-5-trifluoromethyl-pyrimidin-2-ylamino]-1,3-dihydro-indol-2-one | 5.25 | 415.4 |
| 5-{4-[(1-Methanesulfonyl-piperidin-3-ylmethyl)-methyl-amino]-5-trifluoromethyl-pyrimidin-2-ylamino}-1,3-dihydro-indol-2-one | 5.69 | 499.4 |
| 5-[4-(Methyl-pyridin-4-ylmethyl-amino)-5-trifluoromethyl-pyrimidin-2-ylamino]-1,3-dihydro-indol-2-one | 5.12 | 415.3 |
| 5-(4-Cyclopentylamino-5-trifluoromethyl-pyrimidin-2-ylamino)-1,3-dihydro-indol-2-one | 6.47 | 378.3 |
| 5-[4-(2,6-Dimethoxy-benzylamino)-5-trifluoromethyl-pyrimidin-2-ylamino]-1,3-dihydro-indol-2-one | 6.78 | 460.3 |
| 5-{4-[(1,5-Dimethyl-1H-pyrazol-3-ylmethyl)-amino]-5-trifluoromethyl-pyrimidin-2-ylamino}-1,3-dihydro-indol-2-one | 4.99 | 418.3 |
| 5-[4-(2-Imidazol-1-yl-ethylamino)-5-trifluoromethyl-pyrimidin-2-ylamino]-1,3-dihydro-indol-2-one | 3.58 | 404.2 |
| 5-{4-[(Pyridin-2-ylmethyl)-amino]-5-trifluoromethyl-pyrimidin-2-ylamino}-1,3-dihydro-indol-2-one | 4.95 | 401.4 |
| 5-[5-Trifluoromethyl-4-(2-trifluoromethyl-benzylamino)-pyrimidin-2-ylamino]-1,3-dihydro-indol-2-one | 6.57 | 468.2 |
| 5-{4-[(3-Methyl-pyridin-2-ylmethyl)-amino]-5-trifluoromethyl-pyrimidin-2-ylamino}-1,3-dihydro-indol-2-one | 6.07 | 415.3 |
| 5-[4-(3-Methanesulfonyl-benzylamino)-5-trifluoromethyl-pyrimidin-2-ylamino]-1,3-dihydro-indol-2-one | 5.16 | 478.2 |
| 5-{4-[2-(1-Acetyl-piperidin-2-yl)-ethylamino]-5-trifluoromethyl-pyrimidin-2-ylamino}-1,3-dihydro-indol-2-one | 5.22 | 463.4 |
| 5-{4-[2-(1-Propionyl-piperidin-2-yl)-ethylamino]-5-trifluoromethyl-pyrimidin-2-ylaminol-1,3-dihydro-indol-2-one | 5.65 | 477.4 |
| 5-{4-[2-(1-Cyclopropanecarbonyl-piperidin-2-yl)-ethylamino]-5-trifluoromethyl-pyrimidin-2-ylamino}-1,3-dihydro-indol-2-one | 5.86 | 489.4 |
| 5-{4-[2-(1-Isobutyryl-piperidin-2-yl)-ethylamino]-5-trifluoromethyl-pyrimidin-2-ylamino}-1,3-dihydro-indol-2-one | 6.07 | 491.3 |
| 5-{4-[2-(1-Butyryl-piperidin-2-yl)-ethylamino]-5-trifluoromethyl-pyrimidin-2-ylamino}-1,3-dihydro-indol-2-one | 5.99 | 491.4 |
| 5-{4-[2-(1-Methoxyacetyl-piperidin-2-yl)-ethylamino]-5-trifluoromethyl-pyrimidin-2-ylamino}-1,3-dihydro-indol-2-one | 5.19 | 493.4 |
| 5-{4-[2-(1-Cyclobutanecarbonyl-piperidin-2-yl)-ethylamino]-5-trifluoromethyl-pyrimidin-2-ylamino}-1,3-dihydro-indol-2-one | 6.31 | 503.4 |

TABLE 1-continued

Compounds Prepared by the Method of Example 1:

| Compound Name | HPLC Retention Time (min.) | MS Data (M + H) |
|---|---|---|
| N-Methyl-N-{3-[2-(2-oxo-2,3-dihydro-1H-indol-5-ylamino)-5-trifluoromethyl-pyrimidin-4-ylamino]-propyl}-acetamide | 4.47 | 423.3 |
| N-Methyl-N-{3-[2-(2-oxo-2,3-dihydro-1H-indol-5-ylamino)-5-trifluoromethyl-pyrimidin-4-ylamino]-propyl}-propionamide | 4.89 | 437.45 |
| Cyclopropanecarboxylic acid methyl-{3-[2-(2-oxo-2,3-dihydro-1H-indol-5-ylamino)-5-trifluoromethyl-pyrimidin-4-ylamino]-propyl}-amide | 5.07 | 449.3 |
| N-Methyl-N-{3-[2-(2-oxo-2,3-dihydro-1H-indol-5-ylamino)-5-trifluoromethyl-pyrimidin-4-ylamino]-propyl}-isobutyramide | 5.24 | 451.3 |
| N-Methyl-N-{3-[2-(2-oxo-2,3-dihydro-1H-indol-5-ylamino)-5-trifluoromethyl-pyrimidin-4-ylamino]-propyl}-butyramide | 5.25 | 451.4 |
| 2-Methoxy-N-methyl-N-{3-[2-(2-oxo-2,3-dihydro-1H-indol-5-ylamino)-5-trifluoromethyl-pyrimidin-4-ylamino]-propyl}-acetamide | 4.47 | 453.3 |
| Cyclobutanecarboxylic acid methyl-{3-[2-(2-oxo-2,3-dihydro-1H-indol-5-ylamino)-5-trifluoromethyl-pyrimidin-4-ylamino]-propyl}-amide | 5.48 | 463.4 |
| 2,2,N-Trimethyl-N-{3-[2-(2-oxo-2,3-dihydro-1H-indol-5-ylamino)-5-trifluoromethyl-pyrimidin-4-ylamino]-propyl}-propionamide | 5.80 | 465.3 |
| 2,N-Dimethyl-N-{3-[2-(2-oxo-2,3-dihydro-1H-indol-5-ylamino)-5-trifluoromethyl-pyrimidin-4-ylamino]-propyl}-butyramide | 5.55 | 465.3 |
| N-Methyl-N-{3-[2-(2-oxo-2,3-dihydro-1H-indol-5-ylamino)-5-trifluoromethyl-pyrimidin-4-ylamino]-propyl}-benzamide | 5.38 | 485.3 |
| Isoxazole-5-carboxylic acid methyl-{3-[2-(2-oxo-2,3-dihydro-1H-indol-5-ylamino)-5-trifluoromethyl-pyrimidin-4-ylamino]-propyl}-amide | 4.91 | 476.2 |
| Morpholine-4-carboxylic acid methyl-{3-[2-(2-oxo-2,3-dihydro-1H-indol-5-ylamino)-5-trifluoromethyl-pyrimidin-4-ylamino]-propyl}-amide | 4.78 | 494.3 |
| Ethanesulfonic acid methyl-{3-[2-(2-oxo-2,3-dihydro-1H-indol-5-ylamino)-5-trifluoromethyl-pyrimidin-4-ylamino]-propyl}-amide | 5.29 | 473.3 |
| Propane-1-sulfonic acid methyl-{3-[2-(2-oxo-2,3-dihydro-1H-indol-5-ylamino)-5-trifluoromethyl-pyrimidin-4-ylamino]-propyl}-amide | 5.71 | 487.3 |
| 1,1,3-Trimethyl-3-{3-[2-(2-oxo-2,3-dihydro-1H-indol-5-ylamino)-5-trifluoromethyl-pyrimidin-4-ylamino]-propyl}-sulfonylurea | 5.53 | 488.3 |
| 2,2,2-Trifluoro-N-methyl-N-{3-[2-(2-oxo-2,3-dihydro-1H-indol-5-ylamino)-5-trifluoromethyl-pyrimidin-4-ylamino]-propyl}-acetamide | 5.80 | 477.2 |
| N-Methyl-N-{2-[2-(2-oxo-2,3-dihydro-1H-indol-5-ylamino)-5-trifluoromethyl-pyrimidin-4-ylamino]-ethyl}-acetamide | 4.23 | 409.2 |
| N-Methyl-N-{2-[2-(2-oxo-2,3-dihydro-1H-indol-5-ylamino)-5-trifluoromethyl-pyrimidin-4-ylamino]-ethyl}-propionamide | 4.61 | 423.2 |
| Cyclopropanecarboxylic acid methyl-{2-[2-(2-oxo-2,3-dihydro-1H-indol-5-ylamino)-5-trifluoromethyl-pyrimidin-4-ylamino]-ethyl}-amide | 4.77 | 435.2 |
| N-Methyl-N-{2-[2-(2-oxo-2,3-dihydro-1H-indol-5-ylamino)-5-trifluoromethyl-pyrimidin-4-ylamino]-ethyl}-isobutyramide | 4.94 | 437.2 |
| N-Methyl-N-{2-[2-(2-oxo-2,3-dihydro-1H-indol-5-ylamino)-5-trifluoromethyl-pyrimidin-4-ylamino]-ethyl}-butyramide | 4.95 | 437.2 |
| 2-Methoxy-N-methyl-N-{2-[2-(2-oxo-2,3-dihydro-1H-indol-5-ylamino)-5-trifluoromethyl-pyrimidin-4-ylamino]-ethyl}-acetamide | 4.21 | 439.2 |
| Cyclobutanecarboxylic acid methyl-{2-[2-(2-oxo-2,3-dihydro-1H-indol-5-ylamino)-5-trifluoromethyl-pyrimidin-4-ylamino]-ethyl}-amide | 5.17 | 449.3 |
| 2,2,N-Trimethyl-N-{2-[2-(2-oxo-2,3-dihydro-1H-indol-5-ylamino)-5-trifluoromethyl-pyrimidin-4-ylamino]-ethyl}-propionamide | 5.57 | 451.4 |

TABLE 1-continued

Compounds Prepared by the Method of Example 1:

| Compound Name | HPLC Retention Time (min.) | MS Data (M + H) |
|---|---|---|
| 2,N-Dimethyl-N-{2-[2-(2-oxo-2,3-dihydro-1H-indol-5-ylamino)-5-trifluoromethyl-pyrimidin-4-ylamino]-ethyl}-butyramide | 5.26 | 451.4 |
| N-Methyl-N-{2-[2-(2-oxo-2,3-dihydro-1H-indol-5-ylamino)-5-trifluoromethyl-pyrimidin-4-ylamino]-ethyl}-benzamide | 4.80 | 471.3 |
| Isoxazole-5-carboxylic acid methyl-{2-[2-(2-oxo-2,3-dihydro-1H-indol-5-ylamino)-5-trifluoromethyl-pyrimidin-4-ylamino]-ethyl}-amide | 4.51 | 462.3 |
| Morpholine-4-carboxylic acid methyl-{2-[2-(2-oxo-2,3-dihydro-1H-indol-5-ylamino)-5-trifluoromethyl-pyrimidin-4-ylamino]-ethyl}-amide | 4.41 | 480.3 |
| N-Methyl-N-{2-[2-(2-oxo-2,3-dihydro-1H-indol-5-ylamino)-5-trifluoromethyl-pyrimidin-4-ylamino]-ethyl}-methanesulfonamide | 4.77 | 445.1 |
| Ethanesulfonic acid methyl-{2-[2-(2-oxo-2,3-dihydro-1H-indol-5-ylamino)-5-trifluoromethyl-pyrimidin-4-ylamino]-ethyl}-amide | 5.03 | 459.2 |
| Propane-1-sulfonic acid methyl-{2-[2-(2-oxo-2,3-dihydro-1H-indol-5-ylamino)-5-trifluoromethyl-pyrimidin-4-ylamino]-ethyl}-amide | 5.44 | 473.3 |
| 1,1,3-Trimethyl-3-{2-[2-(2-oxo-2,3-dihydro-1H-indol-5-ylamino)-5-trifluoromethyl-pyrimidin-4-ylamino]-ethyl}-sulfonylurea | 5.49 | 474.2 |
| 2,2,2-Trifluoro-N-methyl-N-{2-[2-(2-oxo-2,3-dihydro-1H-indol-5-ylamino)-5-trifluoromethyl-pyrimidin-4-ylamino]-ethyl}-acetamide | 5.49 | 463.2 |
| 5-[4-(2-Hydroxy-ethylamino)-5-trifluoromethyl-pyrimidin-2-ylamino]-1,3-dihydro-indol-2-one | 4.05 | 354.3 |
| 5-(4-Cyclopropylamino-5-trifluoromethyl-pyrimidin-2-ylamino)-1,3-dihydro-indol-2-one | 5.41 | 350.3 |
| 5-(4-Cyclobutylamino-5-trifluoromethyl-pyrimidin-2-ylamino)-1,3-dihydro-indol-2-one | 6.01 | 364.3 |
| 5-[4-(1,4-Dimethyl-pentylamino)-5-trifluoromethyl-pyrimidin-2-ylamino]-1,3-dihydro-indol-2-one | 7.45 | 408.4 |
| 5-[4-(3-Imidazol-1-yl-propylamino)-5-trifluoromethyl-pyrimidin-2-ylamino]-1,3-dihydro-indol-2-one | 3.77 | 418.3 |
| 5-[4-(2-Phenoxy-ethylamino)-5-trifluoromethyl-pyrimidin-2-ylamino]-1,3-dihydro-indol-2-one | 6.34 | 430.3 |
| 5-[4-(1-Cyclohexyl-ethylamino)-5-trifluoromethyl-pyrimidin-2-ylamino]-1,3-dihydro-indol-2-one | 7.61 | 420.4 |
| 5-[4-(1-Hydroxymethyl-2,2-dimethyl-propylamino)-5-trifluoromethyl-pyrimidin-2-ylamino]-1,3-dihydro-indol-2-one | 5.64 | 410.4 |
| 5-[4-(1-Methoxymethyl-propylamino)-5-trifluoromethyl-pyrimidin-2-ylamino]-1,3-dihydro-indol-2-one | 5.96 | 396.3 |
| 5-[4-(Indan-2-ylamino)-5-trifluoromethyl-pyrimidin-2-ylamino]-1,3-dihydro-indol-2-one | 6.78 | 426.4 |
| 5-[4-(1,2,3,4-Tetrahydro-naphthalen-1-ylamino)-5-trifluoromethyl-pyrimidin-2-ylamino]-1,3-dihydro-indol-2-one | 7.16 | 440.3 |
| 5-(4-Cycloheptylamino-5-trifluoromethyl-pyrimidin-2-ylamino)-1,3-dihydro-indol-2-one | 7.21 | 406.3 |
| 5-{4-[2-(2-Oxo-imidazolidin-1-yl)-ethylamino]-5-trifluoromethyl-pyrimidin-2-ylamino}-1,3-dihydro-indol-2-one | 4.04 | 422.3 |
| 4-[2-(2-Oxo-2,3-dihydro-1H-indol-5-ylamino)-5-trifluoromethyl-pyrimidin-4-ylamino]-butyric acid ethyl ester | 5.65 | 424.2 |
| 5-[4-(2-Hydroxy-1-hydroxymethyl-ethylamino)-5-trifluoromethyl-pyrimidin-2-ylamino]-1,3-dihydro-indol-2-one | 3.72 | 384.2 |
| 5-[4-(3-Hydroxy-2,2-dimethyl-propylamino)-5-trifluoromethyl-pyrimidin-2-ylamino]-1,3-dihydro-indol-2-one | 5.09 | 396.3 |
| 5-{4-[(Isochroman-1-ylmethyl)-amino]-5-trifluoromethyl-pyrimidin-2-ylamino}-1,3-dihydro-indol-2-one | 6.36 | 456.3 |
| 5-[4-(4-Hydroxy-1,1-dioxo-tetrahydro-1&-thiophen-3-ylamino)-5-trifluoromethyl-pyrimidin-2-ylamino]-1,3-dihydro-indol-2-one | 4.42 | 442.2 |
| 5-[4-(2-Methoxy-1-methyl-ethylamino)-5-trifluoromethyl-pyrimidin-2-ylamino]-1,3-dihydro-indol-2-one | 5.58 | 382.3 |
| 5-[4-(trans-4-Methylsulfanyl-tetrahydro-furan-3-ylamino)- | 5.37 | 426.3 |

TABLE 1-continued

Compounds Prepared by the Method of Example 1:

| Compound Name | HPLC Retention Time (min.) | MS Data (M + H) |
|---|---|---|
| 5-trifluoromethyl-pyrimidin-2-ylamino]-1,3-dihydro-indol-2-one | | |
| 5-{4-[trans-2-(Pyrimidin-2-ylsulfanyl)-cyclopentylamino]-5-trifluoromethyl-pyrimidin-2-ylamino}-1,3-dihydro-indol-2-one | 6.32 | 488.3 |
| 5-[4-(Indan-1-ylamino)-5-trifluoromethyl-pyrimidin-2-ylamino]-1,3-dihydro-indol-2-one | 6.86 | 426.3 |
| 5-{4-[2-(2-Hydroxy-ethylsulfanyl)-ethylamino]-5-trifluoromethyl-pyrimidin-2-ylamino}-1,3-dihydro-indol-2-one | 4.66 | 414.3 |
| 5-{4-[2-(Pyridin-3-yloxy)-propylamino]-5-trifluoromethyl-pyrimidin-2-ylamino}-1,3-dihydro-indol-2-one | 5.20 | 445.3 |
| 5-{4-[2-(6-Methyl-pyridin-2-yl)-ethylamino]-5-trifluoromethyl-pyrimidin-2-ylamino}-1,3-dihydro-indol-2-one | 5.00 | 429.3 |
| 5-{4-[(2,3-Dihydro-benzo[1,4]dioxin-2-ylmethyl)-amino]-5-trifluoromethyl-pyrimidin-2-ylamino}-1,3-dihydro-indol-2-one | 5.01 | 458.2 |
| 5-{4-[(1-Methyl-1H-pyrazol-4-ylmethyl)-amino]-5-trifluoromethyl-pyrimidin-2-ylamino}-1,3-dihydro-indol-2-one | 4.60 | 404.3 |
| 5-{4-[(4,5,6,7-Tetrahydro-benzothiazol-2-ylmethyl)-amino]-5-trifluoromethyl-pyrimidin-2-ylamino}-1,3-dihydro-indol-2-one | 5.93 | 461.2 |
| 5-[4-(1-Phenyl-3-[1,2,4]triazol-1-yl-propylamino)-5-trifluoromethyl-pyrimidin-2-ylamino]-1,3-dihydro-indol-2-one | 5.24 | 495.2 |
| 5-(4-Isobutylamino-5-trifluoromethyl-pyrimidin-2-ylamino)-1,3-dihydro-indol-2-one | 6.12 | 366.4 |
| 5-[4-(2-Cyclohexyl-1-hydroxymethyl-ethylamino)-5-trifluoromethyl-pyrimidin-2-ylamino]-1,3-dihydro-indol-2-one | 6.41 | 450.4 |
| 2-[2-(2-Oxo-2,3-dihydro-1H-indol-5-ylamino)-5-trifluoromethyl-pyrimidin-4-ylamino]-propionic acid methyl ester | 5.26 | 396.3 |
| 5-(4-Cyclohexylamino-5-trifluoromethyl-pyrimidin-2-ylamino)-1,3-dihydro-indol-2-one | 6.82 | 392.3 |
| 5-[4-(3-Hydroxy-propylamino)-5-trifluoromethyl-pyrimidin-2-ylamino]-1,3-dihydro-indol-2-one | 4.24 | 368.3 |
| 5-{4-[2-(4-Methyl-1H-imidazol-2-yl)-ethylamino]-5-trifluoromethyl-pyrimidin-2-ylamino}-1,3-dihydro-indol-2-one | 3.54 | 418.3 |
| 5-[4-(Tetrahydro-furan-3-ylamino)-5-trifluoromethyl-pyrimidin-2-ylamino]-1,3-dihydro-indol-2-one | 4.89 | 380.3 |
| 5-[4-(Dicyclopropylmethyl-amino)-5-trifluoromethyl-pyrimidin-2-ylamino]-1,3-dihydro-indol-2-one | 6.59 | 404.3 |
| 5-{4-[2-(5-Methyl-4H-[1,2,4]triazol-3-yl)-ethylamino]-5-trifluoromethyl-pyrimidin-2-ylamino}-1,3-dihydro-indol-2-one | 4.00 | 419.3 |
| 5-[4-(2-Ethylsulfanyl-ethylamino)-5-trifluoromethyl-pyrimidin-2-ylamino]-1,3-dihydro-indol-2-one | 5.99 | 398.3 |
| 5-[4-(2-Phenoxy-propylamino)-5-trifluoromethyl-pyrimidin-2-ylamino]-1,3-dihydro-indol-2-one | 6.57 | 444.2 |
| 5-{4-[(1-Ethyl-5-oxo-pyrrolidin-3-ylmethyl)-amino]-5-trifluoromethyl-pyrimidin-2-ylamino}-1,3-dihydro-indol-2-one | 4.57 | 435.2 |
| 5-(4-{[1-(2-Methoxy-ethyl)-5-oxo-pyrrolidin-3-ylmethyl]-amino}-5-trifluoromethyl-pyrimidin-2-ylamino)-1,3-dihydro-indol-2-one | 4.44 | 465.2 |
| 5-[4-(Benzhydryl-amino)-5-trifluoromethyl-pyrimidin-2-ylamino]-1,3-dihydro-indol-2-one | 7.26 | 476.2 |
| 5-{4-[2-(1-Methyl-1H-pyrazol-4-yl)-ethylamino]-5-trifluoromethyl-pyrimidin-2-ylamino}-1,3-dihydro-indol-2-one | 4.90 | 418.3 |
| 5-{4-[(4-Methyl-1H-imidazol-2-ylmethyl)-amino]-5-trifluoromethyl-pyrimidin-2-ylamino}-1,3-dihydro-indol-2-one | 3.40 | 404.2 |
| 5-{4-[(5-Cyclopropyl-1H-pyrazol-3-ylmethyl)-amino]-5-trifluoromethyl-pyrimidin-2-ylamino}-1,3-dihydro-indol-2-one | 5.00 | 430.2 |
| 5-{4-[2-(4-Methyl-thiazol-5-yl)-ethylamino]-5-trifluoromethyl-pyrimidin-2-ylamino}-1,3-dihydro-indol-2-one | 5.18 | 435.2 |

TABLE 1-continued

Compounds Prepared by the Method of Example 1:

| Compound Name | HPLC Retention Time (min.) | MS Data (M + H) |
|---|---|---|
| 5-{4-[2-(1H-Benzoimidazol-2-yl)-ethylamino]-5-trifluoromethyl-pyrimidin-2-ylamino}-1,3-dihydro-indol-2-one | 4.39 | 454.2 |
| 5-{4-[(5-Methyl-[1,3,4]oxadiazol-2-ylmethyl)-amino]-5-trifluoromethyl-pyrimidin-2-ylamino}-1,3-dihydro-indol-2-one | 4.25 | 406.3 |
| 5-{4-[(5-Phenyl-4H-[1,2,4]triazol-3-ylmethyl)-amino]-5-trifluoromethyl-pyrimidin-2-ylamino}-1,3-dihydro-indol-2-one | 4.92 | 467.3 |
| 5-{4-[(1H-Indol-2-ylmethyl)-amino]-5-trifluoromethyl-pyrimidin-2-ylamino}-1,3-dihydro-indol-2-one | 6.10 | 439.3 |
| 5-{4-[(1,5-Dimethyl-1H-pyrazol-4-ylmethyl)-amino]-5-trifluoromethyl-pyrimidin-2-ylamino}-1,3-dihydro-indol-2-one | 4.77 | 418.3 |
| 5-{4-[(Benzothiazol-2-ylmethyl)-amino]-5-trifluoromethyl-pyrimidin-2-ylamino}-1,3-dihydro-indol-2-one | 5.77 | 457.2 |
| 5-{4-[(3-Methyl-isoxazol-5-ylmethyl)-amino]-5-trifluoromethyl-pyrimidin-2-ylamino}-1,3-dihydro-indol-2-one | 5.02 | 405.3 |
| 5-{4-[(4-Methyl-thiazol-2-ylmethyl)-amino]-5-trifluoromethyl-pyrimidin-2-ylamino}-1,3-dihydro-indol-2-one | 5.12 | 421.2 |
| 5-{4-[1-(4-Methyl-thiazol-2-yl)-ethylamino]-5-trifluoromethyl-pyrimidin-2-ylamino}-1,3-dihydro-indol-2-one | 5.62 | 435.2 |
| 5-{5-Trifluoromethyl-4-[(1,3,5-trimethyl-1H-pyrazol-4-ylmethyl)-amino]-pyrimidin-2-ylamino}-1,3-dihydro-indol-2-one | 4.95 | 432.2 |
| 5-{4-[1-(2-Methyl-thiazol-4-yl)-ethylamino]-5-trifluoromethyl-pyrimidin-2-ylamino}-1,3-dihydro-indol-2-one | 5.69 | 435.3 |
| 5-{4-[(3-Methyl-imidazo[2,1-b]thiazol-6-ylmethyl)-amino]-5-trifluoromethyl-pyrimidin-2-ylamino}-1,3-dihydro-indol-2-one | 5.03 | 460.3 |
| 5-{4-[1-(5-Methyl-4H-[1,2,4]triazol-3-yl)-ethylamino]-5-trifluoromethyl-pyrimidin-2-ylamino}-1,3-dihydro-indol-2-one | 4.20 | 419.3 |
| 5-{4-[1-(3,5-Dimethyl-1H-pyrazol-4-yl)-ethylamino]-5-trifluoromethyl-pyrimidin-2-ylamino}-1,3-dihydro-indol-2-one | 5.02 | 432.3 |
| 5-{4-[2-(3,5-Dimethyl-1H-pyrazol-4-yl)-ethylamino]-5-trifluoromethyl-pyrimidin-2-ylamino}-1,3-dihydro-indol-2-one | 4.85 | 432.4 |
| 5-{4-[2-(4,6-Dimethyl-pyrimidin-2-yl)-ethylamino]-5-trifluoromethyl-pyrimidin-2-ylamino}-1,3-dihydro-indol-2-one | 5.17 | 444.4 |
| 5-{4-[2-(4-Methyl-5,6,7,8-tetrahydro-quinazolin-2-yl)-ethylamino]-5-trifluoromethyl-pyrimidin-2-ylamino}-1,3-dihydro-indol-2-one | 5.88 | 484.4 |
| 5-[4-(2-Thiazol-4-yl-ethylamino)-5-trifluoromethyl-pyrimidin-2-ylamino]-1,3-dihydro-indol-2-one | 5.18 | 421.3 |
| 5-(4-Dimethylamino-5-trifluoromethyl-pyrimidin-2-ylamino)-1,3-dihydro-indol-2-one | 5.60 | 338.3 |
| 5-{4-[(1-Pyrimidin-2-yl-piperidin-3-ylmethyl)-amino]-5-trifluoromethyl-pyrimidin-2-ylamino}-1,3-dihydro-indol-2-one | 6.17 | 485.4 |
| 5-[4-(Indan-1-ylamino)-5-trifluoromethyl-pyrimidin-2-ylamino]-1,3-dihydro-indol-2-one | 6.85 | 426.3 |

| Name | HPLC Ret Time (min) | LRMS (MH+) |
|---|---|---|
| N-Methyl-N-{3-[({methyl-[2-(2-oxo-2,3-dihydro-1H-indol-5-ylamino)-5-trifluoromethyl-pyrimidin-4-yl]-amino})-methyl]-phenyl}-methanesulfonamide | 6.08 | 521.3 |
| N-Methyl-N-{4-methyl-3-[({methyl-[2-(2-oxo-2,3-dihydro-1H-indol-5-ylamino)-5-trifluoromethyl- | 6.24 | 535.8 |

| Name | HPLC Ret Time (min) | LRMS (MH+) |
|---|---|---|
| pyrimidin-4-yl]-amino})-methyl]-phenyl}-methanesulfonamide | | |
| N-(5-Methyl-2-{[2-(2-oxo-2,3-dihydro-1H-indol-5-ylamino)-5-trifluoromethyl-pyrimidin-4-ylamino]-methyl}-phenyl)-methanesulfonamide | 6.23 | 507.2 |
| N-(3-Methyl-2-{[2-(2-oxo-2,3-dihydro-1H-indol-5-ylamino)-5-trifluoromethyl-pyrimidin-4-ylamino]-methyl}-phenyl)-methanesulfonamide | 6.28 | 507.2 |
| N-(4-Methyl-2-{[2-(2-oxo-2,3-dihydro-1H-indol-5-ylamino)-5-trifluoromethyl-pyrimidin-4-ylamino]-methyl}-phenyl)-methanesulfonamide | 6.12 | 507.3 |
| N-(2-Methyl-6-{[2-(2-oxo-2,3-dihydro-1H-indol-5-ylamino)-5-trifluoromethyl-pyrimidin-4-ylamino]-methyl}-phenyl)-methanesulfonamide | 5.71 | 507.3 |
| 5-[4-(3-Methanesulfonyl-propylamino)-5-trifluoromethyl-pyrimidin-2-ylamino]-1,3-dihydro-indol-2-one | 4.42 | 430.4 |
| N-Methyl-N-(5-methyl-2-{[2-(2-oxo-2,3-dihydro-1H-indol-5-ylamino)-5-trifluoromethyl-pyrimidin-4-ylamino]-methyl}-phenyl)-methanesulfonamide | 5.95 | 521.2 |
| N-(3-Methanesulfonylamino-5-{[2-(2-oxo-2,3-dihydro-1H-indol-5-ylamino)-5-trifluoromethyl-pyrimidin-4-ylamino]-methyl}-phenyl)-methanesulfonamide | 4.85 | 586.2 |
| N-Methyl-N-(4-methyl-2-{[2-(2-oxo-2,3-dihydro-1H-indol-5-ylamino)-5-trifluoromethyl-pyrimidin-4-ylamino]-methyl}-phenyl)-methanesulfonamide | 5.87 | 521.3 |
| N-Methyl-N-(2-methyl-6-{[2-(2-oxo-2,3-dihydro-1H-indol-5-ylamino)-5-trifluoromethyl-pyrimidin-4-ylamino]-methyl}-phenyl)-methanesulfonamide | 5.86 | 521.3 |
| N-Methyl-N-(3-methyl-2-{[2-(2-oxo-2,3-dihydro-1H-indol-5-ylamino)-5-trifluoromethyl-pyrimidin-4-ylamino]-methyl}-phenyl)-methanesulfonamide | 5.97 | 521.3 |
| 5-{4-[((1S,2R)-2-Hydroxy-cyclohexylmethyl)-amino]-5-trifluoromethyl-pyrimidin-2-ylamino}-1,3-dihydro-indol-2-one | 5.56 | 422.3 |
| 5-[4-((1R,2S)-2-Hydroxy-indan-1-ylamino)-5-trifluoromethyl-pyrimidin-2-ylamino]-1,3-dihydro-indol-2-one | 5.66 | 442.4 |
| 5-[4-((S)-1-Hydroxymethyl-2-phenyl-ethylamino)-5-trifluoromethyl-pyrimidin-2-ylamino]-1,3-dihydro-indol-2-one | 5.54 | 444.3 |
| N-(3-(Methanesulfonyl-methyl-amino)-5-{[2-(2-oxo-2,3-dihydro-1H-indol-5-ylamino)-5-trifluoromethyl-pyrimidin-4-ylamino]-methyl}-phenyl)-N-methyl-methanesulfonamide | 5.36 | 614.2 |
| 5-{4-[(1-Hydroxy-cyclopentylmethyl)-amino]-5-trifluoromethyl-pyrimidin-2-ylamino}-1,3-dihydro-indol-2-one | 5.2 | 408.2 |
| N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide | 5.26 | 508.2 |
| N-(3-Fluoro-2-{[2-(2-oxo-2,3-dihydro-1H-indol-5-ylamino)-5-trifluoromethyl-pyrimidin-4-ylamino]-methyl}-phenyl)-N-methyl-methanesulfonamide | 5.86 | 525.2 |
| 5-{4-[2-((S)-1-Methanesulfonyl-pyrrolidin-2-yl)-ethylamino]-5-trifluoromethyl-pyrimidin-2-ylamino}-1,3-dihydro-indol-2-one | 5.32 | 485.4 |
| 5-{4-[(1-Hydroxy-cyclobutylmethyl)-amino]-5-trifluoromethyl-pyrimidin-2-ylamino}-1,3-dihydro-indol-2-one | 4.91 | 394.3 |
| 5-{4-[2-((R)-1-Methanesulfonyl-pyrrolidin-2-yl)-ethylamino]-5-trifluoromethyl-pyrimidin-2-ylamino}-1,3-dihydro-indol-2-one | 5.32 | 485.4 |
| N-(2-Fluoro-6-{[2-(2-oxo-2,3-dihydro-1H-indol-5-ylamino)-5-trifluoromethyl-pyrimidin-4-ylamino]-methyl}-phenyl)-N-methyl-methanesulfonamide | 5.92 | 525.2 |
| N-(4-Fluoro-2-{[2-(2-oxo-2,3-dihydro-1H-indol-5-ylamino)-5-trifluoromethyl-pyrimidin-4-ylamino]-methyl}-phenyl)-N-methyl-methanesulfonamide | 5.78 | 525.3 |
| N-Methyl-N-(4-{[2-(2-oxo-2,3-dihydro-1H-indol-5-ylamino)-5-trifluoromethyl-pyrimidin-4-ylamino]-methyl}-pyridin-2-yl)-methanesulfonamide | 5.17 | 508.1 |
| N-{2,2-Dimethyl-3-[2-(2-oxo-2,3-dihydro-1H-indol-5-ylamino)-5-trifluoromethyl-pyrimidin-4-ylamino]-propyl}-N-methyl-methanesulfonamide | 5.7 | 487.3 |

-continued

| Name | HPLC Ret Time (min) | LRMS (MH+) |
|---|---|---|
| N-Methyl-N-(6-{[2-(2-oxo-2,3-dihydro-1H-indol-5-ylamino)-5-trifluoromethyl-pyrimidin-4-ylamino]-methyl}-pyridin-2-yl)-methanesulfonamide | 5.61 | 508.2 |
| N-(2,4-Difluoro-6-{[2-(2-oxo-2,3-dihydro-1H-indol-5-ylamino)-5-trifluoromethyl-pyrimidin-4-ylamino]-methyl}-phenyl)-N-methyl-methanesulfonamide | 5.98 | 543.2 |
| 5-[4-((R)-1-Methanesulfonyl-piperidin-3-ylamino)-5-trifluoromethyl-pyrimidin-2-ylamino]-1,3-dihydro-indol-2-one | 5.24 | 471.3 |
| N-Methyl-N-(6-methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide | 5.58 | 522.2 |
| N-Methyl-N-(5-{[2-(2-oxo-2,3-dihydro-1H-indol-5-ylamino)-5-trifluoromethyl-pyrimidin-4-ylamino]-methyl}-pyridin-3-yl)-methanesulfonamide | 4.79 | 508.2 |
| 5-[4-(1-Methanesulfonyl-piperidin-4-ylamino)-5-trifluoromethyl-pyrimidin-2-ylamino]-1,3-dihydro-indol-2-one | 5.26 | 471.2 |
| 5-{4-[Methyl-((R)-1-phenyl-ethyl)-amino]-5-trifluoromethyl-pyrimidin-2-ylamino}-1,3-dihydro-indol-2-one | 7.23 | 428.3 |
| 5-(4-Benzylamino-5-trifluoromethyl-pyrimidin-2-ylamino)-1,3-dihydro-indol-2-one | 6.05 | 400.3 |
| N-(4,6-Dimethyl-3-{[2-(2-oxo-2,3-dihydro-1H-indol-5-ylamino)-5-trifluoromethyl-pyrimidin-4-ylamino]-methyl}-pyridin-2-yl)-N-methyl-methanesulfonamide | 6.1 | 536.3 |
| 5-(4-tert-Butylamino-5-trifluoromethyl-pyrimidin-2-ylamino)-1,3-dihydro-indol-2-one | 6.49 | 366.2 |
| 5-[4-((1R,5S,6S)-3-Methanesulfonyl-3-aza-bicyclo[3.1.0]hex-6-ylamino)-5-trifluoromethyl-pyrimidin-2-ylamino]-1,3-dihydro-indol-2-one | 4.99 | 469.3 |
| N-Methyl-N-{3-methyl-3-[2-(2-oxo-2,3-dihydro-1H-indol-5-ylamino)-5-trifluoromethyl-pyrimidin-4-ylamino]-butyl}-methanesulfonamide | 5.7 | 487.2 |
| N-(6-Methyl-3-{[2-(2-oxo-2,3-dihydro-1H-indol-5-ylamino)-5-trifluoromethyl-pyrimidin-4-ylaminol]-methyl}-pyridin-2-yl)-methanesulfonamide | 5.27 | 508.2 |
| 5-{4-[(2-Methanesulfonyl-pyridin-4-ylmethyl)-amino]-5-trifluoromethyl-pyrimidin-2-ylamino}-1,3-dihydro-indol-2-one | 4.79 | 479 |
| 2-[2-(2-Oxo-2,3-dihydro-1H-indol-5-ylamino)-5-trifluoromethyl-pyrimidin-4-ylamino]-ethanesulfonic acid amide | 4.19 | 417.1 |
| N-(3-{Methyl-[2-(2-oxo-2,3-dihydro-1H-indol-5-ylamino)-5-trifluoromethyl-pyrimidin-4-yl]-amino}-propyl)-methanesulfonamide | 5.07 | 459.3 |
| N-(2-{Methyl-[2-(2-oxo-2,3-dihydro-1H-indol-5-ylamino)-5-trifluoromethyl-pyrimidin-4-yl]-amino}-ethyl)-methanesulfonamide | 4.89 | 445.3 |
| 5-[4-(2-Methanesulfonylmethyl-benzylamino)-5-trifluoromethyl-pyrimidin-2-ylamino]-1,3-dihydro-indol-2-one | 5.38 | 492.3 |
| 2-[2-(2-Oxo-2,3-dihydro-1H-indol-5-ylamino)-5-trifluoromethyl-pyrimidin-4-ylamino]-ethanesulfonic acid dimethylamide | 5.09 | 445.2 |
| N-Methyl-N-(3-{[2-(2-oxo-2,3-dihydro-1H-indol-5-ylamino)-5-trifluoromethyl-pyrimidin-4-ylamino]-methyl}-pyrazin-2-yl)-methanesulfonamide | 5.49 | 509.2 |
| Ethanesulfonic acid methyl-(2-{[2-(2-oxo-2,3-dihydro-1H-indol-5-ylamino)-5-trifluoromethyl-pyrimidin-4-ylamino]-methyl}-phenyl)-amide | 5.96 | 521.3 |
| Ethanesulfonic acid (2-{[2-(2-oxo-2,3-dihydro-1H- | 6.23 | 507.2 |
| N-Ethyl-N-(3-{[2-(2-oxo-2,3-dihydro-1H-indol-5-ylamino)-5-trifluoromethyl-pyrimidin-4-ylamino] methyl}-pyridin-2-yl)-methanesulfonamide | 5.54 | 522.2 |
| N-{1,1-Dimethyl-3-[2-(2-oxo-2,3-dihydro-1H-indol-5-ylamino)-5-trifluoromethyl-pyrimidin-4-ylamino]-propyl}-methanesulfonamide | 5.18 | 473.1 |
| N-(5,6-Dimethyl-3-{[2-(2-oxo-2,3-dihydro-1H-indol-5-ylamino)-5-trifluoromethyl-pyrimidin-4-ylamino]-methyl}-pyrazin-2-yl)-N-methyl-methanesulfonamide | 6.31 | 537.1 |
| 5-{4-[((R)-4-Methanesulfonyl-morpholin-3-ylmethyl)-amino]-5-trifluoromethyl-pyrimidin-2-ylamino}-1,3-dihydro-indol-2-one | 4.62 | 487.2 |

-continued

| Name | HPLC Ret Time (min) | LRMS (MH+) |
|---|---|---|
| Propane-1-sulfonic acid (2-{[2-(2-oxo-2,3-dihydro-1H-indol-5-ylamino)-5-trifluoromethyl-pyrimidin-4-ylamino]-methyl}-phenyl)-amide | 6.6 | 521.2 |
| 5-{4-[2-((R)-4-Methanesulfonyl-morpholin-3-yl)-ethylamino]-5-trifluoromethyl-pyrimidin-2-ylamino}-1,3-dihydro-indol-2-one | 4.99 | 501.1 |
| Ethanesulfonic acid methyl-(3-{[2-(2-oxo-2,3-dihydro-1H-indol-5-ylamino)-5-trifluoromethyl-pyrimidin-4-ylamino]-methyl}-pyridin-2-yl)-amide | 5.64 | 522.2 |
| Trifluoro-N-methyl-N-{3-[2-(2-oxo-2,3-dihydro-1H-indol-5-ylamino)-5-trifluoromethyl-pyrimidin-4-ylamino]-propyl}-methanesulfonamide | 6.42 | 513.3 |
| Cyclopropanesulfonic acid methyl-{3-[2-(2-oxo-2,3-dihydro-1H-indol-5-ylamino)-5-trifluoromethyl-pyrimidin-4-ylamino]-propyl}-amide | 5.5 | 485.3 |
| N-Ethyl-N-(2-{[2-(2-oxo-2,3-dihydro-1H-indol-5-ylamino)-5-trifluoromethyl-pyrimidin-4-ylamino]-methyl}-phenyl)-methanesulfonamide | 5.94 | 521.2 |
| Ethanesulfonic acid methyl-(5-methyl-2-{[2-(2-oxo-2,3-dihydro-1H-indol-5-ylamino)-5-trifluoromethyl-pyrimidin-4-ylamino]-methyl}-phenyl)-amide | | |
| Ethanesulfonic acid ethyl-(2-{[2-(2-oxo-2,3-dihydro-1H-indol-5-ylamino)-5-trifluoromethyl-pyrimidin-4-ylamino]-methyl}-phenyl)-amide | 6.22 | 535 |
| Ethanesulfonic acid ethyl-(5-methyl-2-{[2-(2-oxo-2,3-dihydro-1H-indol-5-ylamino)-5-trifluoromethyl-pyrimidin-4-ylamino]-methyl}-phenyl)-amide | 6.55 | 549 |
| N-Ethyl-N-(5-methyl-2-{[2-(2-oxo-2,3-dihydro-1H-indol-5-ylamino)-5-trifluoromethyl-pyrimidin-4-ylamino]-methyl}-phenyl)-methanesulfonamide | 6.27 | 535.1 |
| Ethanesulfonic acid (5-methyl-2-{[2-(2-oxo-2,3-dihydro-1H-indol-5-ylamino)-5-trifluoromethyl-pyrimidin-4-ylamino]-methyl}-phenyl)-amide | 6.59 | 521.1 |
| Ethanesulfonic acid (3-methyl-2-{[2-(2-oxo-2,3-dihydro-1H-indol-5-ylamino)-5-trifluoromethyl-pyrimidin-4-ylamino]-methyl}-phenyl)-amide | 6.7 | 521.3 |
| Ethanesulfonic acid methyl-(3-methyl-2-{[2-(2-oxo-2,3-dihydro-1H-indol-5-ylamino)-5-trifluoromethyl-pyrimidin-4-ylamino]-methyl}-phenyl)-amide | 6.33 | 535.2 |
| 2-[2-(2-Oxo-2,3-dihydro-1H-indol-5-ylamino)-5-trifluoromethyl-pyrimidin-4-ylamino]-ethanesulfonic acid methylamide | 4.6 | 431.1 |
| Ethanesulfonic acid {3-[2-(2-oxo-2,3-dihydro-1H-indol-5-ylamino)-5-trifluoromethyl-pyrimidin-4-ylamino]-propyl}-amide | 4.87 | 459.1 |
| C-Methanesulfonyl-N-{3-[2-(2-oxo-2,3-dihydro-1H-indol-5-ylamino)-5-trifluoromethyl-pyrimidin-4-ylamino]-propyl}-methanesulfonamide | 4.84 | 523 |
| Ethanesulfonic acid {2-[2-(2-oxo-2,3-dihydro-1H-indol-5-ylamino)-5-trifluoromethyl-pyrimidin-4-ylamino]-ethyl}-amide | 4.65 | 445.2 |
| C-Methanesulfonyl-N-{2-[2-(2-oxo-2,3-dihydro-1H-indol-5-ylamino)-5-trifluoromethyl-pyrimidin-4-ylamino]-ethyl}-methanesulfonamide | 4.62 | 509 |
| N-Methyl-N-(4-methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide | 5.63 | 522.1 |
| 5-(4-{[1-(2,2,2-Trifluoro-acetyl)-piperidin-3-ylmethyl]-amino}-5-trifluoromethyl-pyrimidin-2-ylamino)-1,3-dihydro-indol-2-one | 6.04 | 503.1 |
| 2,2,2-Trifluoro-ethanesulfonic acid {3-[2-(2-oxo-2,3-dihydro-1H-indol-5-ylamino)-5-trifluoromethyl-pyrimidin-4-ylaminol]-propyl}-amide | 5.56 | 513.2 |
| N-Methyl-N-(4-{[2-(2-oxo-2,3-dihydro-1H-indol-5-ylamino)-5-trifluoromethyl-pyrimidin-4-ylamino]-methyl}-pyridin-2-yl)-methanesulfonamide | 5.21 | 509.3 |
| N-Cyclopropyl-N-(2-{[2-(2-oxo-2,3-dihydro-1H-indol-5-ylamino)-5-trifluoromethyl-pyrimidin-4-ylamino]-methyl}-phenyl)-methanesulfonamide | 6.01 | 533.3 |
| N-Methyl-N-(2-{[2-(2-oxo-2,3-dihydro-1H-indol-5-ylamino)-5-trifluoromethyl-pyrimidin-4-ylaminol]-methyl}-pyrimidin-4-yl)-methanesulfonamide | 4.95 | 509.2 |
| N-Methyl-N-(6-{[2-(2-oxo-2,3-dihydro-1H-indol-5-ylamino)-5-trifluoromethyl-pyrimidin-4-ylamino]-methyl}-pyrazin-2-yl)-methanesulfonamide | 5.3 | 509.4 |

| Name | HPLC Ret Time (min) | LRMS (MH+) |
| --- | --- | --- |
| N-Methyl-N-(2-{[2-(2-oxo-2,3-dihydro-1H-indol-5-ylamino)-5-trifluoromethyl-pyrimidin-4-ylamino]-methyl}-pyridin-3-yl)-methanesulfonamide | 5.54 | 508.3 |
| N-Methyl-N-(3-{[2-(2-oxo-2,3-dihydro-1H-indol-5-ylamino)-5-trifluoromethyl-pyrimidin-4-ylamino]-methyl}-pyridin-4-yl)-methanesulfonamide | 5.55 | 508.4 |
| N-Cyclopropyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide | 5.6 | 534.1 |
| N-Methyl-N-(6-methyl-3-{[2-(2-oxo-2,3-dihydro-1H-indol-5-ylamino)-5-trifluoromethyl-pyrimidin-4-ylamino]-methyl}-pyrazin-2-yl)-methanesulfonamide | 5.93 | 523.4 |
| 5-{4-[(2-Methanesulfonylmethyl-pyridin-3-ylmethyl)-amino]-5-trifluoromethyl-pyrimidin-2-ylamino}-1,3-dihydro-indol-2-one | 5.4 | 493.2 |
| N-Methyl-N-(4-{[2-(2-oxo-2,3-dihydro-1H-indol-5-ylamino)-5-trifluoromethyl-pyrimidin-4-ylamino]-methyl}-pyridin-3-yl)-methanesulfonamide | 4.77 | 508.2 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated herein by reference in their entireties.

The invention claimed is:

1. A compound selected from the group consisting of:
N-Methyl-N-{3-[({methyl-[2-(2-oxo-2,3-dihydro-1H-indol-5-ylamino)-5-trifluoromethyl-pyrimidin-4-yl]-amino})-methyl]-phenyl}-methanesulfonamide
N-Methyl-N-{4-methyl-3-[({methyl-[2-(2-oxo-2,3-dihydro-1H-indol-5-ylamino)-5-trifluoromethyl-pyrimidin-4-yl]-amino})-methyl]-phenyl}-methanesulfonamide
N-(5-Methyl-2-{[2-(2-oxo-2,3-dihydro-1H-indol-5-ylamino)-5-trifluoromethyl-pyrimidin-4-ylamino]-methyl}-phenyl)-methanesulfonamide
N-(3-Methyl-2-{[2-(2-oxo-2,3-dihydro-1H-indol-5-ylamino)-5-trifluoromethyl-pyrimidin-4-ylamino]-methyl}-phenyl)-methanesulfonamide
N-(4-Methyl-2-{[2-(2-oxo-2,3-dihydro-1H-indol-5-ylamino)-5-trifluoromethyl-pyrimidin-4-ylamino]-methyl}-phenyl)-methanesulfonamide
N-(2-Methyl-6-{[2-(2-oxo-2,3-dihydro-1H-indol-5-ylamino)-5-trifluoromethyl-pyrimidin-4-ylamino]-methyl}-phenyl)-methanesulfonamide
5-[4-(3-Methanesulfonyl-propylamino)-5-trifluoromethyl-pyrimidin-2-ylamino]-1,3-dihydro-indol-2-one
N-Methyl-N-(5-methyl-2-{[2-(2-oxo-2,3-dihydro-1H-indol-5-ylamino)-5-trifluoromethyl-pyrimidin-4-ylamino]-methyl}-phenyl)-methanesulfonamide
N-(3-Methanesulfonylamino-5-{[2-(2-oxo-2,3-dihydro-1H-indol-5-ylamino)-5-trifluoromethyl-pyrimidin-4-ylamino]-methyl}-phenyl)-methanesulfonamide
N-Methyl-N-(4-methyl-2-{[2-(2-oxo-2,3-dihydro-1H-indol-5-ylamino)-5-trifluoromethyl-pyrimidin-4-ylamino]-methyl}-phenyl)-methanesulfonamide
N-Methyl-N-(2-methyl-6-{[2-(2-oxo-2,3-dihydro-1H-indol-5-ylamino)-5-trifluoromethyl-pyrimidin-4-ylamino]-methyl}-phenyl)-methanesulfonamide
N-Methyl-N-(3-methyl-2-{[2-(2-oxo-2,3-dihydro-1H-indol-5-ylamino)-5-trifluoromethyl-pyrimidin-4-ylamino]-methyl}-phenyl)-methanesulfonamide
5-{4-[((1S,2R)-2-Hydroxy-cyclohexylmethyl)-amino]-5-trifluoromethyl-pyrimidin-2-ylamino}-1,3-dihydro-indol-2-one
5-[4-((1R,2S)-2-Hydroxy-indan-1-ylamino)-5-trifluoromethyl-pyrimidin-2-ylamino]-1,3-dihydro-indol-2-one
5-[4-((S)-1-Hydroxymethyl-2-phenyl-ethylamino)-5-trifluoromethyl-pyrimidin-2-ylamino]-1,3-dihydro-indol-2-one
N-(3-(Methanesulfonyl-methyl-amino)-5-{[2-(2-oxo-2,3-dihydro-1H-indol-5-ylamino)-5-trifluoromethyl-pyrimidin-4-ylamino]-methyl}-phenyl)-N-methyl-methanesulfonamide
5-{4-[(1-Hydroxy-cyclopentylmethyl)-amino]-5-trifluoromethyl-pyrimidin-2-ylamino}-1,3-dihydro-indol-2-one
N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide
N-(3-Fluoro-2-{[2-(2-oxo-2,3-dihydro-1H-indol-5-ylamino)-5-trifluoromethyl-pyrimidin-4-ylamino]-methyl}-phenyl)-N-methyl-methanesulfonamide
5-{4-[2-((S)-1-Methanesulfonyl-pyrrolidin-2-yl)-ethylamino]-5-trifluoromethyl-pyrimidin-2-ylamino}-1,3-dihydro-indol-2-one
5-{4-[(1-Hydroxy-cyclobutylmethyl)-amino]-5-trifluoromethyl-pyrimidin-2-ylamino}-1,3-dihydro-indol-2-one
5-{4-[2-((R)-1-Methanesulfonyl-pyrrolidin-2-yl)-ethylamino]-5-trifluoromethyl-pyrimidin-2-ylamino}-1,3-dihydro-indol-2-one
N-(2-Fluoro-6-{[2-(2-oxo-2,3-dihydro-1H-indol-5-ylamino)-5-trifluoromethyl-pyrimidin-4-ylamino]-methyl}-phenyl)-N-methyl-methanesulfonamide
N-(4-Fluoro-2-{[2-(2-oxo-2,3-dihydro-1H-indol-5-ylamino)-5-trifluoromethyl-pyrimidin-4-ylamino]-methyl}-phenyl)-N-methyl-methanesulfonamide
N-Methyl-N-(4-{[2-(2-oxo-2,3-dihydro-1H-indol-5-ylamino)-5-trifluoromethyl-pyrimidin-4-ylamino]-methyl}-pyridin-2-yl)-methanesulfonamide N-{2,2-Dimethyl-3-[2-(2-oxo-2,3-dihydro-1H-indol-5-ylamino)-5-trifluoromethyl-pyrimidin-4-ylamino]-propyl}-N-methyl-methanesulfonamide
N-Methyl-N-(6-{[2-(2-oxo-2,3-dihydro-1H-indol-5-ylamino)-5-trifluoromethyl-pyrimidin-4-ylamino]-methyl}-pyridin-2-yl)-methanesulfonamide
N-(2,4-Difluoro-6-{[2-(2-oxo-2,3-dihydro-1H-indol-5-ylamino)-5-trifluoromethyl-pyrimidin-4-ylamino]-methyl}-phenyl)-N-methyl-methanesulfonamide
5-[4-((R)-1-Methanesulfonyl-piperidin-3-ylamino)-5-trifluoromethyl-pyrimidin-2-ylamino]-1,3-dihydro-indol-2-one
N-Methyl-N-(6-methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(5-{[2-(2-oxo-2,3-dihydro-1H-indol-5-ylamino)-5-trifluoromethyl-pyrimidin-4-ylamino]-methyl}-pyridin-3-yl)-methanesulfonamide
5-[4-(1-Methanesulfonyl-piperidin-4-ylamino)-5-trifluoromethyl-pyrimidin-2-ylamino]-1,3-dihydro-indol-2-one
5-{4-[Methyl-((R)-1-phenyl-ethyl)-amino]-5-trifluoromethyl-pyrimidin-2-ylamino}-1,3-dihydro-indol-2-one
5-(4-Benzylamino-5-trifluoromethyl-pyrimidin-2-ylamino)-1,3-dihydro-indol-2-one
N-(4,6-Dimethyl-3-{[2-(2-oxo-2,3-dihydro-1H-indol-5-ylamino)-5-trifluoromethyl-pyrimidin-4-ylamino]-methyl}-pyridin-2-yl)-N-methyl-methanesulfonamide
5-(4-tert-Butylamino-5-trifluoromethyl-pyrimidin-2-ylamino)-1,3-dihydro-indol-2-one
5-[4-((1R,5S,6S)-3-Methanesulfonyl-3-aza-bicyclo[3.1.0]hex-6-ylamino)-5-trifluoromethyl-pyrimidin-2-ylamino]-1,3-dihydro-indol-2-one
N-Methyl-N-{3-methyl-3-[2-(2-oxo-2,3-dihydro-1H-indol-5-ylamino)-5-trifluoromethyl-pyrimidin-4-ylamino]-butyl}-methanesulfonamide
N-(6-Methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide
5-{4-[(2-Methanesulfonyl-pyridin-4-ylmethyl)-amino]-5-trifluoromethyl-pyrimidin-2-ylamino}-1,3-dihydro-indol-2-one
2-[2-(2-Oxo-2,3-dihydro-1H-indol-5-ylamino)-5-trifluoromethyl-pyrimidin-4-ylamino]-ethanesulfonic acid amide
N-(3-{Methyl-[2-(2-oxo-2,3-dihydro-1H-indol-5-ylamino)-5-trifluoromethyl-pyrimidin-4yl]-amino}-propyl)-methanesulfonamide
N-(2-{Methyl-[2-(2-oxo-2,3-dihydro-1H-indol-5-ylamino)-5-trifluoromethyl-pyrimidin-4-yl]-amino}-ethyl)-methanesulfonamide
5-[4-(2-Methanesulfonylmethyl-benzylamino)-5-trifluoromethyl-pyrimidin-2-ylamino]-1,3-dihydro-indol-2-one
2-[2-(2-Oxo-2,3-dihydro-1H-indol-5-ylamino)-5-trifluoromethyl-pyrimidin-4-ylamino]-ethanesulfonic acid dimethylamide
N-Methyl-N-(3-{[2-(2-oxo-2,3-dihydro-1H-indol-5-ylamino)-5-trifluoromethyl-pyrimidin-4-ylamino]-methyl}-pyrazin-2-yl)-methanesulfonamide
Ethanesulfonic acid methyl-(2-{[2-(2-oxo-2,3-dihydro-1H-indol-5-ylamino)-5-trifluoromethyl-pyrimidin-4-ylamino]-methyl}-phenyl)-amide
Ethanesulfonic acid (2-{[2-(2-oxo-2,3-dihydro-1H-indol-5-ylamino)-5-trifluoromethyl-pyrimidin-4-ylamino]-methyl}-phenyl)-amide
N-Ethyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide
N-{1,1-Dimethyl-3-[2-(2-oxo-2,3-dihydro-1H-indol-5-ylamino)-5-trifluoromethyl-pyrimidin-4-ylamino]-propyl}-methanesulfonamide
N-(5,6-Dimethyl-3-{[2-(2-oxo-2,3-dihydro-1H-indol-5-ylamino)-5-trifluoromethyl-pyrimidin-4-ylamino]-methyl}-pyrazin-2-yl)-N-methyl-methanesulfonamide
5-{4-[((R)-4-Methanesulfonyl-morpholin-3-ylmethyl)-amino]-5-trifluoromethyl-pyrimidin-2-ylamino}-1,3-dihydro-indol-2-one
Propane-1-sulfonic acid (2-{[2-(2-oxo-2,3-dihydro-1H-indol-5-ylamino)-5-trifluoromethyl-pyrimidin-4-ylamino]-methyl}-phenyl)-amide
5-{4-[2-((R)-4-Methanesulfonyl-morpholin-3-yl)-ethylamino]-5-trifluoromethyl-pyrimidin-2-ylamino}-1,3-dihydro-indol-2-one
Ethanesulfonic acid methyl-(3-{[2-(2-oxo-2,3-dihydro-1H-indol-5-ylamino)-5-trifluoromethyl-pyrimidin-4-ylamino]-methyl}-pyridin-2-yl)-amide
Trifluoro-N-methyl-N-{3-[2-(2-oxo-2,3-dihydro-1H-indol-5-ylamino)-5-trifluoromethyl-pyrimidin-4-ylamino]-propyl}-methanesulfonamide
Cyclopropanesulfonic acid methyl-{3-[2-(2-oxo-2,3-dihydro-1H-indol-5-ylamino)-5-trifluoromethyl-pyrimidin-4-ylamino]-propyl}-amide
N-Ethyl-N-(2-{[2-(2-oxo-2,3-dihydro-1H-indol-5-ylamino)-5-trifluoromethyl-pyrimidin-4-ylamino]-methyl}-phenyl)-methanesulfonamide
Ethanesulfonic acid methyl-(5-methyl-2-{[2-(2-oxo-2,3-dihydro-1H-indol-5-ylamino)-5-trifluoromethyl-pyrimidin-4-ylamino]-methyl}-phenyl)-amide
Ethanesulfonic acid ethyl-(2-[2-(2-oxo-2,3-dihydro-1H-indol-5-ylamino)-5-trifluoromethyl-pyrimidin-4-ylamino]-methyl}-phenyl)-amide
Ethanesulfonic acid ethyl-(5-methyl-2-{[2-(2-oxo-2,3-dihydro-1H-indol-5-ylamino)-5-trifluoromethyl-pyrimidin-4-ylamino]-methyl}-phenyl)-amide
N-Ethyl-N-(5-methyl-2-{[2-(2-oxo-2,3-dihydro-1H-indol-5-ylamino)-5-trifluoromethyl-pyrimidin-4-ylamino]-methyl}-phenyl)-methanesulfonamide
Ethanesulfonic acid (5-methyl-2-{[2-(2-oxo-2,3-dihydro-1H-indol-5-ylamino)-5-trifluoromethyl-pyrimidin-4-ylamino]-methyl}-phenyl)-amide
Ethanesulfonic acid (3-methyl-2-{[2-(2-oxo-2,3-dihydro-1H-indol-5-ylamino)-5-trifluoromethyl-pyrimidin-4-ylamino]-methyl}-phenyl)-amide
Ethanesulfonic acid methyl-(3-methyl-2-{[2-(2-oxo-2,3-dihydro-1H-indol-5-ylamino)-5-trifluoromethyl-pyrimidin-4-ylamino]-methyl}-phenyl)-amide
2-[2-(2-Oxo-2,3-dihydro-1H-indol-5-ylamino)-5-trifluoromethyl-pyrimidin-4-ylamino]-ethanesulfonic acid methylamide
Ethanesulfonic acid {3-[2-(2-oxo-2,3-dihydro-1H-indol-5-ylamino)-5-trifluoromethyl-pyrimidin-4-ylamino]-propyl}-amide
C-Methanesulfonyl-N-{3-[2-(2-oxo-2,3-dihydro-1H-indol-5-ylamino)-5-trifluoromethyl-pyrimidin-4-ylamino]-propyl}-methanesulfonamide
Ethanesulfonic acid {2-[2-(2-oxo-2,3-dihydro-1H-indol-5-ylamino)-5-trifluoromethyl-pyrimidin-4-ylamino]-ethyl}-amide
C-Methanesulfonyl-N-{2-[2-(2-oxo-2,3-dihydro-1H-indol-5-ylamino)-5-trifluoromethyl-pyrimidin-4-ylamino]-ethyl}-methanesulfonamide N-Methyl-N-(4-methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide
5-(4-{[1-(2,2,2-Trifluoro-acetyl)-piperidin-3-ylmethyl]-amino}-5-trifluoromethyl-pyrimidin-2-ylamino)-1,3-dihydro-indol-2-one
2,2,2-Trifluoro-ethanesulfonic acid {3-[2-(2-oxo-2,3-dihydro-1H-indol-5-ylamino)-5-trifluoromethyl-pyrimidin-4-ylamino]-propyl}-amide
N-Methyl-N-(4-{[2-(2-oxo-2,3-dihydro-1H-indol-5-ylamino)-5-trifluoromethyl-pyrimidin-4-ylamino]-methyl}-pyrimidin-2-yl)-methanesulfonamide
N-Cyclopropyl-N-(2-{[2-(2-oxo-2,3-dihydro-1H-indol-5-ylamino)-5-trifluoromethyl-pyrimidin-4-ylamino]-methyl}-phenyl)-methanesulfonamide
N-Methyl-N-(2-{[2-(2-oxo-2,3-dihydro-1H-indol-5-ylamino)-5-trifluoromethyl-pyrimidin-4-ylamino]-methyl}-pyrimidin-4-yl)-methanesulfonamide
N-Methyl-N-(6-{[2-(2-oxo-2,3-dihydro-1H-indol-5-ylamino)-5-trifluoromethyl-pyrimidin-4-ylamino]-methyl}-pyrazin-2-yl)-methanesulfonamide
N-Methyl-N-(2-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(3-{[2-(2-oxo-2,3-dihydro-1H-indol-5-ylamino)-5-trifluoromethyl-pyrimidin-4-ylamino]-methyl}-pyridin-4-yl)-methanesulfonamide
N-Cyclopropyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(6-methyl-3-{[2-(2-oxo-2,3-dihydro-1H-indol-5-ylamino)-5-trifluoromethyl-pyrimidin-4-ylamino]-methyl}-pyrazin-2-yl)-methanesulfonamide
5-{4-[(2-Methanesulfonylmethyl-pyridin-3-ylmethyl)-amino]-5-trifluoromethyl-pyrimidin-2-ylamino}-1,3-dihydro-indol-2-one
N-Methyl-N-(4-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(3-methyl-6-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(5-methyl-3-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(4-methyl-6-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(2-methyl-5-[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(5-methyl-6-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(6-methyl-2-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(5-methyl-2-{[2-(2-oxo-2,3-dihydro-1H-indol-5-ylamino)-5-trifluoromethyl-pyrimidin-4-ylamino]-methyl}-pyrimidin-4-yl)-methanesulfonamide
N-Methyl-N-(5-methyl-2-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(4-methyl-2-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(3-methyl-4-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(5-methyl-4-{[2-(2-oxo-2,3-dihydro-1H-indol-5-ylamino)-5-trifluoromethyl-pyrimidin-4-ylamino]-methyl}-pyrimidin-2-yl)-methanesulfonamide
N-Methyl-N-(6-methyl-5-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(6-methyl-2-{[2-(2-oxo-2,3-dihydro-1H-indol-5-ylamino)-5-trifluoromethyl-pyrimidin-4-ylamino]-methyl}-pyrimidin-4-yl)-methanesulfonamide
N-Methyl-N-(5-methyl-4-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(2-methyl-3-{[2-(2-oxo-2,3-dihydro-1H-indol-5-ylamino)-5-trifluoromethyl-pyrimidin-4-ylamino]-methyl}-pyridin-4-yl)-methanesulfonamide
N-Methyl-N-(6-methyl-4-{[2-(2-oxo-2,3-dihydro-1H-indol-5-ylamino)-5-trifluoromethyl-pyrimidin-4-ylamino]-methyl}-pyridin-2-yl)-methanesulfonamide
N-Methyl-N-(5-methyl-3-{[2-(2-oxo-2,3-dihydro-1H-indol-5-ylamino)-5-trifluoromethyl-pyrimidin-4-ylamino]-methyl}-pyridin-4-yl)-methanesulfonamide
N-Methyl-N-(5-methyl-6-{[2-(2-oxo-2,3-dihydro-1H-indol-5-ylamino)-5-trifluoromethyl-pyrimidin-4-ylamino]-methyl}-pyrimidin-4-yl)-methanesulfonamide
N-Methyl-N-(5-methyl-4-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(6-{[2-(2-oxo-2,3-dihydro-1H-indol-5-ylamino)-5-trifluoromethyl-pyrimidin-4-ylamino]-methyl}-pyrimidin-4-yl)-methanesulfonamide
N-Methyl-N-(6-methyl-4-{[2-(2-oxo-2,3-dihydro-1H-indol-5-ylamino)-5-trifluoromethyl-pyrimidin-4-ylamino]-methyl}-pyrimidin-2-yl)-methanesulfonamide
N-Methyl-N-(2-methyl-4-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(5-{[2-(2-oxo-2,3-dihydro-1H-indol-5-ylamino)-5-trifluoromethyl-pyrimidin-4-ylamino]-methyl}-pyrimidin-4-yl)-methanesulfonamide
N-Methyl-N-(2-methyl-6-{[2-(2-oxo-2,3-dihydro-1H-indol-5-ylamino)-5-trifluoromethyl-pyrimidin-4-ylamino]-methyl}-pyrimidin-4-yl)-methanesulfonamide
N-Methyl-N-(6-methyl-4-{[2-(2-oxo-2,3-dihydro-1H-indol-5-ylamino)-5-trifluoromethyl-pyrimidin-4-ylamino]-methyl}-pyridin-3-yl)-methanesulfonamide
N-Methyl-N-(4-{[2-(2-oxo-2,3-dihydro-1H-indol-5-ylamino)-5-trifluoromethyl-pyrimidin-4-ylamino]-methyl}-pyrimidin-5-yl)-methanesulfonamide
N-Methyl-N-(2-methyl-5-{[2-(2-oxo-2,3-dihydro-1H-indol-5-ylamino)-5-trifluoromethyl-pyrimidin-4-ylamino]-methyl}-pyrimidin-4-yl)-methanesulfonamide
N-Methyl-N-(4-methyl-6-{[2-(2-oxo-2,3-dihydro-1H-indol-5-ylamino)-5-trifluoromethyl-pyrimidin-4-ylamino]-methyl}-pyrimidin-5-yl)-methanesulfonamide N-Methyl-N-(5-methyl-6-{[2-(2-oxo-2,3-dihydro-1H-indol-5-ylamino)-5-trifluoromethyl-pyrimidin-4-ylamino]-methyl}-pyrazin-2-yl)-methanesulfonamide N-Methyl-N-(5-methyl-3-{[2-(2-oxo-2,3-dihydro-1H-indol-5-ylamino)-5-trifluoromethyl-pyrimidin-4-ylamino]-methyl}-pyrazin-2-yl)-methanesulfonamide N-Methyl-N-(2-methyl-6-{[2-(2-oxo-2,3-dihydro-1H-indol-5-ylamino)-5-trifluoromethyl-pyrimidin-4-ylamino]-methyl}-pyrimidin-5-yl)-methanesulfonamide N-Methyl-N-(3-methyl-6-{[2-(2-oxo-2,3-dihydro-1H-indol-5-ylamino)-5-trifluoromethyl-pyrimidin-4-ylamino]-methyl}-pyrazin-2-yl)-methanesulfonamide N-Methyl-N-(6-methyl-5-{[2-(2-oxo-2,3-dihydro-1H-indol-5-ylamino)-5-trifluoromethyl-pyrimidin-4-ylamino]-methyl}-pyrimidin-4-yl)-methanesulfonamide.

* * * * *